(12) United States Patent  (10) Patent No.: US 8,192,734 B2
Lei  (45) Date of Patent: Jun. 5, 2012

(54) COMPOSITIONS AND METHODS FOR BONE STRENGTHENING

(75) Inventor: Xingen Lei, Ithaca, NY (US)

(73) Assignee: Cornell University, Ithaca, NY (US)

( * ) Notice: Subject to any disclaimer, the term of this patent is extended or adjusted under 35 U.S.C. 154(b) by 267 days.

(21) Appl. No.: 12/170,136

(22) Filed: Jul. 9, 2008

(65) Prior Publication Data

US 2009/0155237 A1 Jun. 18, 2009

Related U.S. Application Data

(60) Provisional application No. 60/958,855, filed on Jul. 9, 2007.

(51) Int. Cl.
*A61K 38/46* (2006.01)
*A61K 33/24* (2006.01)
*A61K 31/28* (2006.01)
*C12N 9/16* (2006.01)

(52) U.S. Cl. ...... 424/94.6; 424/617; 424/1.77; 514/492; 435/196

(58) Field of Classification Search .......... 424/94.6, 424/617, 1.77; 514/492; 435/196
See application file for complete search history.

(56) References Cited

U.S. PATENT DOCUMENTS

| | | | |
|---|---|---|---|
| 3,819,528 A | 6/1974 | Berry | |
| 3,860,484 A | 1/1975 | O'Malley | |
| 3,966,971 A | 6/1976 | Morehouse et al. | |
| 4,038,140 A | 7/1977 | Jaworek et al. | |
| 4,375,514 A | 3/1983 | Siewert et al. | |
| 4,460,683 A | 7/1984 | Gloger et al. | |
| 4,470,968 A | 9/1984 | Mitra et al. | |
| 4,734,283 A | 3/1988 | Sirén | |
| 4,765,994 A | 8/1988 | Holmgren | |
| 4,778,761 A | 10/1988 | Miyanohara et al. | |
| 4,914,029 A | 4/1990 | Caransa et al. | |
| 4,915,960 A | 4/1990 | Holmgren | |
| 4,950,609 A | 8/1990 | Tischer et al. | |
| 4,997,767 A | 3/1991 | Nozaki et al. | |
| 5,024,941 A | 6/1991 | Maine et al. | |
| 5,200,399 A | 4/1993 | Wettlaufer et al. | |
| 5,268,273 A | 12/1993 | Buckholz | |

(Continued)

FOREIGN PATENT DOCUMENTS

CN 1126243 A 7/1996

(Continued)

OTHER PUBLICATIONS

Pagano et al., "Supplemental *Escherichia coli* phytase and strontium enhance bone strength of young pigs fed a phosphorous-adequate diet," J Nutrition 137:1795-1801, published on Jul. 1, 2007.*

(Continued)

*Primary Examiner* — Rosanne Kosson
(74) *Attorney, Agent, or Firm* — LeClairRyan, a Professional Corporation

(57) ABSTRACT

The invention relates to methods of increasing bone strength in an animal, preferably a mammal. In one aspect, the methods provided by the invention involve administering to the animal strontium and a phytase enzyme. In another aspect, methods are provided for treating or preventing osteoporosis in a subject, the method comprising administering to said individual a phytase enzyme and strontium. Also encompassed are animal feed compositions comprising a phytase enzyme and supplemental strontium and a dietary supplement composition for administration to a human, the composition comprising a phytase enzyme and supplemental strontium.

29 Claims, 16 Drawing Sheets

U.S. PATENT DOCUMENTS

| | | | |
|---|---|---|---|
| 5,290,765 | A | 3/1994 | Wettlaufer et al. |
| 5,316,770 | A | 5/1994 | Edwards, Jr. |
| 5,318,903 | A | 6/1994 | Bewert et al. |
| 5,366,736 | A | 11/1994 | Edwards, Jr. |
| 5,436,156 | A | 7/1995 | Van Gorcom et al. |
| 5,443,979 | A | 8/1995 | Vanderbeke et al. |
| 5,480,790 | A | 1/1996 | Tischer et al. |
| 5,492,821 | A | 2/1996 | Callstrom et al. |
| 5,516,525 | A | 5/1996 | Edwards, Jr. |
| 5,554,399 | A | 9/1996 | Vanderbeke et al. |
| 5,556,771 | A | 9/1996 | Shen et al. |
| 5,593,963 | A | 1/1997 | Van Ooijen et al. |
| 5,612,055 | A | 3/1997 | Bedford et al. |
| 5,691,154 | A | 11/1997 | Callstrom et al. |
| 5,716,655 | A | 2/1998 | Hamstra et al. |
| 5,736,625 | A | 4/1998 | Callstrom et al. |
| 5,780,292 | A | 7/1998 | Nevalainen et al. |
| 5,827,709 | A | 10/1998 | Barendse et al. |
| 5,830,696 | A | 11/1998 | Short |
| 5,830,733 | A | 11/1998 | Nevalainen et al. |
| 5,834,286 | A | 11/1998 | Nevalainen et al. |
| 5,853,779 | A | 12/1998 | Takebe et al. |
| 5,863,533 | A | 1/1999 | Van Gorcom et al. |
| 5,876,997 | A | 3/1999 | Kretz |
| 5,891,708 | A | 4/1999 | Saniez et al. |
| 5,900,525 | A | 5/1999 | Austin-Phillips et al. |
| 5,902,615 | A | 5/1999 | Saniez et al. |
| 5,935,624 | A | 8/1999 | DeLuca et al. |
| 5,955,448 | A | 9/1999 | Colaco et al. |
| 5,972,669 | A | 10/1999 | Harz et al. |
| 5,985,605 | A | 11/1999 | Cheng et al. |
| 5,989,600 | A | 11/1999 | Nielsen et al. |
| 6,022,555 | A | 2/2000 | DeLuca et al. |
| 6,039,942 | A | 3/2000 | Lassen et al. |
| 6,063,431 | A | 5/2000 | Bae et al. |
| 6,083,541 | A | 7/2000 | Hamstra et al. |
| 6,110,719 | A | 8/2000 | Kretz |
| 6,139,892 | A | 10/2000 | Fredlund et al. |
| 6,139,902 | A | 10/2000 | Kondo et al. |
| 6,140,077 | A | 10/2000 | Nakamura et al. |
| 6,183,740 | B1 | 2/2001 | Short et al. |
| 6,190,897 | B1 | 2/2001 | Kretz |
| 6,204,012 | B1 | 3/2001 | Hellmuth et al. |
| 6,248,938 | B1 | 6/2001 | Austin-Phillips et al. |
| 6,261,592 | B1 | 7/2001 | Nagashima et al. |
| 6,264,946 | B1 | 7/2001 | Müllertz et al. |
| 6,274,178 | B1 | 8/2001 | Beven et al. |
| 6,277,623 | B1 | 8/2001 | Oh et al. |
| 6,284,502 | B1 | 9/2001 | Maenz et al. |
| 6,291,221 | B1 | 9/2001 | Van Loon et al. |
| 6,309,870 | B1 | 10/2001 | Kondo et al. |
| 6,350,602 | B1 | 2/2002 | Van Gorcom et al. |
| 6,391,605 | B1 | 5/2002 | Kostrewa et al. |
| 6,451,572 | B1 | 9/2002 | Lei |
| 6,475,762 | B1 | 11/2002 | Stafford et al. |
| 6,511,699 | B1 | 1/2003 | Lei |
| 6,514,495 | B1 | 2/2003 | Svendsen et al. |
| 6,599,735 | B1 | 7/2003 | Bartok et al. |
| 6,720,014 | B1 | 4/2004 | Short et al. |
| 6,720,174 | B1 | 4/2004 | Lehmann |
| 6,841,370 | B1 | 1/2005 | Lei |
| 6,974,690 | B2 | 12/2005 | Lei |
| 7,022,371 | B2 | 4/2006 | Stafford et al. |
| 7,026,150 | B2 | 4/2006 | Lei |
| 7,078,035 | B2 | 7/2006 | Short et al. |
| 7,300,781 | B2 | 11/2007 | Lei |
| 7,309,505 | B2 | 12/2007 | Lei et al. |
| 7,312,063 | B2 | 12/2007 | Lei |
| 7,320,867 | B2 | 1/2008 | Suda et al. |
| 7,736,680 | B2 | 6/2010 | Lei et al. |
| 7,829,318 | B2 | 11/2010 | Lei |
| 7,833,743 | B2 | 11/2010 | Webel et al. |
| 2001/0018197 | A1 | 8/2001 | Wong et al. |
| 2001/0029042 | A1 | 10/2001 | Fouache et al. |
| 2002/0068350 | A1 | 6/2002 | Kondo et al. |
| 2002/0102692 | A1 | 8/2002 | Lei |
| 2002/0127218 | A1 | 9/2002 | Svendsen et al. |
| 2002/0136754 | A1 | 9/2002 | Short et al. |
| 2002/0192791 | A1 | 12/2002 | Lei |
| 2003/0072844 | A1 | 4/2003 | Lei |
| 2003/0092155 | A1 | 5/2003 | Kostrewa et al. |
| 2003/0206913 | A1 | 11/2003 | Webel et al. |
| 2004/0126844 | A1 | 7/2004 | Lei et al. |
| 2005/0095691 | A1 | 5/2005 | Lei |
| 2006/0153902 | A1 | 7/2006 | Lei |
| 2007/0196449 | A1 | 8/2007 | Lei |
| 2007/0218111 | A1 * | 9/2007 | Ehrenkranz et al. .......... 424/439 |
| 2008/0227150 | A1 | 9/2008 | Lei |
| 2009/0028994 | A1 | 1/2009 | Lei et al. |
| 2009/0074909 | A1 | 3/2009 | Webel et al. |
| 2009/0155237 | A1 | 6/2009 | Lei |
| 2010/0068335 | A1 | 3/2010 | Lei |

FOREIGN PATENT DOCUMENTS

| | | |
|---|---|---|
| EP | 0 420 358 A1 | 4/1991 |
| EP | 0 449 376 A2 | 10/1991 |
| EP | 0 556 883 A1 | 8/1993 |
| EP | 0 649 600 A1 | 4/1995 |
| EP | 0 684 313 A2 | 11/1995 |
| EP | 0 699 762 A2 | 3/1996 |
| EP | 0 772 978 B1 | 5/1997 |
| EP | 0 779 037 A1 | 6/1997 |
| EP | 0 897 010 A2 | 2/1999 |
| EP | 0 897 985 A2 | 2/1999 |
| EP | 0 909 821 A2 | 4/1999 |
| EP | 0 925 723 A1 | 6/1999 |
| EP | 0 955 362 A1 | 11/1999 |
| EP | 0 960 934 A1 | 12/1999 |
| GB | 2 286 396 A | 8/1995 |
| GB | 2 316 082 A | 2/1998 |
| JP | 10-276789 | 10/1998 |
| JP | 2001-292789 | 10/2001 |
| RU | 2 113 468 C1 | 6/1998 |
| WO | WO 86/01179 A1 | 2/1986 |
| WO | WO 90/03431 A1 | 4/1990 |
| WO | WO 90/05182 | 5/1990 |
| WO | WO 91/05053 | 4/1991 |
| WO | WO 91/14773 | 10/1991 |
| WO | WO 91/14782 | 10/1991 |
| WO | WO 93/14645 | 8/1993 |
| WO | WO 93/16175 | 8/1993 |
| WO | WO 93/19759 | 10/1993 |
| WO | WO 94/03072 | 2/1994 |
| WO | WO 94/03612 | 2/1994 |
| WO | WO 97/16076 | 5/1997 |
| WO | WO 97/35017 | 9/1997 |
| WO | WO 97/39638 | 10/1997 |
| WO | WO 97/45009 | 12/1997 |
| WO | WO 97/48812 | 12/1997 |
| WO | WO 97/48813 | 12/1997 |
| WO | WO 98/05785 | 2/1998 |
| WO | WO 98/06856 | 2/1998 |
| WO | WO 98/20139 | 5/1998 |
| WO | WO 98/30681 | 7/1998 |
| WO | WO 98/44125 | 10/1998 |
| WO | WO 98/54980 | 12/1998 |
| WO | WO 99/08539 | 2/1999 |
| WO | WO 99/49022 A1 | 9/1999 |
| WO | WO 99/49740 | 10/1999 |
| WO | WO 00/10404 | 3/2000 |
| WO | WO 00/20569 | 4/2000 |
| WO | WO 00/41509 A3 | 7/2000 |
| WO | WO 00/43503 A1 | 7/2000 |
| WO | WO 00/47060 | 8/2000 |
| WO | WO 00/58481 A2 | 10/2000 |
| WO | WO 00/71728 A1 | 11/2000 |
| WO | WO 00/72700 A1 | 12/2000 |
| WO | WO 01/36607 A1 | 5/2001 |
| WO | WO 01/58275 A2 | 8/2001 |
| WO | WO 01/58276 A2 | 8/2001 |

OTHER PUBLICATIONS

University of Wisconsin, Dept. of Nutritional Sciences, list of faculty mentors, http://www.nutrisci.wisc.edu/FACULTYPAGES/IGPNSfaculty.html, Nov. 2007, printed on Feb. 7, 2011.*

Abstract W130, "Supplemental dietary phytase and strontium improves bone traits of weanling pigs fed a phosphorous-adequate diet," J Animal Sci 84(Suppl. 1):340-341), Jul. 9, 2006.*

Cromwell, J., Feedstuffs, 63:14-6 (1991). "Phytase appears to reduce phosphorus in feed, manure."

Gentile et al., J Anim Sci., 81:2751-7 (2003). "Effectiveness of an experimental consensus phytase in improving dietary phytate-phosphorus utilization by weanling pigs."

Lei et al., J Appl Anim Res.,17:97-112 (2000). "Nutritional benefits of phytase and dietary determinants of its efficacy."

Murry et al., J Anim Sci., 75:1284-91 (1997). "The effect of microbial phytase in a pearl millet-soybean meal diet on apparent digestibility and retention of nutrients, serum mineral concentration, and bone mineral density of nursery pigs."

Vohra et al., Proc Soc Exp Biol Med., 120:447-9 (1965). "Phytic acid-metal complexes."

Yi et al., J Anim Sci., 74:1601-11 (1996). "Effectiveness of Natuphos phytase in improving the bioavailabilities of phosphorus and other nutrients in soybean meal-based semipurified diets for young pigs."

Young et al., J Anim Sci., 71:2147-50 (1993). "Addition of microbial phytase to diets of young pigs."

Atlung et al., "Role of the Transcriptional Activator AppY in Regulation of the cyx appA Operon of Escherichia coli by Anaerobiosis, Phosphate Starvation, and Growth Phase," Journal of Bacteriology 176(17):5414-5422 (1994).

Belin et al., "A Pleiotropic Acid Phosphatase-Deficient Mutant of Escherichia coli Shows Premature Termination in the dsbA Gene. Use of dsbA::phoA Fusions to Localize a Structurally Important Domain in DsbA," Mol. Gen. Genet. 242:23-32 (1994).

Blondeau et al., "Development of High-Cell-Density Fermentation for Heterologous Interleukin 1β Production in Kluyveromyces lactis Controlled by the PHO5 Promoter," Appl Microbiol Biotechnol, 41:324-329 (1994).

Boctor et al., "Enhancement of the Stability of Thrombin by Polyols: Microcalorimetric Studies," J. Pharm. Pharmacol., 44:600-603 (1992).

Boer et al., "Characterization of Trichoderma reesei Cellobiohydrolase Cel7a Secreted from Pichia pastoris Using Two Different Promoters," Biotechnology and Bioengineering 69(5):486-494 (2000).

Brondsted et al., "Effect of Growth Conditions on Expression of the Acid Phosphatase (cyx-appA) Operon and the appY Gene, Which Encodes a Transcriptional Activator of Escherichia coli," J. of Bacteriology, 178(6):1556-1564 (1996).

Chiarugi et al., "Differential Role of Four Cysteines on the Activity of a Low $M_r$ Phosphotyrosine Protein Phosphatase," FEBS Letters 310(1):9-12 (1992).

Dassa et al., "Identification of the Gene appA for the Acid Phosphatase (pH Optimum 2.5) of Escherichia coli," Mol. Gen. Genet., 200:68-73 (1985).

Dassa et al., "The Complete Nucleotide Sequence of the Escherichia coli Gene appA Reveals Significant Homology Between pH 2.5 Acid Phosphatase and Glucose-1-Phosphatase," J. of Bacteriology, 172(9):5497-5500 (1990).

Divakaran et al., "In vitro Studies on the Interaction of Phytase with Trypsin and Amylase Extracted from Shrimp (Penaeus vannamei) Hepatopancreas," J. Agric. Food Chem. 46:4973-4976 (1998).

Greiner et al., "Purification and Characterization of Two Phytases from Escherichia coli," Archives of Biochemistry and Biophysics, 303:107-113 (1993).

Granovskii et al., "Expression of Hepatitis B Virus HBsAg Gene in Yeast Cells Under Control of Promotor Region of PHO5 Gene," Soviet Progress in Virology, 5:45-47 (1985).

Han et al., "Development of Phytase Overexpressing Microbes for Nutritional Use," Poster Presentation at Cornell University's Biotechnology Symposium, Ithaca, New York (Oct. 15, 1997).

Han et al., "Expression of an Aspergillus niger Phytase Gene (phyA) in Saccharomyces cerevisiae," Applied and Environ. Microbiol., 65(5):1915-1918 (1999).

Han et al., "Role of Glycosylation in the Functional Expression of an Aspergillus niger Phytase (phyA) in Pichia pastoris," Archives of Biochemistry and Biophysics, 364:83-90 (1999).

Jia et al., "Purification, Crystallization and Preliminary X-ray Analysis of the Escherichia coli Phytase," Acta Cryst. D54:647-649 (1998).

Kanai et al., "Recombinant Thermostable Cycloinulo-oligosaccharide Fructanotransferase Produced by Saccharomyces cerevisiae," Appl. Environ. Microbiol. 63(12):4956-4960 (1997).

Kerovuo et al., "Isolation, Characterization, Molecular Gene Cloning, and Sequencing of a Novel Phytase from Bacillus subtilis," Applied and Environmental Microbiology 64(6):2079-2085 (1998).

Kim et al., "Cloning of the Thermostable Phytase Gene (phy) from Bacillus sp. DS11 and its Overexpression in Escherichia coli," FEMS Microbiology Letters 162:185-191 (1998).

Konietzny et al., "Model Systems for Developing Detection Methods for Foods Deriving from Genetic Engineering," J. Food Composition and Analysis, 10:28-35 (1997).

Kumagai et al., "Conversion of Starch to Ethanol in a Recombinant Saccharomyces cerevisiae Strain Expressing Rice α-amylase from a Novel Pichia pastoris Alcohol Oxidase Promoter," Biotechnology 11:606-610 (1993).

Lei et al., "Biotechnological Developments of Effective Phytases for Mineral Nutrition and Environmental Protection," Appl. Microb. Biotech. 57(4):474-481 (2001).

Lim et al., "Crystal Structure of Escherichia coli Phytase and its Complex with Phytate," Nature Structural Biology 7(2): 108-113 (2000).

Lim et al., "Studies of Reaction Kinetics in Relation to the $T_g$' of Polymers in Frozen Model Systems," in Levine, eds., Water Relationships in Food, New York, NY:Plenum Press, pp. 103-122 (1991).

Lozano et al., "Influence of Polyhydroxylic Cosolvents on Papain Thermostability," Enzyme Microb. Technol., 15:868-873 (1993).

Lozano et al., "Effect of Polyols on α-Chymotrypsin Thermostability: A Mechanistic Analysis of the Enzyme Stabilization," J. Biotechnol., 35:9-18 (1994).

Maugenest et al., "Cloning and Characterization of cDNA Encoding a Maize Seedling Phytase," Biochem. J. 322:511-517 (1997).

Meldgaard et al., "Different Effects of N-Glycosylation on the Thermostability of Highly Homologous Bacterial (1,3-1,4)-β-Glucanases Secreted from Yeast," Microbiology 140(1):159-166 (1994).

Minamiguchi et al., "Secretive Expression of the Aspergillus aculeatus Cellulase (FI-CM Case) by Saccharomyces cerevisiae," J. Fermentation and Bioengineering, 79(4):363-366 (1995).

Moore et al., "Molecular Cloning, Expression and Evaluation of Phosphohydrolases for Phytate-Degrading Activity," Journal of Industrial Microbiology, 14:396-402 (1995).

Murray et al., "Construction of Artificial Chromosomes in Yeast," Nature 305:189-193 (1983).

Ostanin et al., "Overexpression, Site-Directed Mutagenesis, and Mechanism of Escherichia coli Acid Phosphatase," J. of Biol. Chem., 267(32):22830-22836 (1992).

Ostanin et al., "Asp$^{304}$ of Escherichia coli Acid Phosphatase is Involved in Leaving Group Protonation," J. of Biol. Chem., 268(28):20778-20784 (1993).

Phillippy et al., "Expression of an Aspergillus niger Phytase (phyA) in Escherichia coli," J. Agric. Food Chem. 45(8):3337-3342 (1997).

Piddington et al., "The Cloning and Sequencing of the Genes Encoding Phytase (phy) and pH 2.5-Optimum Acid Phosphatase (aph) From Aspergillus niger var. awamori," Gene, 133:55-62 (1993).

Rodriguez et al., "Different Sensitivity of Recombinant Aspergillus niger Phytase (r-PhyA) and Escherichia coli pH 2.5 Acid Phosphatase (r-AppA) to Trypsin and Pepsin In vitro," Archives of Biochemistry and Biophysics 365(2):262-267 (1999).

Rodriguez et al., "Cloning, Sequencing, and Expression of an Escherichia coli Acid Phosphatase/Phytase Gene (appA2) Isolated from Pig Colon," Biochemical and Biophysical Research Communications, 257:117-123 (1999).

Rodriguez et al., "Site-Directed Mutagenesis Improves Catalytic Efficiency and Thermostability of Escherichia coli pH 2.5 Acid Phosphatase/Phytase Expressed in Pichia pastoris," Archives of Biochemistry and Biophysics 382(1):105-112 (2000).

Rossi et al., "Stabilization of the Restriction Enzyme EcoRI Dried with Trehalose and Other Selected Glass-Forming Solutes," Biotechnol. Prog., 13:609-616 (1997).

Schebor et al., "Glassy State and Thermal Inactivation of Invertase and Lactase in Dried Amorphous Matrices," *Biotechnol. Prog.*, 13:857-863 (1997).

Sidhu et al., "Analysis of α-Factor Secretion Signals by Fusing with Acid Phosphatase of Yeast," *Gene*, 54:175-184 (1987).

Sun et al., "Expression of *Aspergillus niger* Phytase in Yeast *Saccharomyces cerevisiae* for Poultry Diet Supplementation," *Poultry Science* 76(Suppl. 1):5 (1997).

Takahashi et al., "Independent Production of Two Molecular Forms of a Recombinant *Rhizopus oryzae* Lipase by *KEX2*-Engineered Strains of *Saccharomyces cerevisiae*," *Applied Microbiol. Biotechnology*, 52(4):534-540 (1999).

Terashima et al., "The Roles of the N-Linked Carbohydrate Chain of Rice α-amylase in Thermostability and Enzyme Kinetics," *Eur. J. Biochem.* 226:249-254 (1994).

Touati et al., "Pleiotropic Mutations in *appR* Reduce pH 2.5 Acid Phosphatase Expression and Restore Succinate Utilisation in CRP-Deficient Strains of *Escherichia coli*," *Mol. Gen. Genet.* 202:257-264 (1986).

Tschopp et al., "Heterologous Gene Expression in Methylotrophic Yeast," *Biotechnology*, 18:305-322 (1991).

Van Hartingsveldt et al., "Cloning, Characterization and Overexpression of the Phytase-Encoding Gene (*phyA*) of *Aspergillus niger*," *Gene* 127:87-94 (1993).

Verwoerd et al., "Stable Accumulation of *Aspergillus niger* Phytase in Transgenic Tobacco Leaves," *Plant Physiol.*, 109:1199-1205(1995).

Wodzinski et al., "Phytase," *Advances in Applied Microbiology*, 42:263-302 (1996).

Wyss et al., "Biochemical Characterization of Fungal Phytases (*myo*-Inositol Hexakisphosphate Phosphohydrolases): Catalytic Properties," *Applied and Environmental Microbiology* 65(2):367-373 (1999).

Wyss et al., "Biophysical Characterization of Fungal Phytases (*myo*-Inositol Hexakisphosphate Phosphohydrolases): Molecular Size, Glycosylation Pattern, and Engineering of Proteolytic Resistance," *Applied and Environ. Microbiol.*, 65(2):359-366 (1999).

Yao et al., "Recombinant *Pichia pastoris* Overexpressing Bioactive Phytase," *Science in China Series C. Life Sciences*, 41(3):330-336 (1998).

Zvonok et al., "Construction of Versatile *Escherichia coli*-Yeast Shuttle Vectors for Promoter Testing in *Saccharomyces cerevisiae*," *Gene*, 66(2):313-318 (1988).

ATCC Catalog for Yeasts, 19$^{th}$ Edition (1995).

Database Accession No. B36733, corresponding to Greiner et al., Arch. Biochem. Biophys. 303:107-113 (1993).

Golovan et al., "Characterization and Overproduction of the *E. coli* appA Encoded Biofunctional Enzyme the Exhibits Both Phytase and Acid Phosphatase Activities," *Can. J. Microbiol.* 46:59-71 (2000).

Kostrewa et al., "Crystal Structure of *Aspergillus niger* pH 2.5 Acid Phosphatase at 2.4 Å Resolution," *J. Mol. Biol.* 288:965-974 (1999).

Kostrewa et al., "Crystal Structure of Phytase from *Aspergillus ficuum* at 2.5 Å Resolution," *Nat. Struct. Biol.* 4:185-190 (1997).

Leeson et al., "Efficacy of New Bacterial Phytase in Poultry Diets," *Can. J. Anim. Sci.* 80:527-528 (2000).

Lehmann et al., "Exchanging the Active Site Between Phytases for Altering the Functional Properties of the Enzyme," *Protein Sci.* 9(10):1866-1872 (2000).

Lehmann et al., "From DNA Sequence to Improved Functionality: Using Protein Sequence Comparisons to Rapidly Design a Thermostable Consensus Phytase," *Protein Eng.* 13(1):49-57 (2000).

Lei et al., "Calcium Level Affects the Efficacy of Supplemental Microbial Phytase in Corn-Soybean Meal Diets of Weanling Pigs," *J. Anim. Sci.* 72(1):139-143 (1994).

Lei et al., "Supplemental Microbial Phytase Improves Bioavailability of Dietary Zinc to Weanling Pigs," *J. Nutr.* 123:1117-1123 (1993).

Lei et al., "Supplementing Corn-Soybean Meal Diets with Microbial Phytase Linearly Improves Phytate Phosphorus Utilization by Weanling Pigs," *J. Anim. Sci.* 71:3359-3367 (1993).

Mitchell et al., "The Phytase Subfamily of Histidine Acid Phosphatases: Isolation of Genes for Two Novel Phytases from the Fungi *Aspergillus terreus* and *Myceliophthora thermophila*," *Microbiol.* 143:245-252 (1997).

Mullaney et al., "Advances in Phytase Research,"*Adv. Appl. Microbiol.* 47:157-199 (2000).

Mullaney et al., "Phytase Activity in *Aspergillus fumigatus* Isolates," *Biochem. Biophys. Res. Commun.* 275:759-763 (2000).

Mullaney et al., "Positive Identification of a Lambda gt11 Clone Containing a Region of Fungal Phytase Gene by Immunoprobe and Sequence Verification," *Appl. Microbiol. Biotechnol.* 35:611-614 (1991).

Mullaney et al., "Site-Directed Mutagenesis of *Aspergillus niger* NRRL 3135 Phytase at Residue 300 to Enhance Catalysis at pH 4.0," *Biochem. Biophys. Res. Commun.* 297(4):1016-1020 (2002).

Nielsen et al., "The Determinants of α-Amylase pH-Activity Profiles," *Protein Eng.* 14(7):505-512 (2001).

Pasamontes et al., "Gene Cloning, Purification, and Characterization of a Heat-Stable Phytase from the Fungus *Aspergillus fumigatus*," *Appl. Environ. Microbiol.* 63(5):1696-1700 (1997).

Rodriguez et al., "Expression of the *Aspergillus fumigatus* Phytase Gene in *Pichia pastoris* and Characterization of the Recombinant Enzyme," *Biochem. Biophys. Res. Commun.* 268:373-378 (2000).

Scott et al., "The Effect of Phosphorus, Phytase Enzyme, and Calcium on the Performance of Layers Fed Corn-Based Diets," *Poultry Sci.* 78:1742-1749 (1999).

Sebastian et al., "Apparent Digestibility of Protein and Amino Acids in Brioler Chickens Fed a Corn-Soybean Diet Supplemented with Microbial Phytase," *Poultry Sci.* 76:1760-1769 (1997).

Tomschy et al., "Active Site Residue 297 of *Aspergillus niger* Phytase Critically Affects the Catalytic Properties," *FEBS Lett.* 472(2-3):169-172 (2000).

Tomschy et al., "Engineering of Phytase for Improved Activity at Low pH," *Appl. Environ. Microbiol.* 68(4):1907-1913 (2002).

Tomschy et al., "Optimization of the Catalytic Properties of *Aspergillus fumigatus* Phytase Based on the Three-Dimensional Structure," *Protein Sci.* 9(7):1304-1311 (2000).

Ullah et al., "Cyclohexanedione Modification of Arginine at the Active Site of *Aspergillus ficuum* Phytase," *Biochem. Biophys. Res. Commun.* 178(1):45-53 (1991).

Ullah et al., "Extracellular Phytase (E.C. 3.1.3.8) from *Aspergillus ficuum* NRRL 3135: Purification and Characterization," *Prep. Biochem.* 17(1):63-91 (1987).

Van Dijck, P.W.M., "Chymosin and Phytase. Made by Genetic Engineering (No. 10 in a Series of Articles to Promote a Better Understanding of the Use of Genetic Engineering)," *J. Biotechnol.* 67:77-80 (1999).

Van Etten et al., "Covalent Structure, Disulfide Bonding, and Identification of Reactive Surface and Active Site Residues of Human Prostatic Acid Phosphatase," *J. Biol. Chem.* 266(4):2313-2319 (1991).

Yi et al., "Sites of Phytase Activity in the Gastrointestinal Tract of Young Pigs," *Anim. Feed Sci. Technol.* 61:361-368 (1996).

Ullah et al., "Differences in the Active Site Environment of *Aspergillus ficuum* Phytases," *Biochem. Biophys. Res. Comm.* 243:458-462 (1998).

Greiner et al., "Purification and Characterization of a Phytase from *Klebsiella terrigena*," *Archives of Biochemistry and Biophysics* 341 (2): 201-206 (1997).

Ullah, A.H.J., "*Aspergillus ficuum* Phytase: Partial Primary Structure, Substrate Selectivity, and Kinetic Characterization," *Preparative Biochemistry* 18(4): 459-471 (1988).

DSM Nutritional Products, Opposition Brief for European Patent No. EP 1-090-129 (10 pages) (Nov. 15, 2006).

Novozymes A/S, Opposition Brief for European Patent No. EP 1-090-129 (19 pages) (Nov. 2006).

Curry et al., "Expression and Secretion of a *Cellulomonas fimi* Exoglucanase in *Saccharomyces cerevisiae*," *Applied and Environmental Microbiology* 54(2):476-484 (1988).

Fierobe et al., "Overexpression and Characterization of *Aspergillus awamori* Wild-Type and Mutant Glucoamylase Secreted by the Methylotrophic Yeast *Pichia pastoris*: Comparison with Wild-Type Recombinant Glucoamylase Produced Using *Saccharomyces cerevisiae* and *Aspergillus niger* as Hosts," *Protein Expression and Purification* 9(2):159-170 (1997).

Olsen et al., "Improvement of Bacterial beta-Glucanase Thermostability by Glycosylation," *Journal of General Microbiology* 137(3):579-585 (1991).

Solovicova et al., "High-Yield Production of *Saccharomycopsis fibuligera* Glucoamylase in *Escherichia coli*, Refolding and Comparison of the Nonglycosylated and Glycosylated Enzyme Forms," *Biochemical and Biophysical Research Communications* 224:790-795 (1996).

Stahl et al., "A New Phytase Expressed in Yeast Effectively Improves the Bioavailability of Phytate Phosphorus to Weanling Pigs," *J. Anim. Sci.* 78:668-674 (2000).

Eisenthal et al., "The Thermal Behaviour of Enzyme Activity: Implications for Biotechnology," *Trends Biotech.* 24:289-292 (2006).

Garrett et al., "Enhancing the Thermal Tolerance and Gastric Performance of a Microbial Phytase for Use as a Phosphate-Mobilizing Monogastric-Feed Supplement," *Appl. Environ. Microbiol.* 70:3041-3046 (2004).

Gu et al., "Gene Cloning, Expression, and Characterization of a Novel Phytase from *Dickeya paradisiaca*," *Appl. Biochem. Biotechnol.* 157:113-123 (2009).

Kim et al., "Molecular Cloning of the Phytase Gene from *Citrobacter braakii* and Its Expression in *Saccharomyces cerevisiae*," *Biotechnology Letters* 28:33-38 (2006).

Lee et al., "Expression of *Escherichia coli* AppA2 Phytase in Four Yeast Systems," *Biotechnology Letters* 27:327-334 (2005).

Luo et al., "A Novel Phytase appA From *Citrobacter amalonaticus* CGMCC 1696: Gene Cloning and Overexpression in *Pichia pastoris*," *Curr. Microbiol.* 55:185-192 (2007).

Makhatadze, "Measuring Protein Thermostability by Differential Scanning Calorimetry," *Curr. Prot. Sci.* 7.9.1-7.9.14 (1998).

Reply of Novozyme A/S, Appeal No. T0777/09-3.3.08 for European Patent No. EP 1-090-129 (8 pages) (Nov. 2009).

Grounds of Appeal of Novozyme A/S, Appeal No. T0777/09-3.3.08 for European Patent No. EP 1-090-129 (19 pages) (Jun. 2009).

Response to Appeal Brief for European Patent No. EP 1-090-129 (29 pages) (Jan. 12, 2010).

Shao et al., "Cloning, Expression, and Characterization of a New Phytase From the Phytopathogenic Bacterium *Pectobacterium wasabiae* DSMZ 18074," *J. Microbiol. Biotechnol.* 18:1221-1226 (2008).

Shi et al., "A Novel Phytase Gene *appA* from *Buttiauxella* sp. GC21 Isolated From Grass Carp Intestine," *Aquaculture* 275:70-75 (2008).

Spink, "Differential Scanning Calorimetry," *Methods in Cell Biology* 84:115-141 (2008).

Wyss et al., "Comparison of the Thermostability Properties of Three Acid Phosphatases from Molds: *Aspergillus fumigatus* Phytase, *A. niger* Phytase, and *A. niger* pH 2.5 Acid Phosphatase," *Appl. Environ. Microbiol.* 64:4446-4451 (1998).

Zale et al., "On the Role of Reversible Denaturation (Unfolding) in the Irreversible Thermal Inactivation of Enzymes," *Biotechnology and Bioengineering* XXV:2221-2230 (1983).

Response to Official Communication of Notices of Opposition, Opposition Against European Patent No. 1090129 (29 pages) (Aug. 31, 2007).

Summons to Attend Oral Proceeding Pursuant to Rule 115(1)EPC, Opposition Against European Patent No. 1090129 (7 pages) (Feb. 26, 2008).

Response to Summons to Attend Oral Proceedings, Opposition Against European Patent No. 1090129 (27 pages) (Nov. 14, 2008).

Response to Preliminary Opinion of Opposition Division, Opposition Against European Patent No. 1090129 (3 pages) (Nov. 11, 2008).

Grounds of Appeal of Cornell Research Foundation, Inc. for European Patent No. EP 1-090-129 (6 pages) (Jun. 23, 2009).

Haefner, S. et al., "Biotechnological Production and Applications of Phytases," *Appl. Micobiol. Biotechnol.* 68:588-597 (2005).

Response to Grounds of Appeal of Cornell Research Foundation, Inc. by Novozymes A/S for European Application No. EP 1090129/99935340.2 (11 pages) (Nov. 2, 2009).

Pagano et al., "Comparative Effects of Supplemental Phytase on Phytate-Phosphorus Release and Bone Development at Two Levels of Dietary Phosphorus," *FASEB J.* 18:A1306 (2004) (abstract only).

Pagano et al., "Supplemental Dietary Phytase Improves Growth and Bone Development of Young Pigs Fed a Phosphorus-Adequate Diet," *FASEB J.* 19:A984 (2005) (abstract only).

Roy et al., "Effects of Supplemental Dietary Phytase and Strontium on Bone Strength of Weanling Pigs Fed a High Phosphorus Diet," *J. Anim. Sci.* 84(Suppl.1):340 (2006) (abstract only).

Roy and Lei, "Dietary Supplementation of Phytase Enhanced Bone Density in Young Pigs Fed a High Phosphorus Diet," *FASEB J.* 21(5):A123 (2007) (abstract only).

Roy et al., "Effects of Supplemental Dietary Phytase and Strontium on Bone Strength of Weanling Pigs Fed a High Phosphorus Diet," Poster Presentation (Jul. 2006).

Pagano et al., "Supplemental Dietary Phytase and Strontium Improves Bone Traits of Weanling Pigs Fed a Phosphorus-Adequate Diet," Poster Presentation (Jul. 2006).

Hercz, "Regulation of Bone Remodeling: Impact of Novel Therapies," *Semin Dial.* 14(1):55-60 (2001) (abstract only).

Takeda et al., "Central Control of Bone Formation," *J. Bone Metab.* 19(3):195-8 (2001) (abstract only).

Jalal et al., "Effect of Supplementation of Two Different Sources of Phytase on Egg Production Parameters in Laying Hens and Nutrient Digestibility," *Poultry Science* 80:1463-1471 (2001).

Dassa et al., "The Acid Phosphatase with Optimum pH of 2.5 of *Escherichia coli*," *J. Biol. Chem.* 257:6669-6676 (1982).

Technical Examination Report for Brazilian Application No. PI9911549-2 (Jun. 18, 2010).

Technical Examination Report for Brazilian Application No. PI9911549-2 (Feb. 9, 2011).

Technical Examination Report for Brazilian Application No. PI0009516-8 (Jan. 11, 2010).

Technical Examination Report for Brazilian Application No. PI0009516-8 (Oct. 20, 2010).

Technical Examination Report for Brazilian Application No. PI0009516-8 (May 30, 2011).

European Examination Report for EP 00978762-3 (Mar. 2, 2010).

Lane et al., "A Review of Anabolic Therapies for Osteoporosis," *Arthritis Research and Therapy* 5:214-222 (2003).

Angel et al., "Phytic Acid Chemistry: Influence on Phytin-Phosphorus Availability and Phytase Efficacy," *J. Appl. Poult. Res.* 11:471-480 (2002).

* cited by examiner

SEQUENCE LISTING

<160> NUMBER OF SEQ ID NOS: 2

<210> SEQ ID NO 1
<211> LENGTH: 432
<212> TYPE: PRT
<213> ORGANISM: Escherichia coli

<400> SEQUENCE: 1

```
Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Lys Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
```

```
                260                 265                 270
Asn Ala Gln Phe Tyr Leu Leu Gln Arg Thr Pro Glu Val Ala Arg Ser
            275                 280                 285

Arg Ala Thr Pro Leu Leu Asp Leu Ile Lys Thr Ala Leu Thr Pro His
        290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Leu Ser Asp Asn Ser Gln
        355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 2
<211> LENGTH: 432
<212> TYPE: PRT
<213> ORGANISM: Escherichia coli

<400> SEQUENCE: 2

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Ser Gln Leu Asn Leu Cys Leu Asn Arg Glu Lys Gln Asp Glu
        195                 200                 205

Ser Cys Ser Leu Thr Gln Ala Leu Pro Ser Glu Leu Lys Val Ser Ala
```

-continued

```
            210                 215                 220
Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Tyr Leu Leu Gln Arg Thr Pro Glu Val Ala Arg Ser
                275                 280                 285

Arg Ala Thr Pro Leu Leu Asp Leu Ile Met Ala Ala Leu Thr Pro His
                290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Arg Leu Ser Asp Asn Ser Gln
                355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430
```

COMPOSITIONS AND METHODS FOR BONE STRENGTHENING

RELATED APPLICATIONS

This application claims priority under 35 U.S.C. 119(e) to U.S. Provisional Application Ser. No. 60/958,855, filed Jul. 9, 2007, the entirety of which is incorporated herein by reference.

FIELD OF THE INVENTION

The present invention relates to methods and compositions for strengthening bone and avoiding osteoporosis.

BACKGROUND OF THE INVENTION

As a primary concern for human health, bone fractures are associated with poor bone mineralization during growth spurts and increased risk of osteoporosis in the elderly[1,2]. Osteoporosis causes bone fractures by lowering bone mass and deteriorating bone architecture[3]. Hip fractures alone are estimated to reach >6 million cases a year by 2050[4]. While osteoporotic fractures occur mostly in people over the age of 70[5], enhancing peak bone mass early in life may postpone or prevent the incidents[6,7].

Osteoporosis is a major public health problem[49] afflicting at least 10 million people in the US[50]. Although a number of drugs are available to treat this disorder, most of these drugs act to only inhibit bone resorption[51,52,53]. Because bone metabolism depends on the balance between the osteoblasts-mediated formation and the osteoclasts-mediated resorption[54], effectiveness of these drugs is fairly limited in restoring bone integrity[55,56]. In contrast, maximizing bone mass and strength at an early stage of life offers the most effective strategy to prevent or alleviate osteoporosis at later life stages[57,58]. Nutritional manipulation is considered to be one of the major exogenous factors to enhance peak bone mass at early life stages[59,60,61].

Mostly, only surrogates are available for in vivo bone property and function assessments in humans[7]. Thus, animal models offer an advantage for the actual measurements of biophysical characteristics and chemical compositions of bones. Among several small and large animal models[8], canine and porcine bones resemble human bones in many features including density and stress fracture properties[9]. Because of implications of estrogen in the occurrence of osteoporosis for women[10] and similarities of the pig estrus cycle to the human menstrual cycle[11], pigs seem to be a better model than dogs for human osteoporosis research.

Microbial phytase has been widely used during the past decade as a feed additive for swine to enhance utilization of phytate-P from plant feeds[12]. Studies have shown effectiveness of the enzyme in replacing inorganic P supplementation to support normal growth performance and bone strength of pigs fed low-P diets[13,14]. The enzyme releases P and other chelated elements including Ca, Fe, Zn, Mn, and Cu for absorption in the gastrointestinal tract, allowing possible incorporations of these elements into bone[15,16]. A few experiments[17,18] have shown potential benefits of dietary phytase to bone properties in pigs fed P-adequate diets. Because these experiments were conducted to optimize growth and production responses of pigs, data on bone responses of pigs from these studies offered limited implications for human bone health issues.

SUMMARY OF THE INVENTION

The invention relates to the discovery that bone mechanical, chemical, and histological properties can be enhanced by administering supplemental strontium and phytase enzyme. Described herein are compositions comprising phytase enzyme, strontium and preferably both, and methods for their use for strengthening bone. The method is applicable to diverse species, including, for example, mammals, fish, and birds.

One aspect of the invention is directed to a method of improving bone structure and function in a mammal, the method comprising administering to the mammal strontium and a phytase enzyme. In one embodiment, strontium and phytase enzyme are administered along with ingestion of at least 0.1% phytate and intermediate metabolites in the diet or an oral equivalent.

Another aspect of the invention is directed to a method of improving bone structure and function, the method comprising administering supplemental inorganic phosphate and a phytase enzyme. Some embodiments of this aspect include application of the method to birds or mammals.

Another aspect of the invention is directed to an animal feed composition comprising a phytase enzyme. Included in this aspect are feed compositions with or without supplemental strontium.

Another aspect of the invention is directed to a method of treating or preventing osteoporosis in a subject, the method comprising administering to the subject a phytase enzyme and supplemental strontium. The supplemental strontium can be, e.g., about 100-fold lower dose than the typical treatment (i.e., about 3 mg/day per kg body weight, vs 350 mg/day/kg body weight).

Another aspect of the invention is directed to a dietary supplement composition for administration to a human, the composition comprising a phytase enzyme and supplemental strontium.

In one respect, the present invention related to the herein described compositions, methods, and respective component(s) thereof, as essential to the invention, yet open to the inclusion of unspecified elements, essential or not ("comprising"). In some embodiments, other elements can be included in the description of the composition, method or respective component thereof are limited to those that do not material affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

Th). Values are means of pigs (N=5), and bars with different letters (a vs b) indicate significant difference (P<0.05).

Figure 4A:
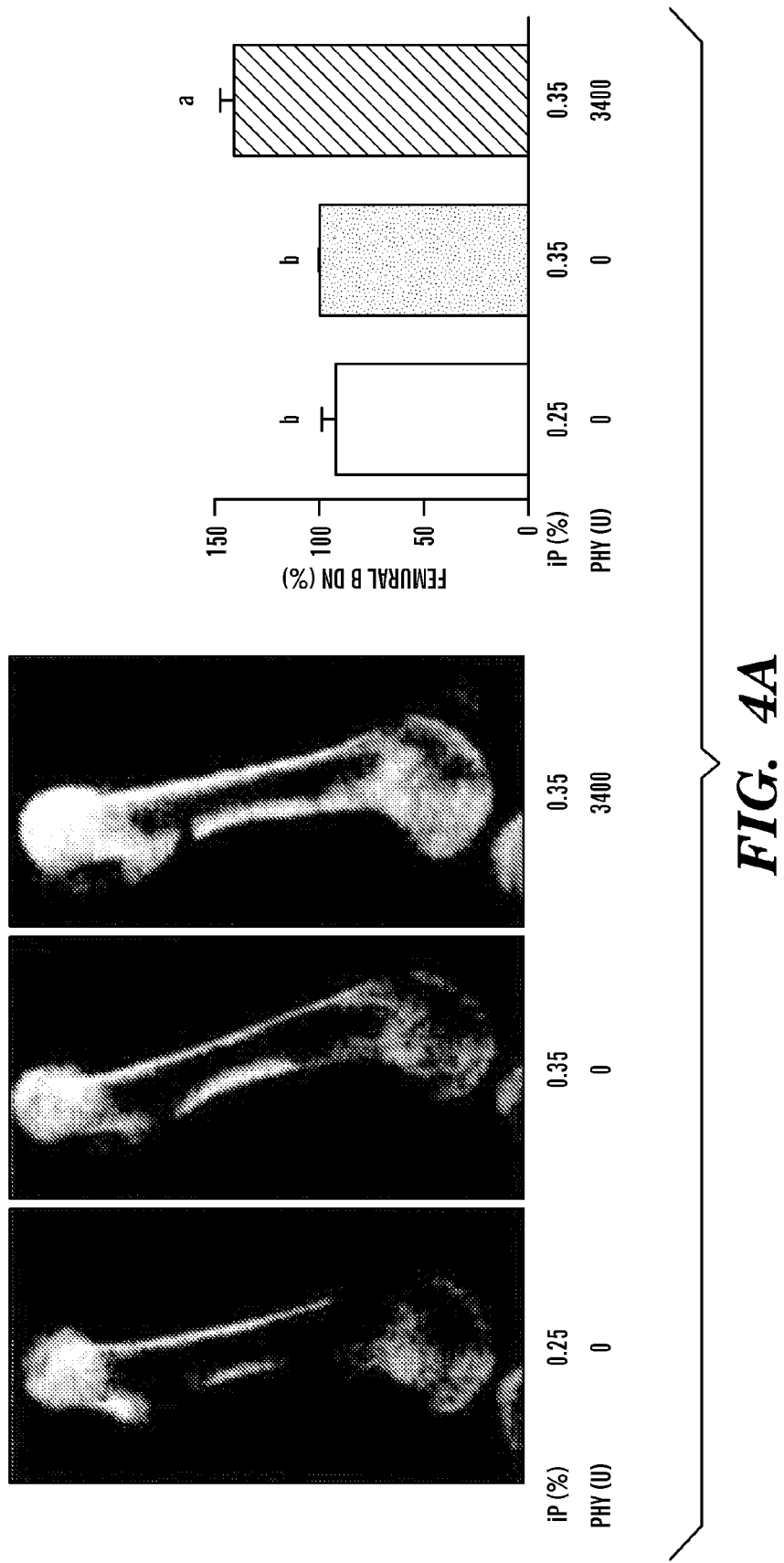
Figure 4B:
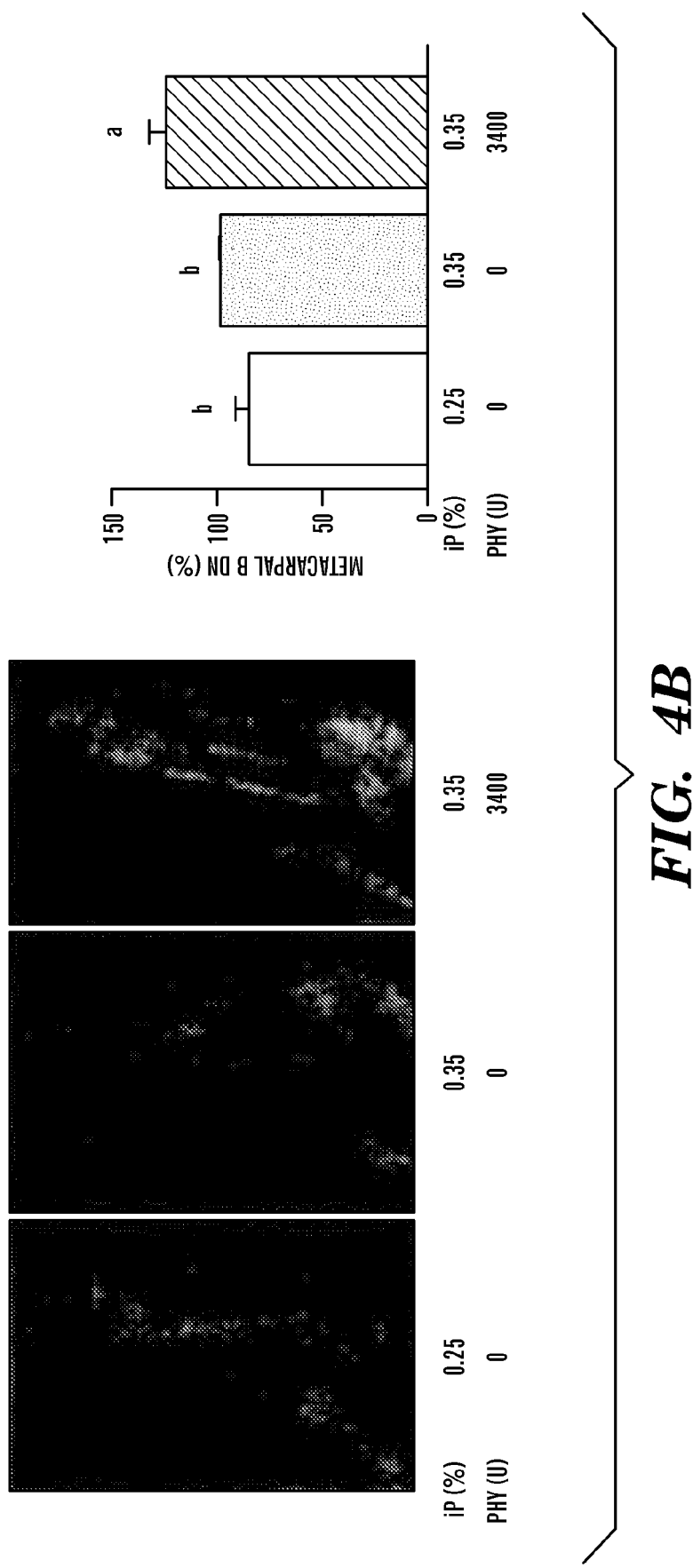
Figure 4C:
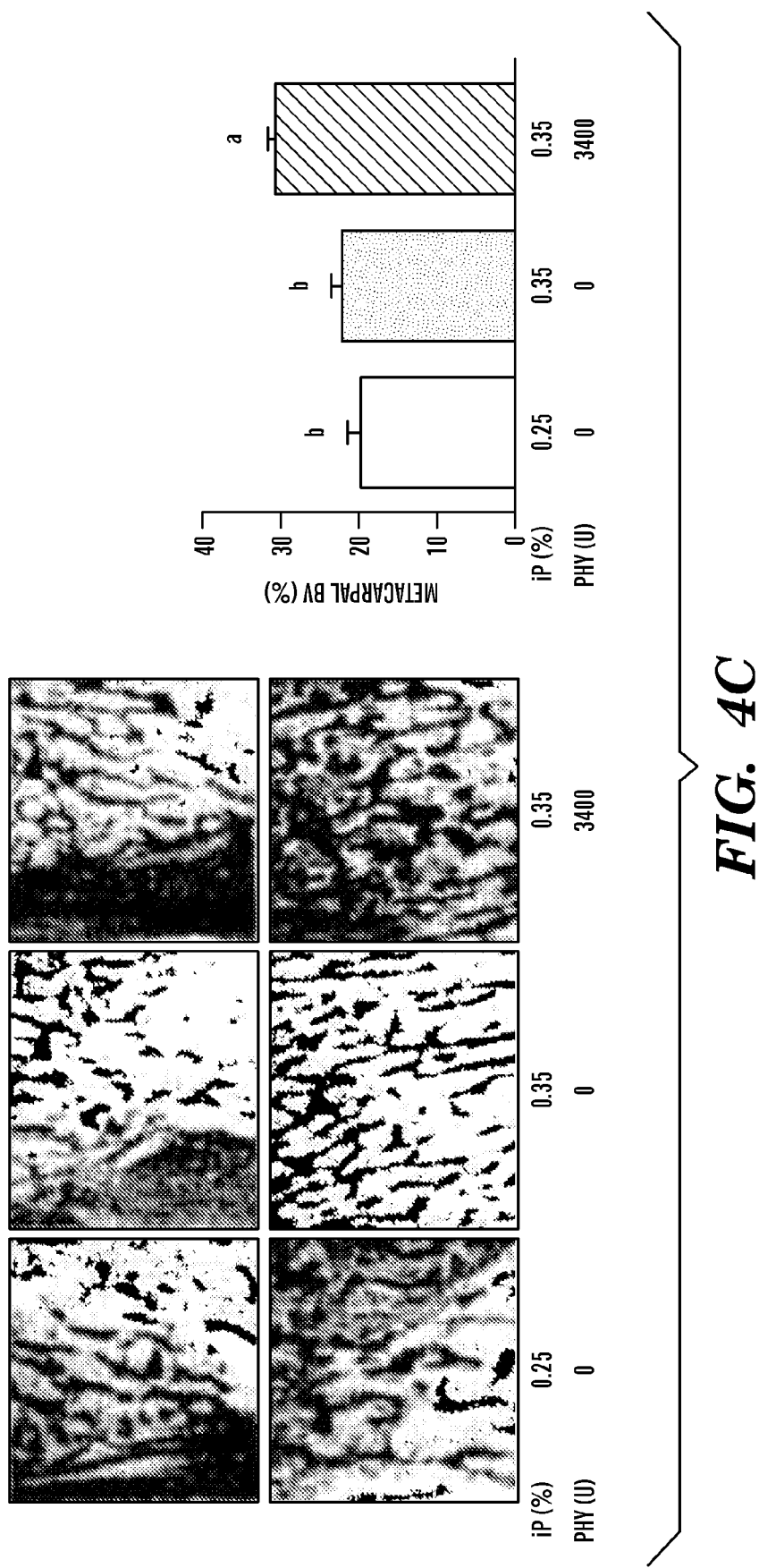

FIG. 4 shows the effects in pigs fed supplemental phytase: (A) a left femoral radiograph; (B) a left $4^{th}$ metacarpal radiograph; and (C) right metacarpal histology. In FIGS. 4A and 4B, a less opaque radiograph such as for the phytase-fed pig bones, indicates a greater bone density. The bar graphs on the right show the means (n=5) of pixel density of corresponding radiographs expressed as a relative percent of pixel density in specimens from the 0.35% iP diet group. FIG. 4C shows two locations of metacarpal histology. The top panel displays histology of bone density from the right legs of the same animals used to obtain the radiographs shown in FIG. 4B. Bones from the phytase-fed pigs show higher (P<0.05; n=5) bone density (black arrowhead). This was the transitional zone between cortical and cancellous bone. Sagittal sections were taken from between diaphyseal funnel zone and metaphyseal zone of metacarpal bone. The bottom panel displays histology of cancellous bone (black arrowheads) at the mid proximal diaphyseal region from the same metacarpal bone. The bar graph on the right represents mean (n=5) of total metacarpal bone volume (BV). In all three bar graphs, means with different letters (a vs b) indicated a significant difference (P<0.05; n=5). Massion's trichrome method.

FIG. 5 shows the effects of supplemental phytase on bone mineral content: (A) Effects of supplemental phytase on femoral (left) and metacarpal (right) cortical (Ct, top) and cancellous (Cn, bottom) bone ash. The total mineral concentrations were measured from the same bone samples used for the radiographs shown in FIG. 4. Means with different letters (a vs b) indicate a significant difference (P<0.05; n=5). Massion's trichrome method. (B) Histological displays bone mineralization in the $4^{th}$ metacarpus of the right leg from the same pigs used for the radiograph shown in FIG. 4B. In comparisons with those fed no phytase, pigs fed phytase had an increased mineralized matrix (red color: black arrowheads) in the zone of hypertrophic cartilage (Z. Hp) at metacarpal growth plate. (C) Representative sections from the middle and of the growth plate (and lower) show greater trabecular bone mineralization (black arrowheads) due to phytase supplementation from the same metacarpus used in FIG. 4C. Very active oseoblasts (white arrowheads) indicate a cancellous bone forming zone. The box marked area is magnified in the inset. Modified tetrachrome method.

Figure 6A:
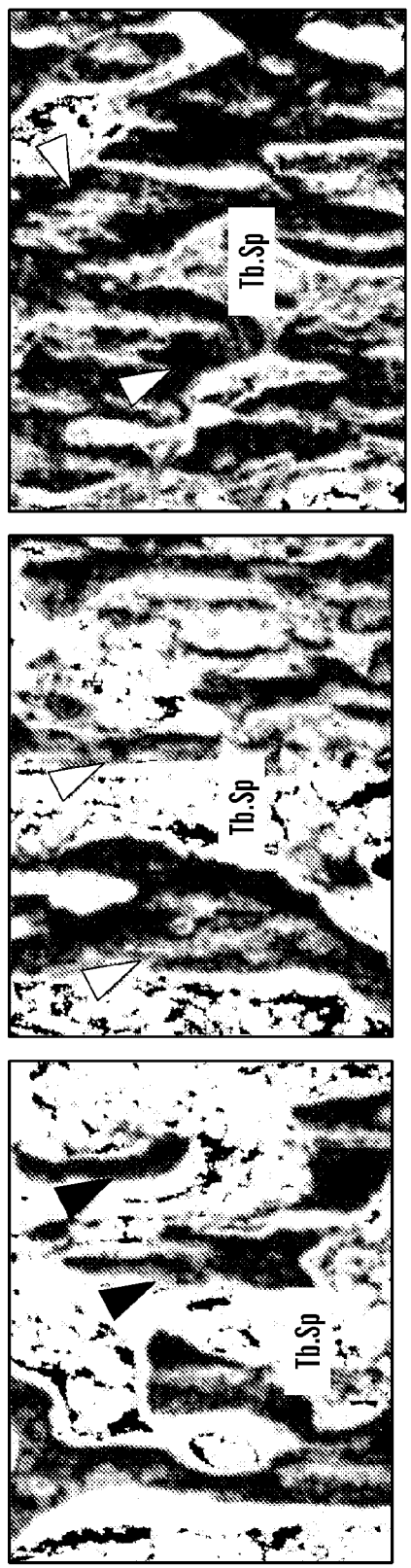

FIG. 6 shows the effects of supplemental phytase on: (A) trabecular bone density (Tb Dn), trabecular thickness (Tb Th), and trabecular separation (Tb Sp); (B) Osteiod and (C) sulfated proteoglycans (S Pg) of metacarpal bone. The data in the bottom of each of the figures represent the quantification of histomorphometry of serial sections of replicate samples expressed as mean±SEM (n=5). Means with different letters (a vs b) differ (P<0.05). FIG. 6A shows representative sections from the mid-section region just cranial to the growth plate of metacarpal bones. Phytase supplementation increased trabecular thickness and number, but decreased trabecular separation, resulting in enhanced trabecular connectivity or cancellous bone density.

Figure 6B:
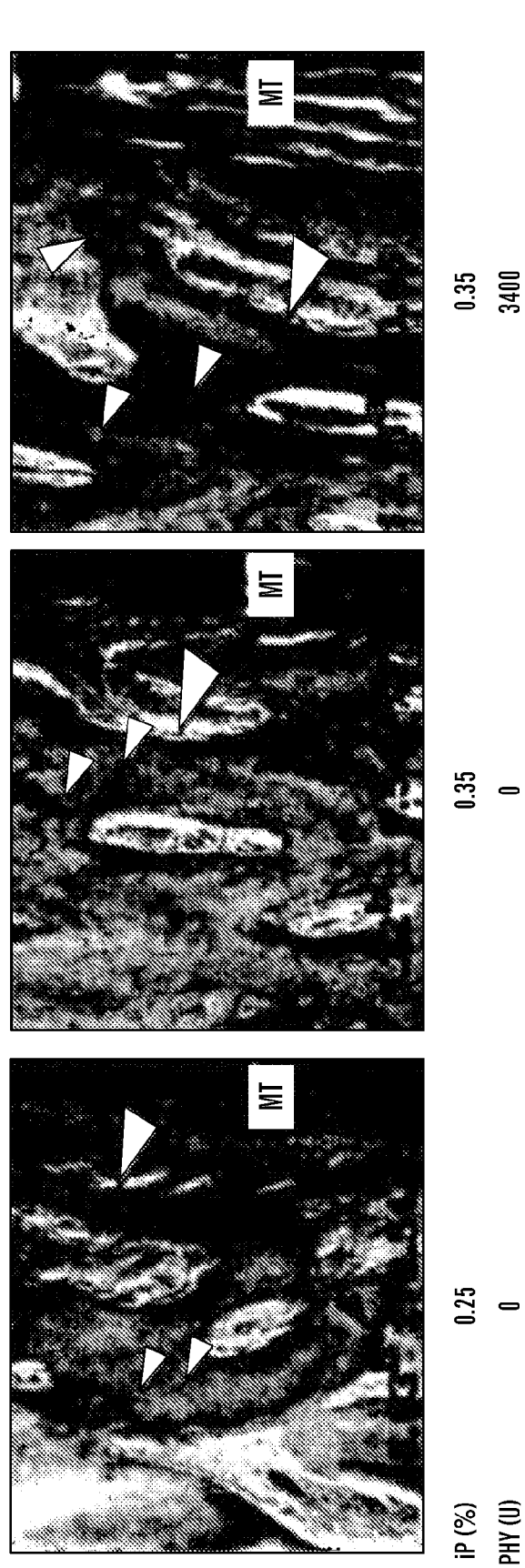
Figure 6C:
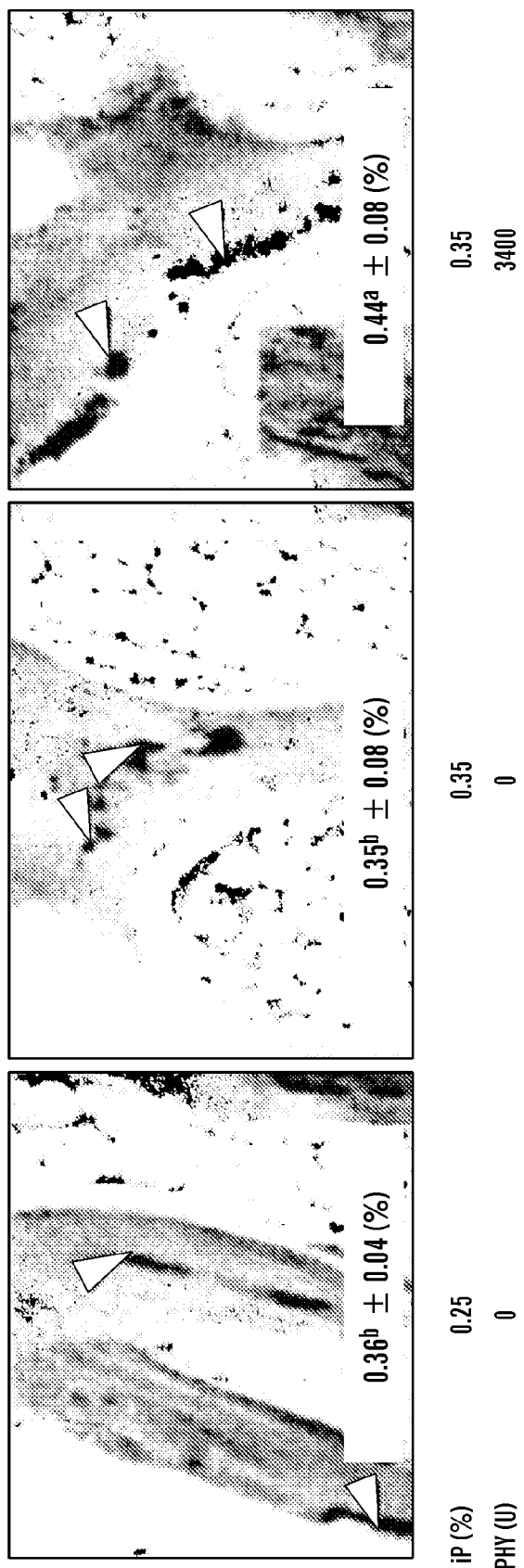

Massion's trichrome method. FIG. 6B shows osteoid (black arrowhead), osteoblasts/osteocytes (big white arrowhead), mesenchymal tissue (MT), and bone (red color) containing many connecting osteocytes (small white arrowheads). Note that osteoid thickness was increased (P<0.05; n=5) by phytase supplementation. Masson's trichrome method. FIG. 6C depicts quantitative and qualitative status of sulfated proteoglycans (black arrowheads) in cancellous bone. Proteoglycans appeared to be both uniformly distributed (shown in inset), scattered, crystal shaped, and highly dense in bones of pigs fed phytase, whereas proteoglycans were more uniformly distributed in collagen fibers in bones of pigs fed no phytase. High levels of proteoglycans suggest a potential role of phytase in promoting the synthesis of the compound during enchondral bone formation. Alcian blue method, counterstaining with haematoxylin.

DETAILED DESCRIPTION OF THE INVENTION

In one aspect, the invention is directed to a method of improving bone structure and function, including increasing bone strength, in a mammal, the method comprising administering to the mammal strontium and a phytase enzyme. In this and other aspects described herein, the phytase enzyme can be, for example, a microbial phytase or a plant phytase. The microbial phytase enzyme can comprise, for example, a fungal phytase or a bacterial phytase. Phytases useful in the methods and compositions described herein can be derived from natural sources or can be produced, e.g., recombinantly.

Bacterial phytases useful in the methods and compositions described herein can include, for example, an *E. coli* phytase or an *Aspergillus niger* phytase. Thus, for example, the bacterial phytase can be an *E. coli* AppA phytase or an *A. niger* PhyA phytase.

The *E. coli* AppA phytase useful in this and other aspects described herein can be AppA phytase or AppA2 phytase e.g., or a mutant thereof as described herein.

In this and other aspects described herein, the phytase can be administered by feeding a feed composition comprising the phytase to the mammal. Similarly, in this and other aspects described herein, the strontium can be administered by feeding a feed composition supplemented with strontium to the mammal. Strontium occurs naturally in feed and food at approximately 5-8 mg/kg.

In this and other aspects described herein, a feed composition comprising phytase further comprises supplemental strontium.

The phytase can be present in a feed composition at, e.g., at least 1000 U/kg, at least 2000 U/kg of feed or more. The supplemental strontium can be present at, e.g., at least 25 mg/kg of feed, at least 50 mg/kg of feed, or more. Where human administration is concerned, the dosage of phytase (in Units) or supplemental strontium (in milligrams) can be expressed as dose per 70 kg of body weight, based on the weight of an average adult. Thus, the phytase can be administered at least 50 U/70 kg body weight, at least 100 U/70 kg body weight, at least 150 U/70 kg body weight, at least 200 U/70 kg body weight, at least 300 U/70 kg body weight, at least 500 U/70 kg body weight, at least 700 U/70 kg body weight, at least 900 U/70 kg body weight, at least 1000 U/70 kg body weight, at least 1500 U/70 kg body weight, at least 2000 U/70 kg body weight, at least 2500 U/70 kg body weight, at least 3000 U/70 kg body weight, at least 3500 U/70 kg body weight, at least 4000 U/70 kg body weight, at least 4500 U/70 kg body weight, at least 5000 U/70 kg body weight, at least 5500 U/70 kg body weight, at least 6000 U/70 kg body weight, etc., to about 20,000 U/70 kg body weight or more. These dosages are preferably further considered as a daily dosage, e.g., using phytase dosage as an example, at least 50 U/70 kg body weight/day, at least 100 U/70 kg body weight/day, etc., although it should be understood that the daily dosage may be administered in one, two, three or more doses per day of equal or unequal size, up to a given daily dosage. Supplemental strontium dosages for human administration can be expressed similarly based on milligrams per 70 kg body weight per day.

In this and other aspects described herein, the mammal can be selected from, e.g., dogs, cats, horses, cattle, sheep, goats and humans. Other species include fish, poultry and zoo animals.

In another aspect, the invention is directed to an animal feed composition comprising a phytase enzyme and supplemental strontium. The phytase can be present in a feed composition at, e.g., at least 1000 U/kg of feed, at least 2000 U/kg of feed, or more. The supplemental strontium can be present at, e.g., at least 2.5-5 mg/kg of feed, at least 10 mg/kg of feed, at least 15 mg/kg of feed, at least 20 mg/kg of feed, at least 25 mg/kg of feed, at least 50 mg/kg of feed, or more (but being mindful of toxic thresholds for strontium in a given animal). As above, where human administration is concerned, the dosage of phytase (in Units) or supplemental strontium (in milligrams) can be expressed as dose per 70 kg of body weight, based on the weight of an average adult. Dosages of the phytase and supplemental strontium for human administration in a dietary supplement composition are as described two paragraphs earlier and elsewhere herein.

In another aspect, the invention is directed to a method of treating or preventing osteoporosis in a subject, the method comprising administering to said individual a phytase enzyme and strontium. The phytase can be administered orally as a dietary supplement, as can be the strontium. In one embodiment, the phytase and strontium can be administered orally in a single dietary supplement composition.

In another aspect, the invention is directed to a dietary supplement composition for administration to a human, the composition comprising a phytase enzyme and supplemental strontium. In this aspect, the dietary supplement composition can comprise phytase enzyme at a level of about 0.1% to about 90% by weight.

As used above, and throughout the description of the present invention, the following terms, unless otherwise indicated, shall be understood to have the following meanings.

As used herein, the term "AppA phytase" refers to a phytase enzyme having the sequence of App A phytase described by Dassa et al., 1990, J. Bacteriol. 172:5497-5500 (incorporated herein by reference) or described by Rodriguez et al., 1999, Biophys Biochem Res. Commun. 257:117-123 (incorporated herein by reference), or a conservative amino acid substitution mutant thereof that retains phytase activity. Specifically encompassed by the term "AppA phytase" are the enzymatically active AppA phytase and phytase mutants described in U.S. Pat. No. 6,841,370, U.S. Pat. No. 6,451,572, U.S. Pat. No. 6,974,690 and U.S. Pat. No. 6,511,699, U.S. Pat. No. 5,876,997, U.S. Pat. No. 6,110,719, U.S. Pat. No. 6,190,897, U.S. Pat. No. 6,183,740, U.S. Pat. No. 6,720,014, U.S. Pat. No. 6,855,365, U.S. Pat. No. 7,078,035, U.S. Pat. No. 7,232,677, U.S. Pat. No. 7,135,323, and U.S. Pat. No. 7,138,260, each of which is incorporated herein in its entirety by reference.

The term "retains phytase activity" means that a given phytase enzyme has at least 80% of the phytase activity of the E. coli AppA phytase of SEQ ID NO: 1 or SEQ ID NO: 2 when tested according to the method described by Piddington et al., 1993, Gene 133: 56-62, which is incorporated herein by reference. In various embodiments, a phytase enzyme has at least 90%, at least 100% or more, e.g., at least 110%, 120%, 150%, 2-fold, 3-fold, 5-fold or more of the phytase activity of the E. coli phytase of SEQ ID NO: 1 or SEQ ID NO: 2.

As used herein, the term "adequate dietary phosphorus" means the amount of dietary phosphorus necessary to maintain good health and physiological function dependent upon phosphorus. The amount of dietary phosphorus required to maintain good health varies with age in humans and animals. In general, however, a dietary available phosphorus content of about 0.33% by weight is considered adequate dietary phosphorus in pigs.

Estimated average dietary phosphorus requirements for respective age groups in humans are set out in the following tables (excerpted from the National Health and Medical Research Council of the Australian government and the Ministry of Health of New Zealand). An individual receiving phosphorus at or above the adequate intake or average requirement is considered to be receiving adequate dietary phosphorus as the term is used herein.

Infants:

| Age | Adequate intake |
| --- | --- |
| 0-6 months | 100 mg/day |
| 7-12 months | 275 mg/day |

To arrive at the figures for 0-6 months, the average intake of breast milk (0.78 L/day) was multiplied by the average concentration of phosphorus in breast milk (124 mg/L) from 10 studies reviewed by Atkinson et al[95], and rounding. The adequate intake for 7-12 months was set by adding an estimate for phosphorus from breast milk at this age to an estimate of intake from supplementary foods. A breast milk volume of 0.60 L/day[96,97] and the average concentration of phosphorus in breast milk at this age 124 mg/L[95] give a contribution of 75 mg phosphorus/day from breast milk that is added to 200 mg/day from complementary foods[98].

Children & Adolescents:

| Age | Estimated average requirement | Recommended dietary intake |
| --- | --- | --- |
| All | | |
| 1-3 yr | 380 mg/day | 460 mg/day |
| 4-8 yr | 405 mg/day | 500 mg/day |
| Boys | | |
| 9-13 yr | 1,055 mg/day | 1,250 mg/day |
| 14-18 yr | 1,055 mg/day | 1,250 mg/day |
| Girls | | |
| 9-13 yr | 1,055 mg/day | 1,250 mg/day |
| 14-18 yr | 1,055 mg/day | 1,250 mg/day |

To arrive at these figures in the absence of data on serum Pi or phosphorus balance in children from 1-8 years, estimation of body accretion for these age groups was used on known tissue composition and growth rates[99] using a conservative estimate of phosphorus absorption of 70%. The equation used was Estimated Average Requirement=(accretion+urinary loss) divided by fractional absorption. This gave an Estimated Average Requirement of 380 mg for children aged 1-3 years which, with an assumed Coefficient of Variation of 10% for the Estimated Average Requirement and rounding, gives a Recommended Dietary Intake of 460 mg/day. For children aged 4-8 years, the Estimated Average Requirement and the Recommended Dietary Intake were estimated to be 405 mg/day and 500 mg/day, respectively. For 9-13 year olds, longitudinal data and a large cross-sectional database[100] allowed estimation of phosphorus requirement from tissue accretion data using a factorial approach that was then also adopted for the 14-8-year-olds. The Estimated Average Requirement for both age groups was set at 1,055 mg/day.

Assuming a Coefficient of Variation of 10% for the Estimated Average Requirement and rounding gave a Recommended Dietary Intake of 1,250 mg.

Adults:

| Age | Estimated average requirement | Recommended dietary intake |
|---|---|---|
| Men | | |
| 19-30 yr | 580 mg/day | 1,000 mg/day |
| 31-50 yr | 580 mg/day | 1,000 mg/day |
| 51-70 yr | 580 mg/day | 1,000 mg/day |
| >70 yr | 580 mg/day | 1,000 mg/day |
| Women | | |
| 19-30 yr | 580 mg/day | 1,000 mg/day |
| 31-50 yr | 580 mg/day | 1,000 mg/day |
| 51-70 yr | 580 mg/day | 1,000 mg/day |
| >70 yr | 580 mg/day | 1,000 mg/day |

To arrive at these figures, a graphical transformation technique was used[101], the Estimated Average Requirement for adults was based on average dietary intake of phosphorus required from a typical mixed diet to reach the lowest point of the normal range for serum Pi[102,103]. The estimates assume an absorption efficiency of 62.5%[104,105,106]. By definition, at this level of intake, only half the population will achieve a Pi above the bottom of the normal range. A Coefficient of Variation of 35% for the Estimated Average Requirement was derived from consideration of the increase in ingested intake required to raise serum Pi from the bottom end of the normal range to a level of 3.1 mg/dL (1 mmol/L), the fasting level attained by most well nourished adults[102,103] giving a Recommended Dietary Intake of 1,000 mg.

Pregnancy:

| Age | Estimated average requirement | Recommended dietary intake |
|---|---|---|
| 14-18 yr | 1,055 mg/day | 1,250 mg/day |
| 19-30 yr | 580 mg/day | 1,000 mg/day |
| 31-50 yr | 580 mg/day | 1,000 mg/day |

Because there are no direct studies showing increased needs in pregnancy, the Estimated Average Requirement and Recommended Dietary Intake were set at those of the non-pregnant state.

As used herein, the term "dietary supplement" refers to a composition administered orally to provide a substance or substances either missing or insufficiently represented in the diet of an individual administered or taking such supplement. In the case of livestock, a dietary supplement is generally administered by mixing it with feed or, alternatively, by supplementing the feed during feed production. In the case of humans, a dietary supplement is generally administered as a pill, liquid or suspension; however, a "dietary supplement" for administration to humans can alternatively be mixed with food or drink to be consumed by the individual.

As used herein, the term "supplemental strontium" means exogenously added strontium. The strontium can be added, e.g., as any of a number of different strontium salts. Non-limiting examples include strontium carbonate, strontium renalate and strontium malonate, among others.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice of the present invention, the preferred methods and materials are now described. All publications mentioned herein are incorporated herein by reference to disclose and describe the methods and/or materials in connection with which the publications are cited.

As young pigs represent an excellent model of bone mass and strength for humans[6,7,9,19], the experiments described herein use weanling pigs to examine the effects of various treatments on bone mass and strength. The findings in this model system are fully anticipated to be representative of those achievable in a human undergoing similar treatment. The treatments described herein are also applicable to companion and zoo animals, including, but not limited to dogs, cats and horses, as well as to agriculturally important animals (e.g., cattle, sheep, goats, pigs, chickens, ducks, geese, turkeys, ostriches, emus, fish and the like).

Phytases

A number of plant and microbial phytase enzymes have been cloned. For example, two phytases, phyA and phyB, from Aspergillus niger NRRL3135 have been cloned and sequenced (Ehrlich, K. C. et al., "Identification and Cloning of a Second Phytase Gene (phys) from Aspergillus niger (ficuum)," Biochem. Biophys. Res. Commun., 195:53-57 (1993); Piddington, C. S. et al., "The Cloning and Sequencing of the Genes Encoding Phytase (phy) and pH 2.5-optimum Acid Phosphatase (aph) from Aspergillus niger var. awamori," Gene 133:56-62 (1993)). Recently, new phytase genes have been isolated from Aspergillus terreus and Myceliophthora thermophila (Mitchell et al., "The Phytase Subfamily of Histidine Acid Phosphatases, Isolation of Genes for Two Novel Phytases From the Fungi Aspergillus terreus and Myceliophthora thermophila," Microbiology 143:245-52, (1997)), Aspergillus fumigatus (Pasamontes et al., "Gene Cloning, Purification, and Characterization of a Heat-Stable Phytase from the Fungus Aspergillus fumigatus" Appl. Environ. Microbiol., 63:1696-700 (1997)), Emericella nidulans and Talaromyces thermophilus (Pasamontes et al., "Cloning of the Phytase from Emericella nidulans and the Thermophilic Fungus Talaromyces thermophilus," Biochim. Biophys. Acta., 1353:217-23 (1997)), and maize (Maugenest et al., "Cloning and Characterization of a cDNA Encoding a Maize Seedling Phytase," Biochem. J. 322:511-17 (1997)).

Various types of phytase enzymes have been isolated and/or purified from Enterobacter sp. 4 (Yoon et al., "Isolation and Identification of Phytase-Producing Bacterium, Enterobacter sp. 4, and Enzymatic Properties of Phytase Enzyme," Enzyme and Microbial Technology 18:449-54 (1996)), Klebsiella terrigena (Greiner et al., "Purification and Characterization of a Phytase from Klebsiella terrigena," Arch. Biochem. Biophys. 341:201-06 (1997)), and Bacillus sp. DS11 (Kim et al., "Purification and Properties of a Thermostable Phytase from Bacillus sp. DS11," Enzyme and Microbial Technology 22:2-7 (1998)). Properties of these enzymes have been studied. In addition, the crystal structure of phyA from Aspergillus ficuum has been reported (Kostrewa et al., "Crystal Structure of Phytase from Aspergillus ficuum at 2.5 A Resolution," Nature Structure Biology 4:185-90 (1997)).

Cloned phytase enzymes and active variants of them are also described in, e.g., U.S. Pat. Nos. 6,841,370, 6,511,699, 6,451,572, and 6,974,690, each of which is incorporated herein by reference. Plant phytase enzymes are described in, e.g., US2006/0253920, which is incorporated herein by reference. Other phytase enzymes are described in, e.g., EP0897010, WO97/48812, WO99/67398, WO01/36607, WO2004/015084, WO2006/028684 and WO01/90333, each of which is incorporated herein by reference.

Specifically included among phytases useful in the methods and compositions described herein are the *E. coli* AppA phytases, including the phytases having the amino acid sequence of SEQ ID NO: 1 or SEQ ID NO: 2 and conservative amino acid substitution mutants thereof that retain phytase activity:

tution which maintains: 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine. "Positively charged residues" relate to lysine, arginine or histidine. "Negatively charged residues" refer to aspartic acid or glutamic acid. Residues having "bulky side chains" refer to phenylalanine, tryptophan or tyrosine.

The terminology "conservative amino acid substitutions" is well known in the art, and relates to substitution of a particular amino acid by one having a similar characteristic (e.g., similar charge or hydrophobicity, similar bulkiness).

```
AppA (SEQ ID NO: 1); see GenBank Accession No. AAN28334
    1    mkailipfls  llipltpqsa  faqsepelkl  esvvivsrhg  vraptkatql  mqdvtpdawp 61    twpvklgwlt  prggeliayl  ghyqrqrlva  dgllakkgcp  qsgqvaiiad  vdertrktge 121    afaaglapdc  aitvhtqadt  sspdplfnpl  ktgvcqldna  nvtdailsra  ggsiadftgh 181    rqtafreler  vlnfpqsnlc  lkrekqdesc  sltqalpsel  kvsadnvslt  gavslasmlt 241    kifllqqaqg  mpepgwgrit  dshqwntlls  lhnaqfyllq  rtpevarsra  tplldlikta 301    ltphppqkqa  ygvtlptsvl  fiaghdtnla  nlggalelnw  tlpgqpdntp  pggelvferw 361    rrlsdnsqwi  qvslvfqtlq  qmrdktplsl  ntppgevklt  lagceernaq  gmcslagftq 421    ivnearipac  sl AppA2 (SEQ ID NO: 2); see GenBank Accession No. AAR87658
    1    mkailipfls  llipltpqsa  faqsepelkl  esvvivsrhg  vraptkatql  mqdvtpdawp 61    twpvklgwlt  prggeliayl  ghyqrqrlva  dgllakkgcp  qpgqvaiiad  vdertrktge 121    afaaglapdc  aitvhtqadt  sspdplfnpl  ktgvcqldna  nvtdailsra  ggsiadftgh 181    rqtafreler  vlnfsqlnlc  lnrekqdesc  sltqalpsel  kvsadnvslt  gavslasmlt 241    eifllqqaqg  mpepgwgrit  dshqwntlls  lhnaqfyllq  rtpevarsra  tplldlimaa 301    ltphppqkqa  ygvtlptsvl  fiaghdtnla  nlggalelnw  tlpgqpdntp  pggelvferw 361    rrlsdnsqwi  qvslvfqtlq  qmrdktplsl  ntppgevklt  lagceernaq  gmcslagftq 421    ivnearipac  sl
```

Cloned phytase enzymes can be expressed and purified according to methods well known in the art for inclusion in compositions and preparations as described herein. Expression in yeast systems is preferred (see, e.g., U.S. Pat. No. 6,451,572, which is incorporated herein by reference), although expression in other systems (e.g., bacterial systems, such as *E. coli*) can be used.

As well-known in the art, a "conservative mutation or substitution" of an amino acid refers to a mutation or substi- Examples include aspartic acid for glutamic acid, or isoleucine for leucine. A list of exemplary conservative amino acid substitutions is given in the table below. A conservative substitution mutant will 1) have only conservative substitution mutations relative to the parent sequence, 2) will have at least 90% sequence identity with respect to the parent sequence, preferably at least 95% identity, 96% identity, 97% identity, 98% identity or 99% identity; and 3) will retain phytase activity as that term is defined herein.

| CONSERVATIVE AMINO ACID REPLACEMENTS | | |
|---|---|---|
| For Amino Acid | Code | Replace With |
| Alanine | A | D-ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |

-continued

CONSERVATIVE AMINO ACID REPLACEMENTS

| For Amino Acid | Code | Replace With |
|---|---|---|
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P | D-Pro, L-I-thioazolidine-4-carboxylic acid, D-or-L-1-oxazolidine-4-carboxylic acid (Kauer, U.S. Pat. No. (4,511,390) |
| Serine | S | D-Ser, Thr, D-Thr, allo-Thr, Met, D-Met, Met (O), D-Met (O), L-Cys, D-Cys |
| Threonine | T | D-Thr, Ser, D-Ser, allo-Thr, Met, D-Met, Met (O), D-Met (O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Dosage and Administration

Phytase and strontium supplements as described herein can be formulated in any of a number of preparations for administration to humans or to animals. Effective dosages for humans will be similar to those found effective in pigs. However, the phytase enzyme and strontium need not be mixed with feed for human administration (although such administration can be suitable). Rather, for human administration, or as an alternative to feed formulations for non-human subjects, phytase enzyme can be formulated in liquid or dried form to be taken or administered as a dietary supplement. Thus, phytase enzyme can be prepared in liquid/elixir, pill or capsule form to be taken orally by a subject. Numerous formulations suitable for liquid, tablet or capsule administration are known to those of ordinary skill in the art. Dosage forms for supplemental strontium can be similarly formulated, although most often a pill or capsule is preferred. Any of a number of strontium salts can be used to provide the strontium; $SrCO_3$ is exemplified herein. As described herein, the phytase and supplemental strontium can be administered together, in a single formulation, or, alternatively, they can be administered in separate compositions, taken either concurrently or at different times.

Phytase dosages can range from, for example, 50-20,000 Units (U) per kg of feed for animal administration or 50-20,000 U/70 kg body weight per day for human administration, and all amounts in between. For animal administration in feed, phytase can be present at 50 U/kg of feed, 100 U/kg of feed, 150 U/kg of feed, 200 U/kg of feed, 250 U/kg of feed, 300 U/kg of feed, 500 U/kg of feed, 700 U/kg of feed, 900 U/kg of feed, 1000 U/kg of feed, 1500 U/kg of feed, 2000 U/kg of feed, 2500 U/kg of feed, 3500 U/kg of feed, 3500 U/kg of feed, 4000 U/kg of feed, 4500 U/kg of feed, 5000 U/kg of feed, 5500 U/kg of feed, 6000 U/kg of feed, etc. to about 20,000 U/kg of feed or more. Ranges of phytase dosages can thus encompass, for example, 50-15,000 U/kg of feed, 200-10,000 U/kg of feed, 200-5,000 U/kg of feed, 200-1,000 U/kg of feed, 200-750 U/kg of feed, 200-500 U/kg of feed, 500-20,000 U/kg of feed, 500-15,000 U/kg of feed, 500-10,000 U/kg of feed, 500-5,000 U/kg of feed, 500-1000 U/kg of feed, 1,000-20,000 U/kg of feed, 1,000-15,000 U/kg of feed, 1,000-10,000 U/kg of feed, or, for example, 1,000-5,000 U/kg of feed.

For human administration, for example, phytase can be administered orally at 50 U/70 kg body weight per day, 100 U/70 kg body weight per day, 150 U/70 kg body weight per day, 200 U/70 kg body weight per day, 250 U/70 kg body weight per day, 300 U/70 kg body weight per day, 500 U/70 kg body weight per day, 700 U/70 kg body weight per day, 900 U/70 kg body weight per day, 1000 U/70 kg body weight per day, 1500 U/70 kg body weight per day, 2000 U/70 kg body weight per day, 2500 U/70 kg body weight per day, 3500 U/70 kg body weight per day, 3500 U/70 kg body weight per day, 4000 U/70 kg body weight per day, 4500 U/70 kg body weight per day, 5000 U/70 kg body weight per day, 5500 U/70 kg body weight per day, 6000 U/70 kg body weight per day, etc. to about 20,000 U/70 kg body weight per day or more. The dosage of phytase can include, for example, 200-15,000 U/70 kg body weight per day, 200-10,000 U/70 kg body weight per day, 200-5,000 U/70 kg body weight per day, 200-1,000 U/70 kg body weight per day, 200-750 U/70 kg body weight per day, 200-500 U/70 kg body weight per day, 500-20,000 U/70 kg body weight per day, 500-15,000 U/70 kg body weight per day, 500-10,000 U/70 kg body weight per day, 500-5,000 U/70 kg body weight per day, 500-1000 U/70 kg body weight per day, 1,000-20,000 U/70 kg body weight per day, 1,000-15,000 U/70 kg body weight per day, 1,000-10,000 U/70 kg body weight per day, or, for example, 1,000-5,000 U/70 kg body weight per day.

Supplemental strontium dosages can be, e.g., similar to those administered to pigs in the studies described herein, e.g., about 350 mg/kg body weight/day. One should be mindful of the toxicity of various strontium salts (see, e.g., The Merck Index, 12th Edition; as examples, strontium acetate has an LD50 in rats of 1.16 mmol/kg; strontium bromide has an LD50 in rats of 1 g/kg body weight; strontium chloride has an LD50 of 147.6 mg/kg body weight in mice; strontium iodide has an LD50 in rats of 800 mg/kg body weight; and strontium nitrate has an LD50 of 540 mg/kg body weight in rats). Much lower doses (in fact, dosages reduced around 100-fold or more below the dosages typically administered for human treatment) can also be surprisingly effective in combination with phytase. Thus, in one aspect, the methods and compositions described herein provide dosages over a hundred-fold lower than normally used for human treatment, e.g., 0.5-2.5 mg/kg body weight/day. One can thus administer strontium at dosage ranges of, e.g., 0.5-200 mg/kg body weight/day, 0.5-100 mg/kg body weight/day, 0.5-50 mg/kg body weight/day, 0.5-10 mg/kg body weight/day, 2.5-100 mg/kg body weight/day, 2.5-50 mg/kg body weight/day, 2.5-10 mg/kg body weight/day, 5-200 mg/kg body weight/day, 5-100 mg/kg body weight/day, 5-50 mg/kg body weight/day, 5-20 mg/kg body weight/day, 10-200 mg/kg body weight/day, 10-100 mg/kg body weight/day, 10-50 mg/kg body weight/day, 50-200 mg/kg body weight/day, 50-100 mg/kg body weight/day, or 50-75 mg/kg body weight per day. The amount of strontium by weight in a dietary supplement composition can be adjusted as necessary to achieve doses in these ranges.

In one aspect, phytase enzyme with or without strontium can be administered daily in dosages as noted. In other aspects, preparations can be administered several times a day, e.g., with each meal, e.g., 3 times a day. Alternatively, phytase enzyme and/or strontium preparations can be administered less frequently, e.g., every other day, once or twice a week, every two weeks, once per month, etc. Where phytase and strontium are administered separately, the different agents can be administered on different schedules if so desired. Thus, as but one example, phytase can be administered daily, and strontium can be administered every other day. Bone health benefits of phytase administration with and without supplemental strontium in young subjects are demonstrated herein. Phytase, with or without supplemental strontium can be administered to adult subjects, e.g., humans or companion animals, to promote bone health and bone strength. The effectiveness of such treatment can be monitored according to the methods described herein in the section "Efficacy measurement."

Any animal feed blend known in the art may be used such as a blend of rapeseed meal, cottonseed meal, soybean meal, or cornmeal. In various embodiments, the animal feed can be supplemented with sugars and complex carbohydrates such as both water-soluble and water-insoluble monosaccharides, disaccharides and polysaccharides. Optional amino acid ingredients that may be added to the feed blend are arginine, histidine, isoleucine, leucine, lysine, methionine, phenylalanine, threonine, tryptophan, valine, tyrosine ethyl HCl, alanine, aspartic acid, sodium glutamate, glycine, praline, serine, cysteine ethyl HCl, and analogs, and salts thereof. Vitamins that may be optionally addred are thiamine Hcl, riboflavin, pyridoxine HCl, niacin, niacinamide, inositol, choline chloride, calcium pantothenate, biotin, folic acid, ascorbic acid, and vitamins A, B, K, D, E and the like. Protein ingredients may also be added and include protein obtained from meal or fish meal, liquid or powdered egg, fish solubles, and the like.

Efficacy Measurement

A treatment is considered "effective treatment," as the term is used herein, if any measure of bone structure, function and/or strength described herein increases by a statistically significant amount. This includes measures of bone structure and function based on the breaking strength of the bone when removed from the body. Obviously, however, in human or animal clinical applications this is not a preferred measure of efficacy. To avoid any doubt, then, an "effective treatment" will increase bone mineral density by at least 3% relative to the bone mineral density value before initiating treatment as described herein. Such an increase is, therefore, indicative of an improvement in bone structure, function and/or strength. While there are many different types of BMD tests, those applicable to monitoring of the treatment methods described herein are preferably non-invasive.

Suitable tests include, for example: Dual Energy X-ray Absorptiometry (DXA or DEXA), Quantitative Computed Tomography (QCT), Qualitative Ultrasound (QUS), Digital X-ray Radiogrammetry (DXR) and Single Energy X-ray Absorptiometry (SEXA). For these tests, properties of a specific bone or bones are measured, usually the spine, hip and wrist. The density of these bones is then compared with an average index based on age, sex, and size. Average bone mineral density=BMC/W [g/cm$^2$]. BMC=bone mineral content=g/cm. W width at the scanned line.

Alternatively, "effective treatment" is indicated by a slowing or cessation of the loss of bone mineral density in an individual experiencing such loss prior to the initiation of treatment. Bone mineral density and other measures of bone health can be determined by those of skill in the art using methods known in the art or described herein.

Treatment includes any treatment of a disease or disorder (e.g., osteoporosis) in an animal and includes: (1) preventing the disease from occurring in a mammal which may be predisposed to the disease but does not yet experience or display symptoms of the disease; e.g., prevention of the outbreak of the clinical symptoms; (2) inhibiting the disease, e.g., arresting its development; or (3) relieving the disease, e.g., causing regression of the symptoms of the disease. An "effective amount" of an agent for the treatment or prevention of a disease or disorder means that amount which, when administered to a mammal in need thereof, is sufficient to result in effective treatment as that term is defined herein, for that disease or disorder.

Thus, in accordance with experience and knowledge, the practicing clinician can modify each protocol for the administration of a component of the treatment according to the individual subject's needs, as the treatment proceeds.

The present invention is illustrated by the following non-limiting examples. It is to be understood that the particular examples, materials, amounts and procedures are to be interpreted broadly in accord with the scope and spirit of the invention as set forth herein and are not intended to limit the invention in any way. All references described herein, including patents and patent applications as well as literature references, whether published in paper or online versions, are incorporated herein by reference in their entirety.

EXAMPLES

Example 1

Materials and Methods Used in the Experiments Described Herein

Animals, Diets, and Treatments.

The experimental protocol was approved by the Institutional Animal Care and Use Committee of Cornell University. All pigs used in the study were weanling crossbreds (Landrace-Hampshire-Duroc) selected from the Cornell University Swine Farm. Pigs were weaned at 4 wk of age, and allotted into treatment groups based on body weight, litter and sex. Two preliminary experiments using 56 gilts (5-wk old) fed different levels of inorganic P concentration (0, 0.2, and 0.25%) and phytase activity (0, 1,000, and 2,000 U/kg) were conducted for 4 or 5 wk to determine the appropriate dietary inorganic P concentration and phytase activity for the experimental objectives.

Based on results of the preliminary trials, Experiment 1 was conducted with 24 gilts (6-wk old, 8.6±0.1 kg body weight) to test the possible benefit of phytase to metatarsal breaking load of pigs fed the corn-soybean meal basal diet (BD, Table 1). The BD contained 0.33% available P and adequate concentrations of all other required nutrients (24). The selected pigs were divided into two groups (n=12), and were fed BD or BD+phytase at 2,000 U/kg for 6 wk.

Subsequently, Experiment 2 was conducted with 32 pigs (8-wk old, 11.4±0.2 kg body weight) to determine the possible additive or synergistic effects of supplemental phytase and Sr on mechanical and chemical properties of metatarsal and femur bones. The pigs were divided into four groups (n=8), and were fed BD, BD+phytase (2,000 U/kg), BD+Sr (50 mg/kg) or BD+phytase (2,000 U/kg)+Sr (50 mg/kg). The phytase used in both experiments was *Escherichia coli* AppA2 (OptiPhos, JBS United, Inc., Sheridan, Ind.). After the actual activity was analyzed[25], the phytase enzyme was added to the diets at feed mixing. Strontium was added to the diet in the form of $SrCO_3$ (Alfa Aesar, Ward Hill, Mass.). Pigs were penned in an environmentally controlled barn (20-25° C.; 12 h light: 12 h dark cycle), and were allowed free access to feed and water.

Growth Performance and Sample Collection.

In both experiments, body weight of individual pigs was measured weekly. Blood samples of individual pigs were collected at initial (wk 0) and then weekly from the anterior vena cava into heparinized tubes after an overnight fast (8 h). The collected whole blood samples were chilled on ice and centrifuged at 3,000×g (GS-6KR centrifuge, Beckman Instruments Inc.) for 10 min at 4° C. to prepare plasma for assays of inorganic P concentrations and alkaline phosphatase activity. At the end of Experiments 1 and 2, 8 and 6 pigs from each treatment group were killed by electrical stunning and exsanguinations, respectively.ABear legs were amputated and stored on ice at 4° C. until the femur and(or) $3^{rd}$ and $4^{th}$ metatarsals were isolated for mechanical and(or) image tests (see below). Following strength tests, bones were stored at −20° C. for mineral analysis.

Plasma Biochemical Analyses.

After being deproteinated with 12.5% tricholoacetic acid, plasma samples were assayed for inorganic P concentrations using Elon (p-methylaminophenol sulfate) solution[26]. The hydrolysis of p-nitrophenol phosphate to p-nitrophenol was used to measure plasma alkaline phosphatase activity[27]. The enzyme unit was defined as 1 μmol of p-nitrophenol released per minute at 30° C.

Bone Geometrical and Strength Analyses.

Third and 4th metatarsals in both experiments and femur (right leg) in Experiment 2 were prepared by manually removing surrounding skin, muscle and other tissues. Bones were stored in closed plastic bags at 4° C. until strength analysis. Maximal breaking load was measured using an Instron 4500 Machine (Canton, Mass.) at room temperature (23° C.) by subjecting each bone to a three-point bending test[28]. During mechanical tests, force was applied to the center of the bone held by supports 2.0 cm apart for metatarsals and 3.3 cm apart for femur. The crosshead speed was set at 50 mm/min and the sample rate was 10 points/s. Final strength was determined from load-displacement curves indicating the maximum loads. The metatarsal breaking strength was expressed as the mean strength of four bones from both left and right feet of pigs in Experiment 1, and as the mean of the two bones from the right foot of pigs in Experiment 2.

In Experiment 2, bone mineral content (BMC, g) and bone mineral density (BMD, $g/cm^2$) of $3^{rd}$ and $4^{th}$ metatarsals from the left foot and femur from the left leg of each pig were measured. After being thawed to room temperature, entire bones were placed on a rice bag (to remove background effects) and scanned by dual energy X-ray absorptiometry using the GE Lunar Prodigy instrument (GE Lunar, Prodigy, Madison Wis.) in the small animal scan mode. Values of BMC and BMD were predicted by analysis of scans using Prodigy software (version 10.10.038).

Because the metatarsal bones do not have a clear defined cortical bone wall, geometric and image measurements were made in only femur bones of the left legs in Experiment 2. A three-point bending test was conducted on the dissected bones to generate load-deformation curves with an Instron Model 5566 (Norwood, Mass.). Mechanical properties of bones were calculated using formula as previously described[29]. Bone cross sections were cut at the mid-point of loading and used to determine area moment of inertia. Cross sections were submersed for 5 min in a 0.4 mol/L sodium hypochlorite solution to remove periosteum and marrow tissue, and then embedded in blue clay (Play-Doh, Hasbro, Pawtucket, R.I.) to prevent depth-of-field distortions and to enhance contrasts. The embedded sections were scanned with a flat-bed scanner (Epson Perfection Model 3490, Long Beach, Calif.) and analyzed using Image J software (30) to measure the x-y coordinates of bone pixels.

Bone Mineral Concentration Analyses.

After the breaking strength analysis, samples (~100 to 200 mg) of metatarsals in both experiments and femur in Experiment 2 from the right legs were used for mineral analysis. Cortical bones were isolated after removing attached connective tissue using a stainless steel scalpel and collecting individual shards using needle-nosed pliers with plastic-covered clamps. The samples were dried for 8 h at 105° C. to measure dry weight. Concentrations of individual elements in the dried bone samples were measured using inductively coupled argon plasma spectrophotometer (ICAP 61E Trace Analyzer, Thermo Jarell Ash corporation, Franklin, Mass.)(31). Samples were digested in a mixture of $HNO_3$ and $HClO_4$ (9:1, vol/vol), and then diluted in 5% $HNO_3$ before analysis. Standard reference materials (No. 1573a, tomato leaves, and No. 1577b, bovine liver, National Institute of Standards and Technology, Gaithersburg, Md.) were used to validate the analytical procedures[32].

Statistical Analyses.

Data were analyzed as a randomized block design using the General Linear Models procedure of SAS (version 6.12, SAS Inst., Inc., Cary, N.C.). Main effects of dietary treatments on various measures were analyzed using one-way ANOVA in Experiment 1 and a 2×2 factorial ANOVA in Experiment 2. Each individual pig was used as the experimental unit. The Boneferroni t-test was used to compare treatment means, and the significance level was set at $P \leq 0.05$[33]. For the repeated-measured traits including body weights, plasma inorganic P concentrations, and plasma alkaline phosphatase activity, only the data from the initial and final weeks were presented because of the similar trends at other times.

Example 2

Examination of the Effect of Phytase on Metatarsal Breaking Load of Pigs Fed a Corn-Soybean Basal Diet Based on results of the preliminary trials, Experiment 1 was conducted with 24 gilts (6-wk old, 8.6±0.1 kg body weight) to test the possible benefit of phytase to metatarsal breaking load of pigs fed the corn-soybean meal basal diet (BD, Table 1). The BD contained 0.33% available P and adequate concentrations of all other required nutrients[24]. The selected pigs were divided into two groups (n=12), and were fed BD or BD+phytase at 2,000 U/kg for 6 wk.

Experiment 1 results: Pigs fed BD+2,000 U/kg showed 12% greater (P<0.02) breaking strength of metatarsals (98.8±3.2 vs. 112.0±3.9 kg) than those fed only BD. These phytase-fed pigs had 7% (P<0.05) higher Sr concentrations, but similar concentrations of other elements in metatarsals, compared with the pigs fed BD (Table 2). These two groups of pigs shared very similar body weight (32.1±0.6 vs. 33.4±0.8 kg), plasma inorganic P concentration (81.7±0.1 vs. 83.6±0.1 g/L), and plasma alkaline phosphatase activity (161.7±8.6 vs. 173.0±6.8 U/L) at the end of the experiment.

Example 3

Examination of the Effects of Supplemental Phytase and Strontium on Mechanical And Chemical Properties of Metatarsal and Femur Bones Experiment 2 was conducted with 32 pigs (8-wk old, 11.4±0.2 kg body weight) to determine the possible additive or synergistic effects of supplemental phytase and Sr on mechanical and chemical properties of metatarsal and femur bones. The pigs were divided into four groups (n=8), and were fed BD, BD+phytase (2,000 U/kg), BD+Sr (50 mg/kg) or BD+phytase (2,000 U/kg)+Sr (50 mg/kg). The phytase used in both experiments was *Escherichia coli* AppA2 (OptiPhos, JBS United, Inc., Sheridan, Ind.). After the actual activity was analyzed[25], the phytase enzyme was added to the diets at feed mixing. Strontium was added to the diet in the form of $SrCO_3$ (Alfa Aesar, Ward Hill, Mass.). Pigs were penned in an environmentally controlled barn (20-25° C.; 12 h light: 12 h dark cycle), and were allowed free access to feed and water.

Figure 1A:
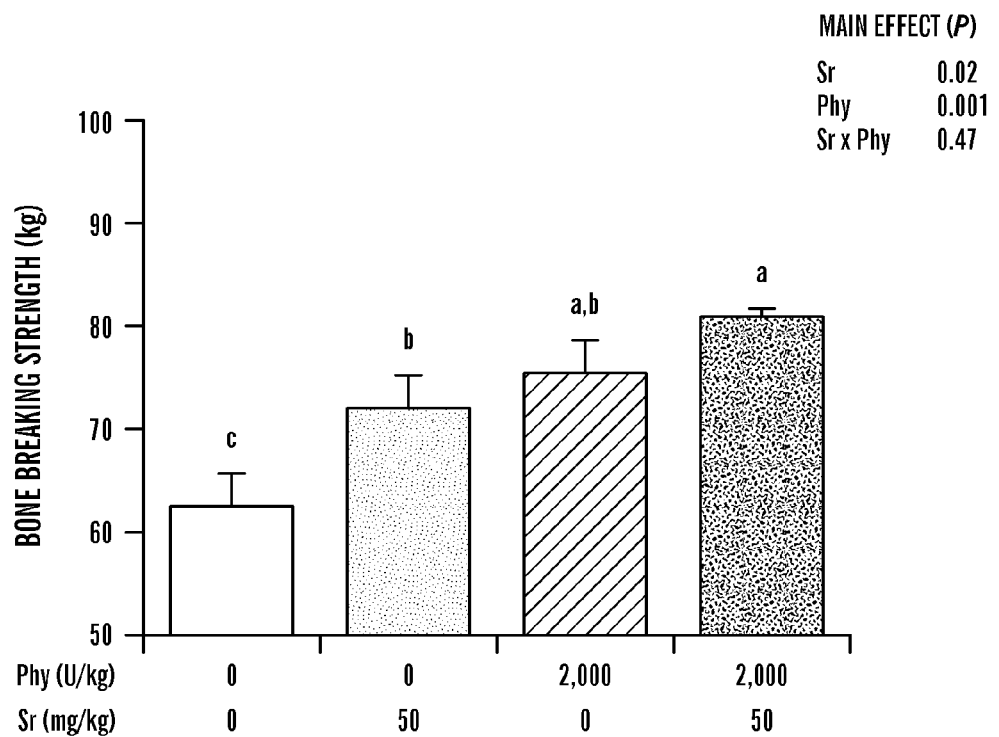
FIG. 1 shows the effects of dietary supplemental phytase (Phy) and strontium (Sr) on metatarsal (A) and femur (B) breaking strength of pigs as described in Example 3. Values are means±SE, n=6. Means without sharing a common letter differ (P<0.05); and b* indicates a marginal significant difference (P=0.06) between the two means. Phy: phytase.
Figure 1B:
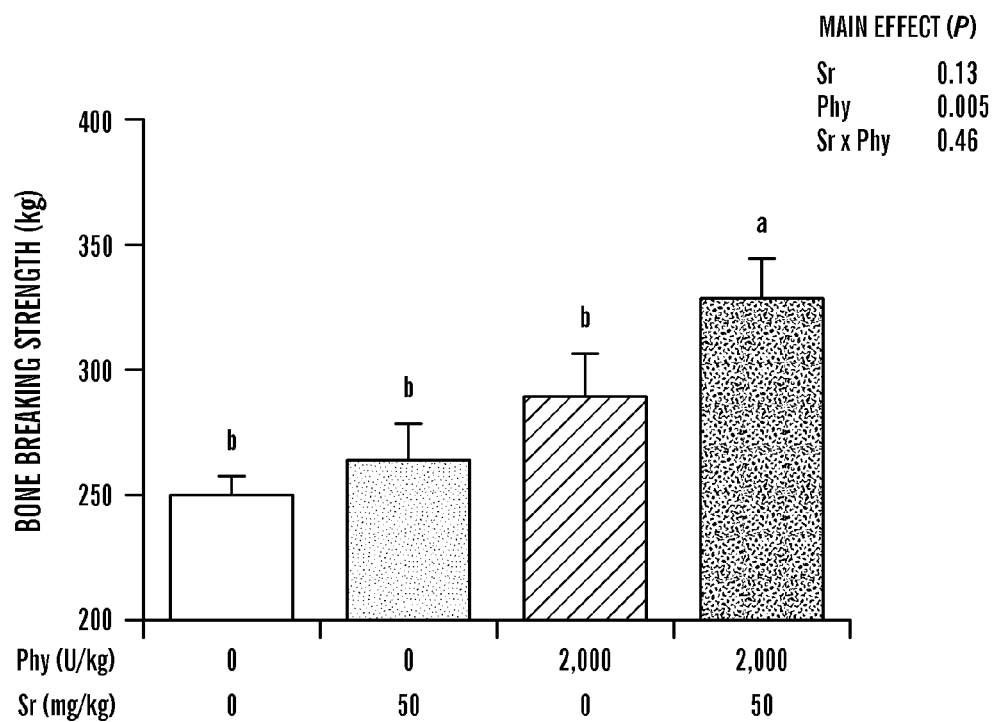
Figure 2A:
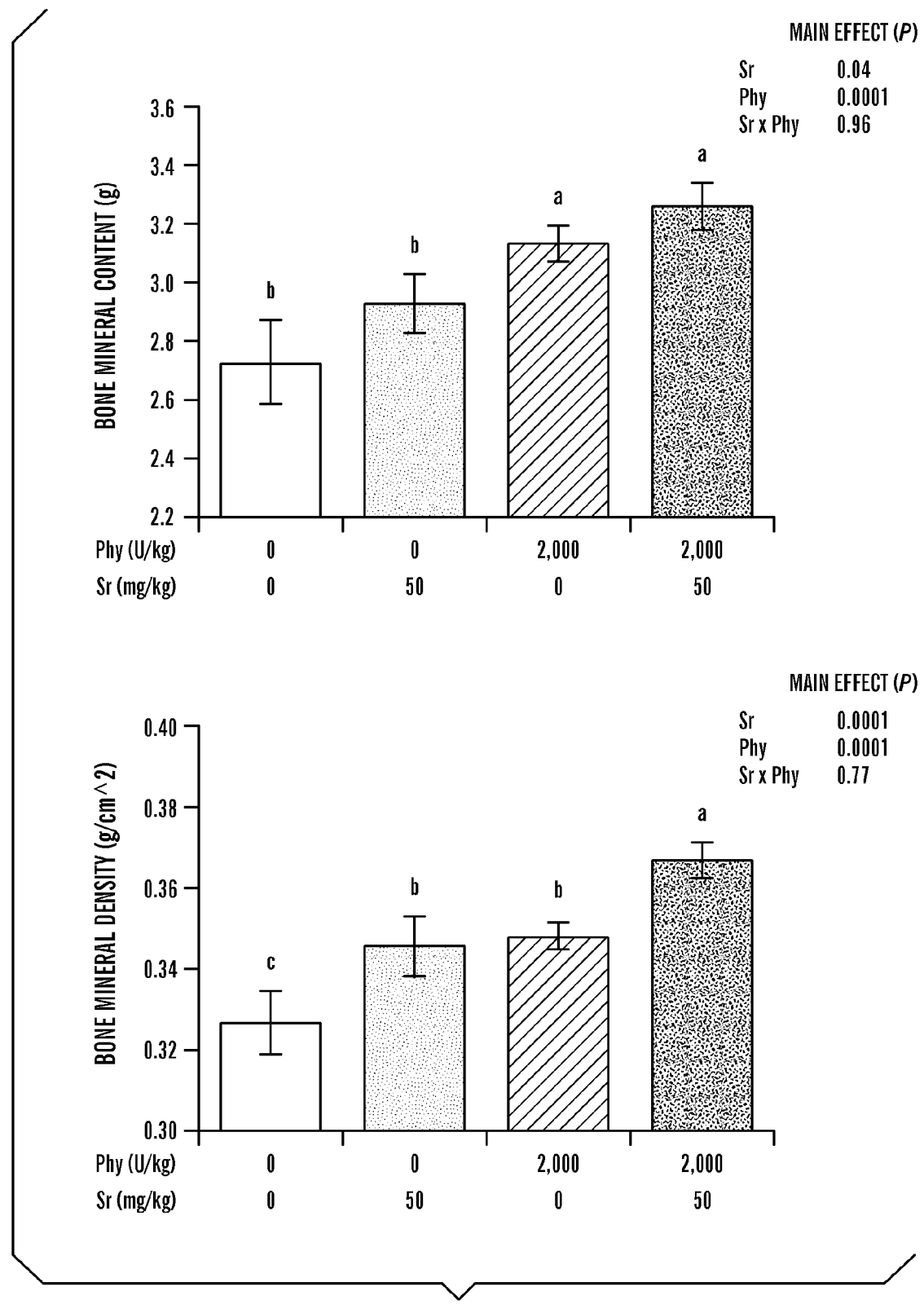
FIG. 2 shows the effects of dietary supplemental phytase (Phy) and strontium (Sr) on bone mineral content (BMC, upper panel) and bone mineral density (BMD, lower panel) of metatarsal (A) and femur (B) of pigs as described in Example 3. Values are means±SEM, n=6. Means without sharing a common letter differ (P<0.05). Phy: phytase.
Figure 2B:
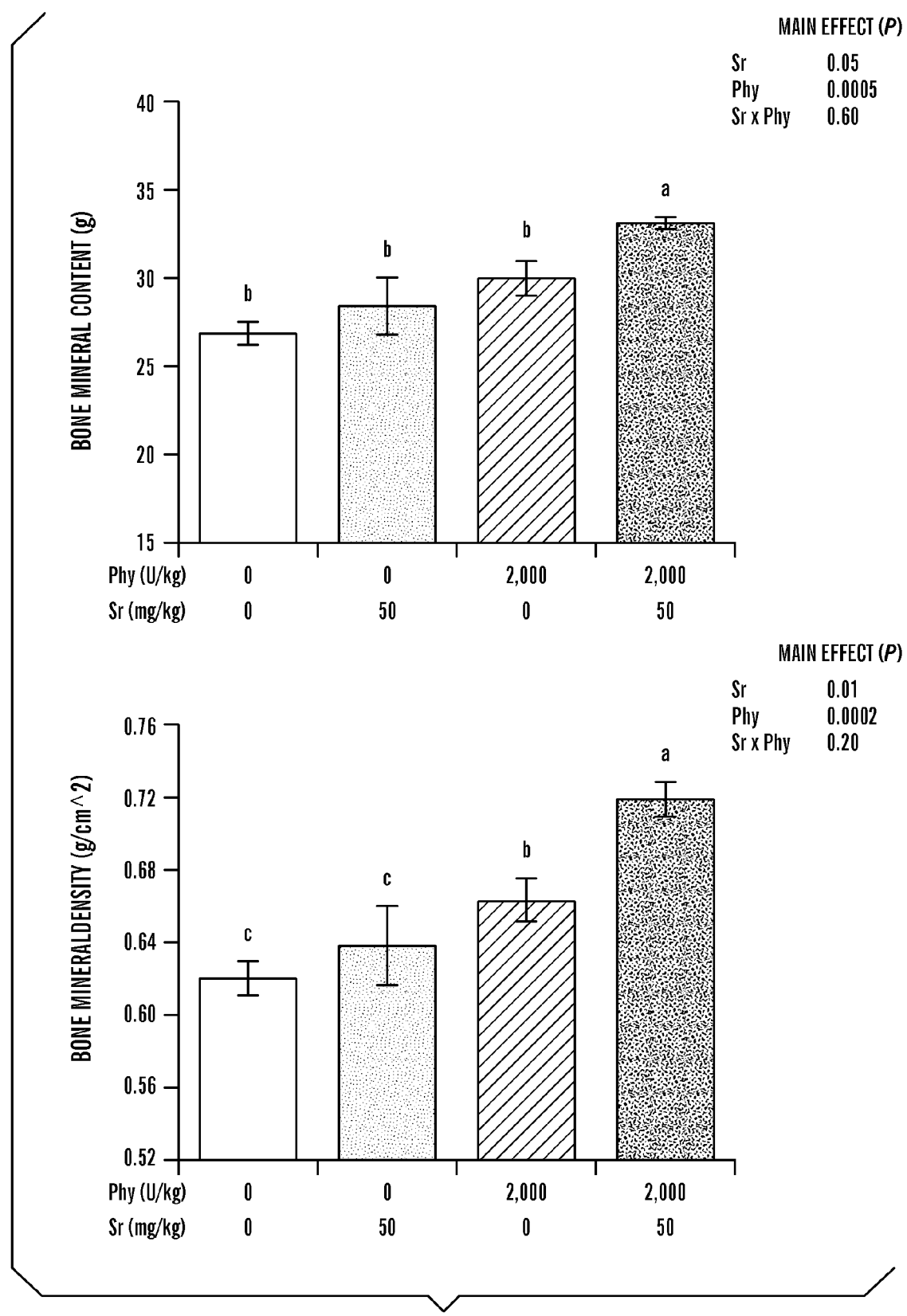

Experiment 2 results: While final body weight, plasma inorganic P concentration, or plasma alkaline phosphatase activity of pigs was not statistically different among dietary treatment groups (Table 3), the breaking strengths of metatarsals (FIG. 1A) and femur (FIG. 1B) were elevated by supplemental phytase (P<0.005) and Sr (P<0.02), respectively. The improvement in metatarsals and femur was 16 and 20% by phytase and 11 and 10% by Sr, respectively. In both bones, BMC was enhanced 14 to 15% by phytase (P<0.001), and 6 to 8% by Sr (P<0.05) (FIG. 2). Meanwhile, BMD of the two bones was elevated 9 to 11% by phytase (P<0.001), and 6% by Sr (P<0.01). Total bone area (calculated by length×width based on dual energy X-ray absorptiometry) of metatarsal (8.4±0.1 vs. 9.0±0.2 $mm^2$) and femur (43.6±0.6 vs. 45.8±0.7 $mm^2$) was increased (P<0.05) 7 and 5%, respectively, by phytase. However, there was no interaction between phytase and Sr on breaking strength, BMC, or BMD of either bone.

The cross-sectional area of femur from pigs fed phytase was 11% (P=0.06) larger than that of pigs fed diets without phytase (Table 4). Supplemental phytase also tended to enhance cross-sectional area moment of inertia, in particular in pigs fed the diet without supplemental Sr, but the main effect of phytase or its interaction with Sr was not statistically significant. The radius (distance from the neutral axis to maximum outer surface) of femur was not affected by supplemental phytase or Sr. The yield bending moment of femur was enhanced 19% (P<0.05) by supplemental phytase. No treatment differences were detected in the stress or strain values at either the yield or ultimate points on the load-deformation curves. There was no difference in modulus of elasticity (a measure of the rigidity of bone) among treatment groups. The interaction between supplemental phytase and Sr on maximal stress of femur was marginally significant (P=0.09).

Metatarsal concentration of Sr was elevated 4-fold (P<0.0001) by Sr and 11% (P<0.07) by phytase (Table 5). Meanwhile, supplemental phytase reduced metatarsal concentrations of S(P<0.01) and Cr (P<0.05). Supplemental Sr tended (P=0.09 to 0.10) to reduce metatarsal concentrations of Ca, P, and Fe, especially in pigs fed phytase. However, the interaction between Sr and phytase on either element was not statistically significant. There was a marginally significant interaction between phytase and Sr (P=0.08) on metatarsal concentration of Na. Femur concentration of Sr was enhanced 3.9-fold (P<0.0001) by Sr, but was not affected by phytase (Table 6). Femur concentration of S was decreased (P<0.01) whereas that of Zn was increased (P<0.05) by phytase. Supplemental Sr tended to reduce (P=0.07) femur concentrations of Fe, Cr, and Mn.

The results of Experiment 1 clearly demonstrate that supplementing *Escherichia coli* AppA2 phytase at 2,000 U/kg of diet enhanced breaking strength of metatarsals in P-adequate pigs. Although supplemental moderate levels of phytase activity have been shown to effectively replace inorganic P in pigs fed low-P diets[34-36], findings from the present study illustrate a function of phytase added at a relatively high level in diets with more than adequate concentrations of inorganic P. Because the final status of all assayed P-responsive measures[37,38], including metatarsal concentrations of P and Ca, was very similar between pigs fed only BD and BD+phytase, the benefit of supplemental phytase to metatarsal breaking strength was unlikely a response to further improvements in P availability.

The 7% elevation of metatarsal Sr concentration in pigs fed BD+phytase over those fed only BD in Experiment 1 prompted Experiment 2, to examine an interaction between phytase and Sr on bone metabolism. Indeed, the breaking strengths of metatarsals and femur were improved by both supplements. Because pig bones do not meet the length to diameter ratios needed for pure bending (compression and tension forces), the three-point bending test used to measure breaking strength of entire bones in both experiments probably involved combined shear and tensile failure modes[28]. Nevertheless, the results allow a relative comparison between dietary treatment groups. Further characterizations of entire femur mineral content by dual energy X-ray absorptiometry, along with geometrical analysis of cross-sections and mechanical tests, helped reveal the mode of action for the two supplements. The enhancements of BMC and BMD in metatarsals and femur by both phytase and Sr indicate their common ability to shift bone chemical profiles. In contrast, only supplemental phytase, but not Sr, increased total bone surface areas of both bones and the cross-sectional area at the midshaft region of femur. Thus, there is a distinct difference between the two supplements in altering femur geometrical properties or anatomical structures. The larger cross-sectional area, along with the seemingly elevated cross-sectional area moment of inertia, allowed femur from pigs fed phytase to withstand more force (greater yield bending moment) than those from pigs fed diets without phytase. However, the stress and strain values at each point of bone or the rigidity of bone was not altered by either phytase or Sr.

The lack of significant interactions between phytase and Sr on bone geometrical or strength properties indicates fairly independent actions for the two supplements. In Experiment 2, supplemental Sr resulted in a rather consistent elevation (4-fold) in Sr concentrations of cortical metatarsal and femur. In comparison, supplemental phytase caused a moderate elevation (11%) of Sr concentration in only metatarsals. Thus, the benefit of supplemental phytase to the properties of femur was not necessarily related to the enhanced Sr deposition in the cortical bone. Although mineral concentrations expressed on dry bone basis may fluctuate with fat content, that source of variation unlikely exerted major impact on our results because Ca:P ratios in metatarsal or femur were essentially identical across the dietary treatment groups. While supplemental phytase produced an inconsistent effect on Zn and Cr concentrations of metatarsals and femur, it consistently reduced S concentrations in both bones in Experiment 2. This raises a fascinating question whether the enzyme improved bone metabolism of P-adequate pigs via modulating S incorporation and distribution. Copious amounts of S represent a structural component of proteoglycans in bone[39], and thus are involved in bone formation and repairing[40,41]. The trend of decreasing femur concentrations of Fe, Cr, and Mn as well as metatarsal concentrations of Ca, P, and Fe in Experiment 2 may not be simply explained by displacement of increased Sr deposition[42,44]. In fact, the reduction in Ca and P concentrations was magnitude greater than the increase in Sr concentration. Although the Sr-related reduction of metatarsal Ca and P concentrations was apparent in pigs fed phytase that exhibited the best responses of bone properties, the observed enhancement of bone strength might be mainly caused by the changes of Sr per se. Sr can be enriched to high concentrations in cancellous bones[42] to stimulate bone remodeling[45] and cartilage matrix formation[46].

The positive effect of the low level of Sr supplementation on bone breaking strength and material properties in Experiment 2 extends our knowledge of this element on bone metabolism. Due to observed adverse effects on other minerals[48], Sr was abandoned as a therapeutic agent for osteoporosis. Interest in Sr as an osteopenic treatment has been renewed with the realization that low doses of Sr ($\leq 0.35$ g Sr/kg of body weight day) exerted no negative effects in the presence of adequate Ca intake[22]. Overall, studies in rodents, monkeys, and humans have shown that low doses of Sr inhibit bone resorption and(or) stimulate bone formation[42]. In the present study, supplemental Sr at 50 mg/kg of feed represented an average daily intake of 3 mg of Sr/kg of body weight. Apparently, this dose of Sr was safe[22] and caused no obvious adverse responses. In summary, Applicants have shown that a high level of bacterial phytase and a low level of inorganic Sr improve bone breaking strength of pigs fed adequate inorganic P. The former appeared to affect both geometrical and chemical properties of bone, whereas the latter mainly altered chemical properties of bones.

TABLE 1

Composition of the basal diet[1]

| Ingredient | g/kg |
| --- | --- |
| Corn, grain | 657.5 |
| Soybean meal, 48% CP | 280.0 |
| Spray-dried plasma protein | 15.0 |
| Corn Oil | 10.0 |
| L-Lysine•HCl | 1.0 |
| Vitamin/mineral premix[1] | 2.0 |
| Dicalcium phosphate | 13.5 |
| Limestone | 10.5 |
| $MgO_4$ | 0.5 |
| Salt | 5.0 |
| Tylan[2] | 5.0 |
| Total | 1000 |

Nutritional values

| | |
| --- | --- |
| $ME^3$, MJ/kg | 14.1 |
| Crude protein[3], % | 20.0 |
| Ca, total, % | 0.81 |
| P, total, % | 0.66 |
| P, available, % | 0.33 |
| Ca:P, total | 1.24 |

[1]Vitamin and mineral premix provided/kg diet: retinyl palmitate, 1,650 µg; cholecalciferol, 27.5 µg; dl-α-tocopheryl acetate, 16.08 µg; menadione, 0.73 mg; d-biotin, 26 µg; choline chloride, 66 mg; niacin, 26.4 mg; Ca-D-panthothenate, 17.6 mg; riboflavin, 4.4 mg; $CuSO_4 \cdot 5H_2O$, 6 mg; $C_2H_8N_2HI$, ethylene diamine dihydroiodide, 0.14 mg; MnO, 4 mg; $Na_2SeO_3$, 0.3 mg; ZnO, 100 mg.
[2]Antibiotic additive (Tylan 10) contains tylosin (as tylosin phosphate) at 22 g/kg (Elanco).
[3]Calculated based on NRC (24).

TABLE 2

Effect of dietary supplemental phytase on metatarsal mineral concentrations of pigs in Expt. 1[1]

| | Treatment | | | |
| --- | --- | --- | --- | --- |
| Phytase, U/kg | 0 | 2000 | SEM | P |
| Macrominerals, g/kg | | | | |
| Ca | 224.4 | 217.3 | 5.3 | 0.36 |
| P | 111.2 | 109.2 | 2.3 | 0.55 |
| Mg | 3.5 | 3.6 | 0.5 | 0.24 |
| Na | 6.1 | 6.2 | 1.0 | 0.60 |
| S | 1.2 | 1.2 | 0.03 | 0.74 |
| Microminerals, mg/kg | | | | |
| Sr | 58.4 | 62.8 | 1.5 | 0.05 |
| Fe | 13.8 | 15.7 | 2.2 | 0.54 |
| Zn | 171.6 | 176.1 | 4.7 | 0.51 |
| Cr | 6.3 | 6.4 | 0.1 | 0.82 |
| Mn | 1.0 | 1.1 | 0.1 | 0.41 |

[1]Values are means, n = 8.

TABLE 3

Effect of dietary supplemental phytase and strontium on growth performance and plasma measures of pigs in Expt. 2[1]

| | | Treatment Phytase, U/kg | | | | | Main Effect (P) | | |
| --- | --- | --- | --- | --- | --- | --- | --- | --- | --- |
| | | 0 | 0 | 2000 | 2000 | | | | |
| | | Sr, mg/kg | | | | | | | |
| | | 0 | 50 | 0 | 50 | SEM | Sr | Phy | Sr × Phy |
| Body weight, kg | 0 | 11.5 | 11.3 | 11.3 | 11.5 | 0.5 | 0.91 | 0.99 | 0.70 |
| | 5 | 35.4 | 36.1 | 34.9 | 36.3 | 1.2 | 0.40 | 0.92 | 0.75 |
| Plasma inorganic phosphorus, g/L | 0 | 77.6 | 82.0 | 76.0 | 84.1 | 3.8 | 0.11 | 0.95 | 0.63 |
| | 5 | 85.4 | 87.7 | 81.6 | 82.0 | 1.0 | 0.22 | 0.12 | 0.56 |
| Alkaline phosphatase activity, U/L | 0 | 210.2 | 251.0 | 202.1 | 223.7 | 19.8 | 0.09 | 0.32 | 0.59 |
| | 5 | 133.6 | 134.7 | 149.9 | 125.8 | 10.0 | 0.26 | 0.72 | 0.22 |

[1]Values are means, n = 8. Phy: phytase.

TABLE 4

Effect of dietary supplemental phytase and strontium on femur geometrical and strength properties of pigs in Exp. 2[1]

| | Treatment Phytase, U/kg | | | | | Main Effect (P) | | |
|---|---|---|---|---|---|---|---|---|
| | 0 | 0 | 2000 | 2000 | | | | |
| | Sr, mg/kg | | | | | | | |
| | 0 | 50 | 0 | 50 | SEM | Sr | Phy | Sr × Phy |
| Geometrical properties | | | | | | | | |
| Cross-sectional area, mm$^2$ | 143 | 151 | 165 | 161 | 7.9 | 0.76 | 0.06 | 0.45 |
| Moment of inertia, mm$^4$ | 4198 | 4891 | 5419 | 4947 | 422 | 0.80 | 0.15 | 0.18 |
| Cross-sectional radius, mm | 8.6 | 9.0 | 9.0 | 9.2 | 0.3 | 0.26 | 0.35 | 0.69 |
| Strength properties | | | | | | | | |
| Yield bending moment, kg-mm | 1330 | 1384 | 1507 | 1733 | 110 | 0.22 | 0.03 | 0.44 |
| Yield stress, kg/mm$^2$ | 2.7 | 2.6 | 2.7 | 3.3 | 0.3 | 0.39 | 0.26 | 0.18 |
| Strain | 0.05 | 0.05 | 0.06 | 0.06 | 0.004 | 0.71 | 0.18 | 0.54 |
| Modulus of elasticity, kg/mm$^2$ | 59 | 50 | 49 | 59 | 6.3 | 0.91 | 0.96 | 0.15 |
| Maximum bending moment, kg × mm | 2187 | 2286 | 2263 | 2579 | 129 | 0.12 | 0.17 | 0.42 |
| Maximum stress, kg/mm$^2$ | 4.5 | 4.3 | 4.0 | 4.9 | 0.3 | 0.30 | 0.91 | 0.09 |

[1]Values are mean, n = 6. Phy: phytase.

TABLE 5

Effect of dietary supplemental phytase and strontium on metatarsal mineral concentrations of pigs in Expt. 2[1]

| | Treatment Phytase, U/kg | | | | | Main Effect (P) | | |
|---|---|---|---|---|---|---|---|---|
| | 0 | 0 | 2000 | 2000 | | | | |
| | Sr, mg/kg | | | | | | | |
| | 0 | 50 | 0 | 50 | SEM | Sr | Phy | Sr × Phy |
| Macrominerals, g/kg | | | | | | | | |
| Ca | 179.7 | 178.4 | 187.4 | 165.1 | 6.7 | 0.09 | 0.68 | 0.13 |
| P | 89.1 | 88.1 | 91.8 | 81.4 | 3.3 | 0.10 | 0.54 | 0.17 |
| Mg | 3.5 | 3.5 | 3.5 | 3.2 | 0.11 | 0.19 | 0.41 | 0.22 |
| Na | 6.6 | 6.8 | 7.4 | 5.8 | 0.5 | 0.15 | 0.82 | 0.08 |
| S | 1.0 | 1.0 | 0.9 | 0.8 | 0.06 | 0.15 | 0.01 | 0.22 |
| Microminerals, mg/kg | | | | | | | | |
| Sr | 65.0 | 330.6 | 73.5 | 364.4 | 10.8 | 0.0001 | 0.07 | 0.23 |
| Fe | 14.1 | 23.5 | 15.3 | 11.5 | 2.9 | 0.10 | 0.38 | 0.65 |
| Zn | 131.2 | 146.8 | 152.3 | 147.0 | 7.2 | 0.47 | 0.16 | 0.17 |
| Cr | 21.1 | 26.6 | 20.5 | 19.2 | 2.1 | 0.37 | 0.05 | 0.18 |
| Mn | 2.4 | 2.8 | 2.0 | 2.2 | 0.8 | 0.74 | 0.56 | 0.94 |

[1]Values are mean, n = 6. Phy: phytase.

TABLE 6

Effect of dietary supplemental phytase and strontium on femur mineral concentrations of pigs in Expt. 2[1]

| | Treatment Phytase, U/kg | | | | | Main Effect (P) | | |
|---|---|---|---|---|---|---|---|---|
| | 0 | 0 | 2000 | 2000 | | | | |
| | Sr, mg/kg | | | | | | | |
| | 0 | 50 | 0 | 50 | SEM | Sr | Phy | Sr × Phy |
| Macrominerals, g/kg | | | | | | | | |
| Ca | 297.8 | 299.3 | 300.3 | 293.4 | 4.9 | 0.59 | 0.73 | 0.40 |
| P | 175.1 | 176.3 | 178.6 | 172.9 | 3.0 | 0.45 | 0.99 | 0.26 |
| Mg | 5.3 | 5.4 | 5.3 | 5.2 | 0.09 | 0.71 | 0.28 | 0.58 |
| Na | 8.0 | 8.0 | 8.3 | 8.0 | 0.3 | 0.61 | 0.61 | 0.72 |
| S | 1.1 | 1.1 | 1.0 | 1.0 | 0.03 | 0.25 | 0.003 | 0.17 |
| Microminerals, mg/kg | | | | | | | | |
| Sr | 81.8 | 418.9 | 94.3 | 440.2 | 18.7 | 0.0001 | 0.37 | 0.81 |
| Fe | 7.4 | 6.9 | 7.2 | 6.4 | 0.4 | 0.07 | 0.27 | 0.63 |
| Zn | 183.0 | 209.6 | 220.1 | 217.1 | 10.1 | 0.25 | 0.04 | 0.16 |
| Cr | 7.5 | 7.0 | 7.2 | 6.4 | 0.4 | 0.07 | 0.28 | 0.63 |
| Mn | 0.9 | 0.6 | 0.8 | 0.5 | 0.2 | 0.07 | 0.78 | 0.91 |

[1]Values are mean, n = 6. Phy: phytase.

Example 4

Further Examination of the Effects of Phytase on the Mechanical Strength of Bone The experiments in Examples 1-3 demonstrated a remarkable benefit of dietary supplemental microbial phytase to bone breaking strengths, mineral content, and mineral density of metatarsals and femurs (see also, Pagano et al, 2007)[63]. In those studies, *Escherichia coli* AppA2 phytase improved metatarsal and femur mechanical strength and chemical properties of weanling pigs fed a phosphorus-adequate diet. This phytase belongs to the histidine acid phosphatase (HAP) enzyme family[64] that initiates the stepwise removal of phosphate from phytate (myo-inositol hexakisphosphate), the major form of P in plant foods[65,66]. Although phytase has been increasingly used as a feed additive to improve dietary P utilization and to reduce manure P excretion by simple-stomached, food-producing animals fed plant-based, low-P diets[67], these results reveal a function of the enzyme, likely independent of P release, in improving bone development and function in P-adequate subjects.

First of all, it is of interest to determine whether supplemental dietary phytase still improves bone traits in animals fed a high P diet which exceeded their P nutrient requirement as effectively as in those fed only P-adequate diet in the study described in Examples 1-3. If so, the involvement of P release may be excluded from this action of phytase. Second, it is of interest to determine how the phytase-mediated improvements in bone mechanical and chemical properties observed in the experiments of Examples 1-3 are related to specific histological alterations. For long bones like femur, metacarpus and metatarsals, cartilage is a template for bone formation and as such plays an important role in morphogenesis, growth, and remodeling[68]. Sulfated proteoglycans are markers for the cellular phenotypes involved in the cartilage to bone transition[69], and are known to initially bind Ca and inhibit mineralization[70].

Osteogenesis involves a series of cellular and molecular events culminating in the fabrication of a mineralized matrix. Osteoblasts and osteoclasts interact at the progenitor level through signals that influence activation and differentiation during bone remodeling. The amount of osteoid deposition at the periosteal layer is one of the main indicators of measuring bone formation rate. Lastly, there are distinctive differences between cancellous and cortical bones in structure and metabolism[71,72]. However, the study of Examples 1-3 did not compare the effects of phytase on these two types of bones. Therefore, the studies described in Examples 4-8 were conducted to determine if supplemental phytase: 1) was still effective in improving bone properties in pigs fed a high P diet; 2) enhanced bone strength by promoting bone formation, sulfated proteoglycans synthesis, and bone mineralization; and 3) exerted different impacts on mineral profile of cancellous versus cortical bone. The results clearly demonstrate that supplemental dietary phytase improved bone structure and function of young pigs, regardless of the ample P supply in their diets. Independent of enhanced P release or deposition by phytase, the improvements were associated with increased osteoid formation in cortical bones and increased sulfated proteoglycans in trabecular bones. Most strikingly, the phytase supplementation resulted in up to 127-fold increase in strontium (Sr) concentrations in cancellous bone.

Materials and Methods Used in Examples 4-8 Experimental Design

As in Examples 1-3, the animal protocol was approved by Cornell Animal Care and Use Committee. An 8-week feeding trial was conducted at Cornell University Swine Research Farm. Thirty weanling pigs (Yorkshire×Hampshire×Landrace, body weight=8.6±0.5 kg) were allocated into three groups (n=10). Group 2 were fed a corn-soy basal diet (BD)+ 0.25% inorganic phosphorus (iP, dicalcium phosphate). Group 2 were fed BD+0.35% iP. Group 3 were fed BD+0.35% iP+3,400 units of phytase/kg (Escherichia coli appA2, OptiPhos, JBS United, Inc., Sheridan, Ind.). The BD (Table 7) contained adequate levels of all nutrients except for P[63], and 0.25% iP is the supplementation level recommended by NRC[24] to meet the P needs of this age of pigs. Because our previous experiment demonstrated a marginal benefit of 50 mg of Sr/kg of diet (SrCO$_3$ supplied by Alfa Aesar, Ward Hill, Mass.) to bone strength[63], all experimental diets were supplemented with the amount of Sr. Pigs were housed in an environmentally-controlled barn (20-25° C.; 12-light: 12-dark cycle), and given free access to feed and water.

Sample Collection

Growth performance of pigs was monitored at two week intervals. Blood samples of all individual pigs (fasted overnight for 8 h) were collected at initial (week 0) and then bi-weekly from the anterior vena cava using 5-mL heparin syringes to assay for concentrations of plasma iP[73], Ca and Sr[63]. At the end of experiment, 5 pigs (2 male and 3 female) from each group were killed by electrical stunning and exsanguination. Both left and front right legs from each animal were removed from the body.

Radiography and Mechanical Characterization

After the skin and major muscles were removed, two left legs were subjected to X-ray radiography using a Faxitron machine (Model 43855A; Hewlett Packard, McMinnville, Oreg., USA). Bone radiographs of femur and metacarpals were quantified by the kodac software. The software counted the total number of pixels. Thereafter, the 3rd and 4th metacarpals and femurs were collected to measure length, weight, height, and width after removing the remaining muscle and connective tissue. After the X-ray analysis, the two left legs were used for bone mechanical and mineral testing. Bone mechanical properties were determined by a three-point bending test (ASAE Standard S459 1992) using an Instron 4500 Machine Universal Testing Instrument (Model 1122, Instron, Canton, Mass.) with Instron Series IX Automated Materials Testing System Software (version 4.05). During testing, force was applied to the center of the bone held by supports 2.0 cm apart for metacarpals and 3.3 cm apart for femurs. The crosshead speed was set at 50 mm/min and the sampling rate was at 10 points/sec. The extrinsic parameters (stiffness/slope, maximum load, energy to break, maximum displacement) were derived from the force-displacement curve. Bone breaking strength was calculated with the adjustment of bone weight, and the average strength of the $3^{rd}$ and $4^{th}$ metacarpal was used as the metacarpal strength for each pig.

Cortical Bone Thickness and Mineral Analyses

After the above mechanical tests, midshaft sections of both femur and metacarpus were cut and washed with de-ionized water. The cortical thickness of both bones was measured by slide caliper in the midshaft. Cortical and cancellous bones were separated for total ash and mineral analysis. A 3-cm long and 3-mm thick midshaft of femur and 1-cm long and 1.5-mm thick midshaft of metacarpus were used for cortical ash analysis. For cancellous bone, sponge-like bone from 3-cm below the growth plate of femur and 1.5-cm below the growth plate of metacarpus were collected. For ash analysis, bones were oven-dried at 110° C. for 24 h, and incinerated in a muffle furnace at 550° C. for 96 h. Concentrations of individual elements in the ash were measured using inductively coupled argon plasma spectrophotometer (ICAP 61E Trace Analyzer, Thermo Jarell Ash corporation, Franklin, Mass.)[63], and were expressed on ash basis.

Histology and Histomorphometry of Bone Formation, Osteoid, Mineralization, and Sulfated Proteoglycans Metacarpals ($4^{th}$) from right foot of pigs (n=5 for each group) were quickly fixed by 10% formalin for histology, decalcified, embedded in paraffin sagittally serially sectioned through the midline (8 μm), and stained with Masson's trichrome as previously described[74]. Variation of bone matrix mineralization was detected by modified tetrachrome method[75]. Sulfated proteoglycans were detected by alcian blue staining[76] and counter staining with Mayer's acid haematoxylin. PCI software—CIMAGING System (Model 1280, Compix Inc., Cranberry, Pa.)—was applied to measure bone surface, osteoid, bone volume, trabecular thickness, number, and separation, and proteoglycans surface. Trabecular size and separation distances were measured by the software measurement scale. Trabecular numbers were counted within a specified field. For proteoglycans measurement, the total area of trabecular bone was first captured to define the region of interest (ROI). Then, within the ROI the blue color area of proteoglycans was captured and its area measured to define the object area. For osteoid measurement, the first cortical bone surface was the object. The area fraction of the deep green in the periosteal area was expressed as: Area fraction (%)=Object area/Region of interest (ROI)×100.

Statistical Analysis

Data were analyzed using one-way ANOVA in Graph Pad Prism 3.0. The Bonferroni t test was used for mean comparisons. Data are presented as group means (n=5 or 10). Significance level was set at P<0.05.

Example 5

Effects of Phytase on the Mechanical Properties of Bone

Figure 3A:
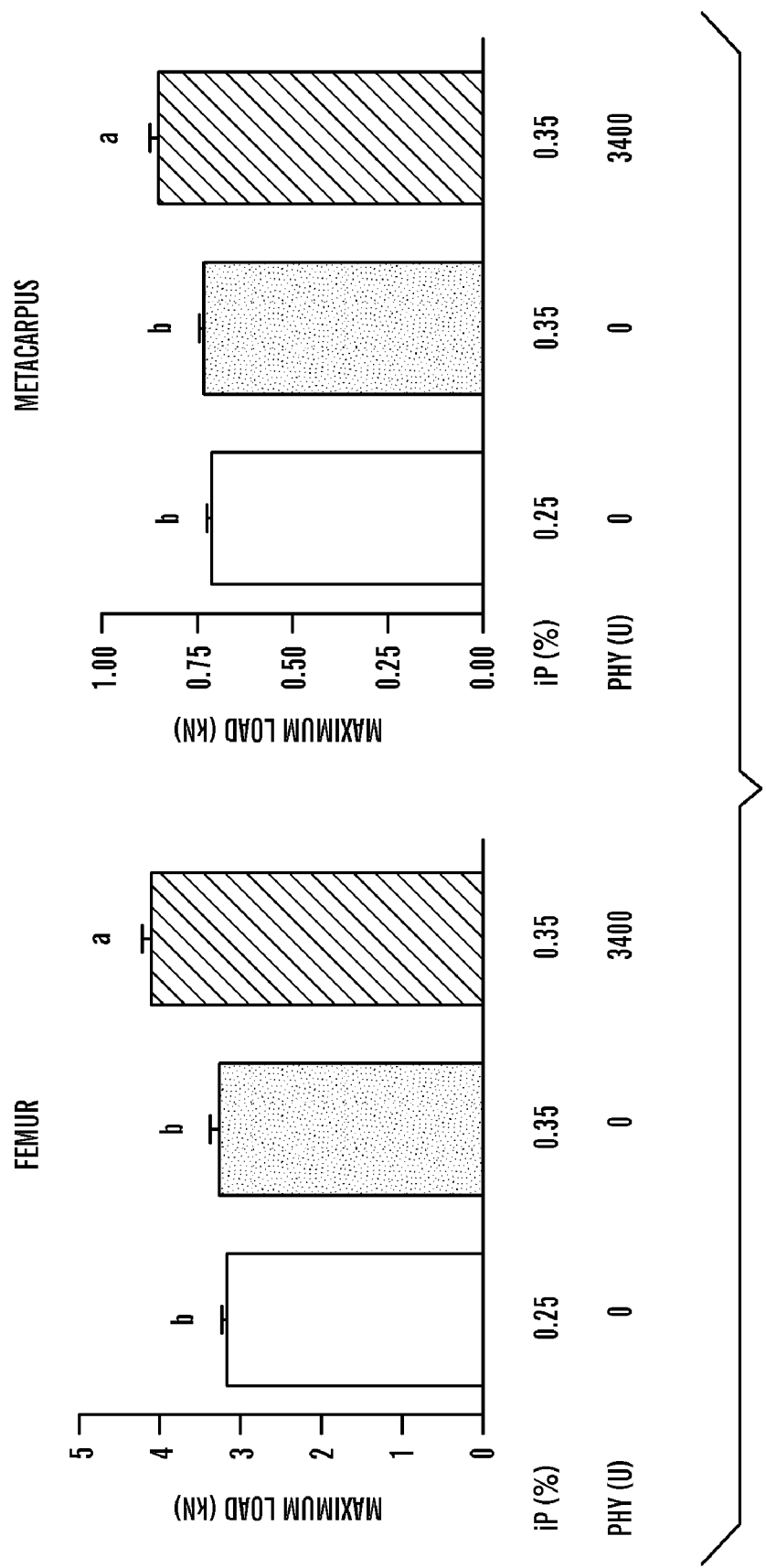
FIG. 3 shows the effects of supplemental phytase on femoral and metacarpal: (A) maximum bone breaking load; (B) energy to break; (C) stiffness; and (D) cortical thickness (Ct.
Figure 3B:
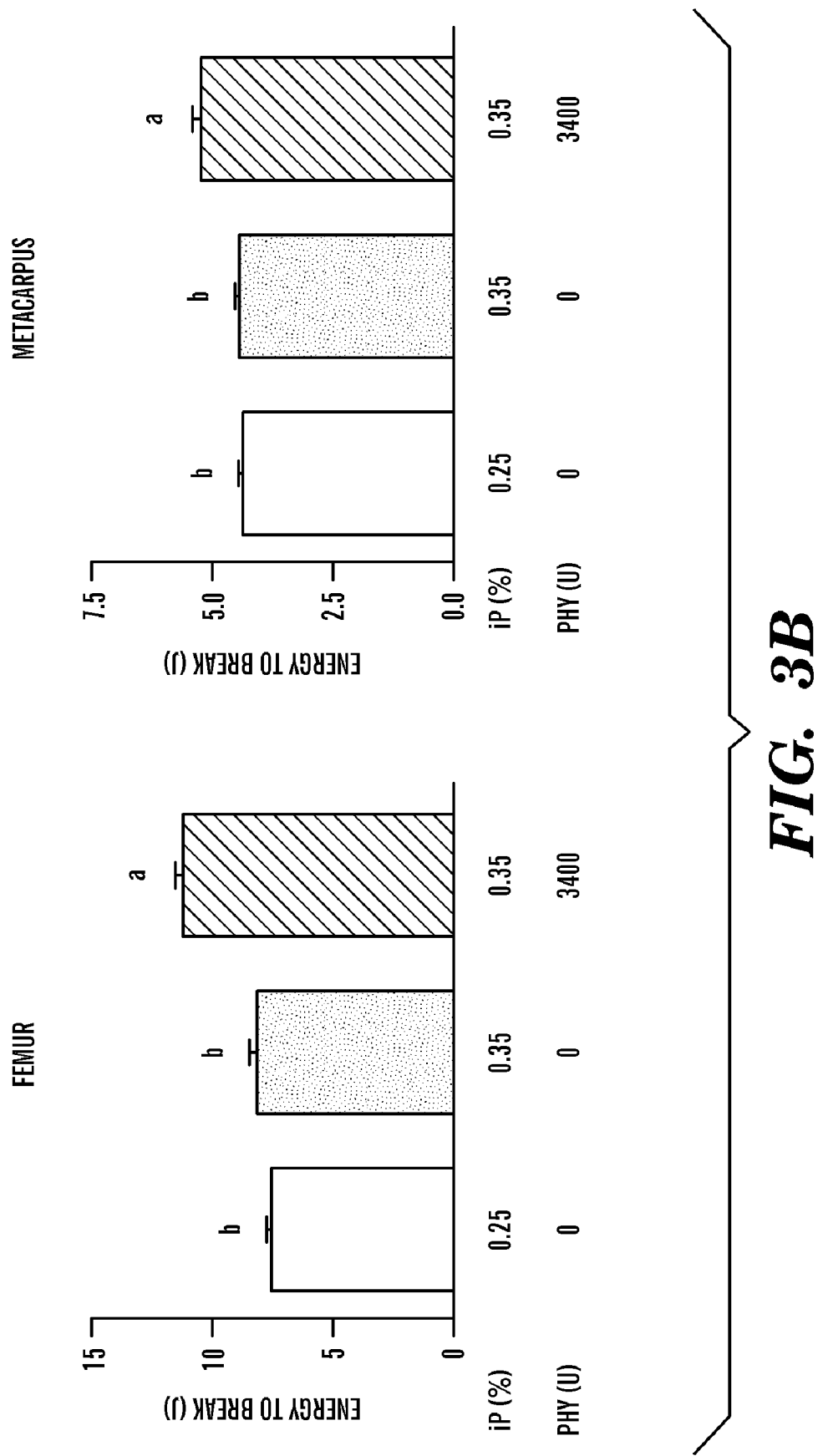
Figure 3C:
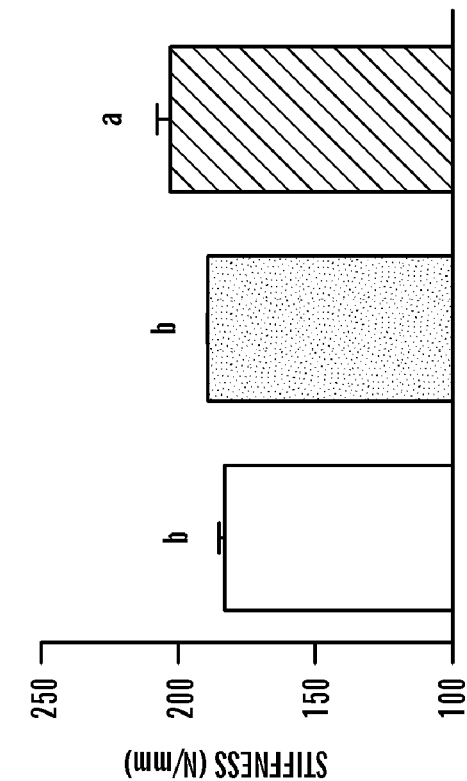
Figure 3C:
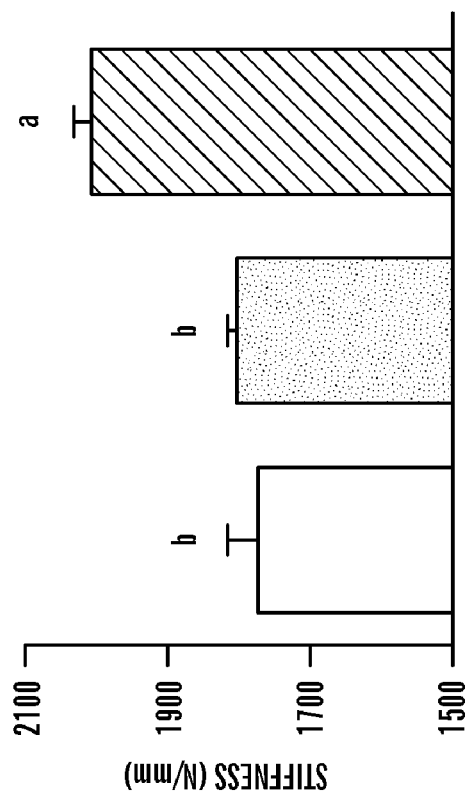
Figure 3D:
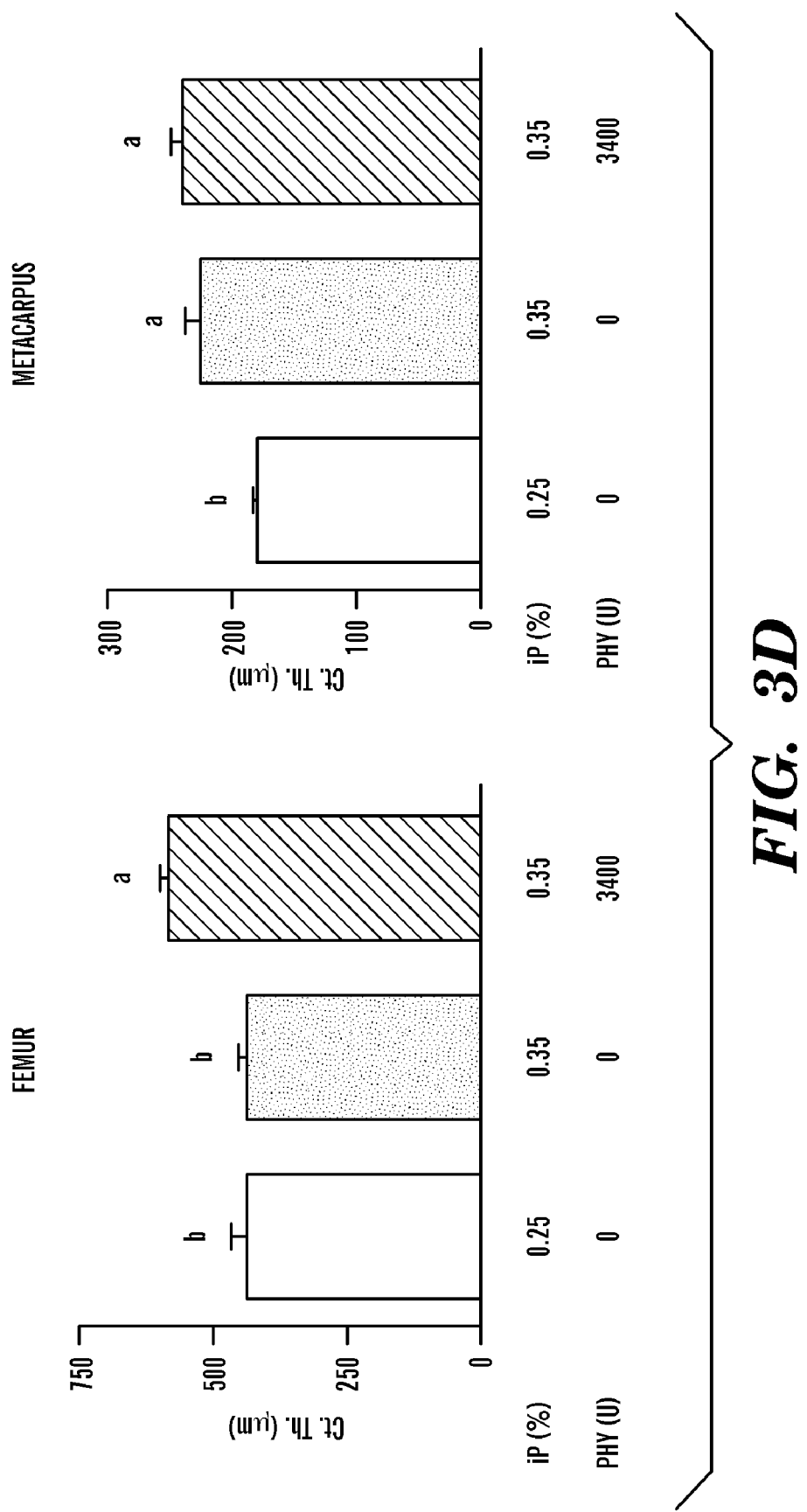

Given the same level of dietary iP (0.35%), pigs fed phytase had greater (P<0.05) maximal load (FIG. 3A, by 38 and 20%), energy to break (FIG. 3B, by 26 and 14%), stiffness (FIG. 3C, by 12 and 8%), and cortical bone thickness (FIG. 3D, by 32 and 7%) of both femur and metacarpus, respectively. In contrast, increasing dietary iP from 0.25 to 0.35% did not produce significant changes in these parameters except for a 19% increase in metacarpal thickness. Meanwhile, body weight, plasma inorganic P, Ca and Sr concentrations of pigs were not significantly affected by the dietary treatments (Table 8). Although phytase supplementation tended to enhance femoral and (or) metacarpal length, weight, height, and width, the changes were not statistically significant (Tables 9 and 10). The femoral cross sectional areas were not different among treatment groups.

Example 6

Effects of Phytase on Bone Density

On the basis image pixel numbers of radiograph, phytase improved (P<0.001) femur and metacarpus bone density by 28 and 20%, respectively, compared with that of pigs fed only 0.35% iP (FIGS. 4A and 4B). This was confirmed by the histological assessment in metacarpal bone (FIG. 4C). Pigs fed phytase displayed 38% increase (P<0.001) in metacarpal bone volume than those fed only 0.35% iP. There was no such difference between pigs fed 0.25 and 0.35% iP.

Example 7

Figure 5A:
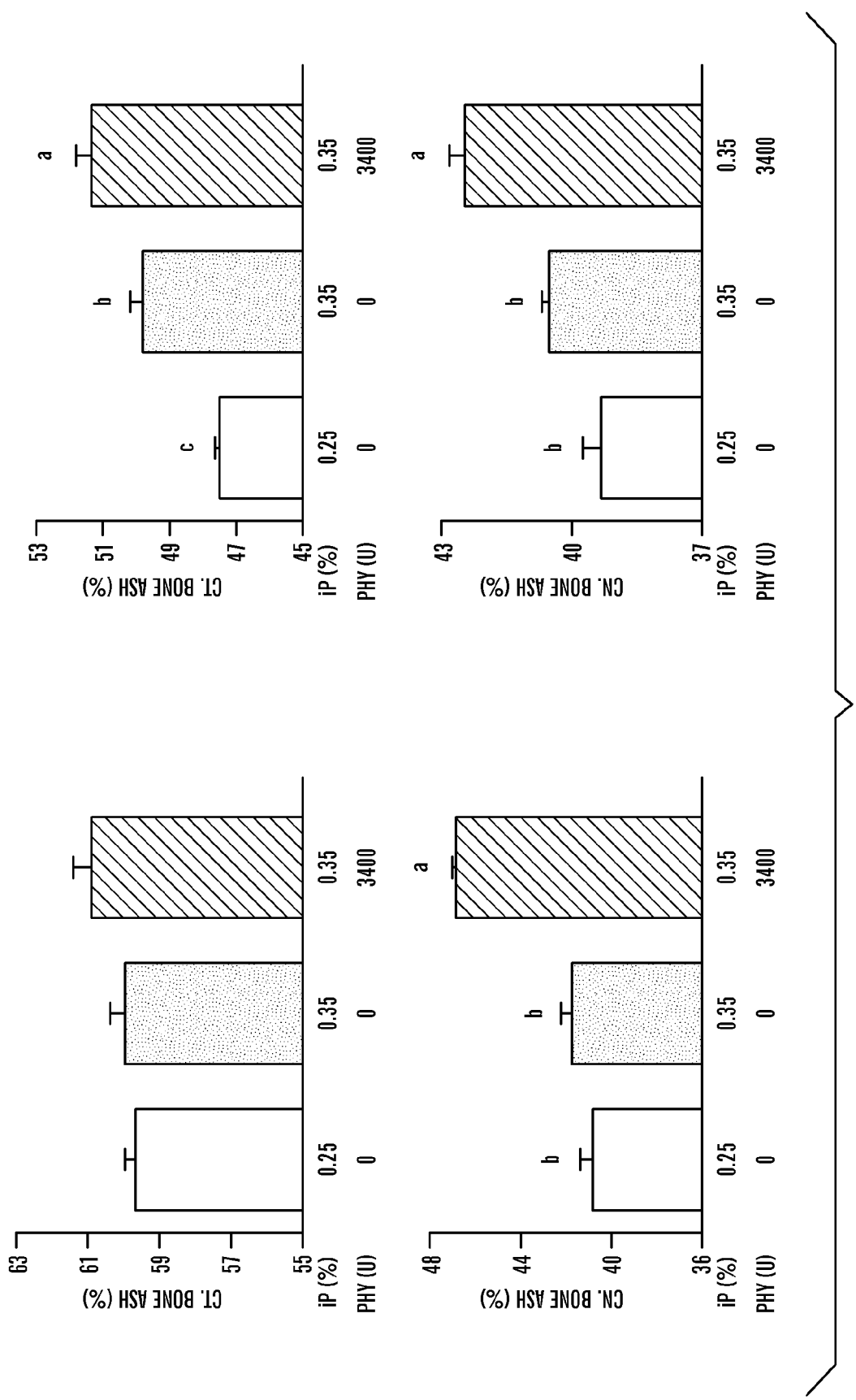
Figure 5B:
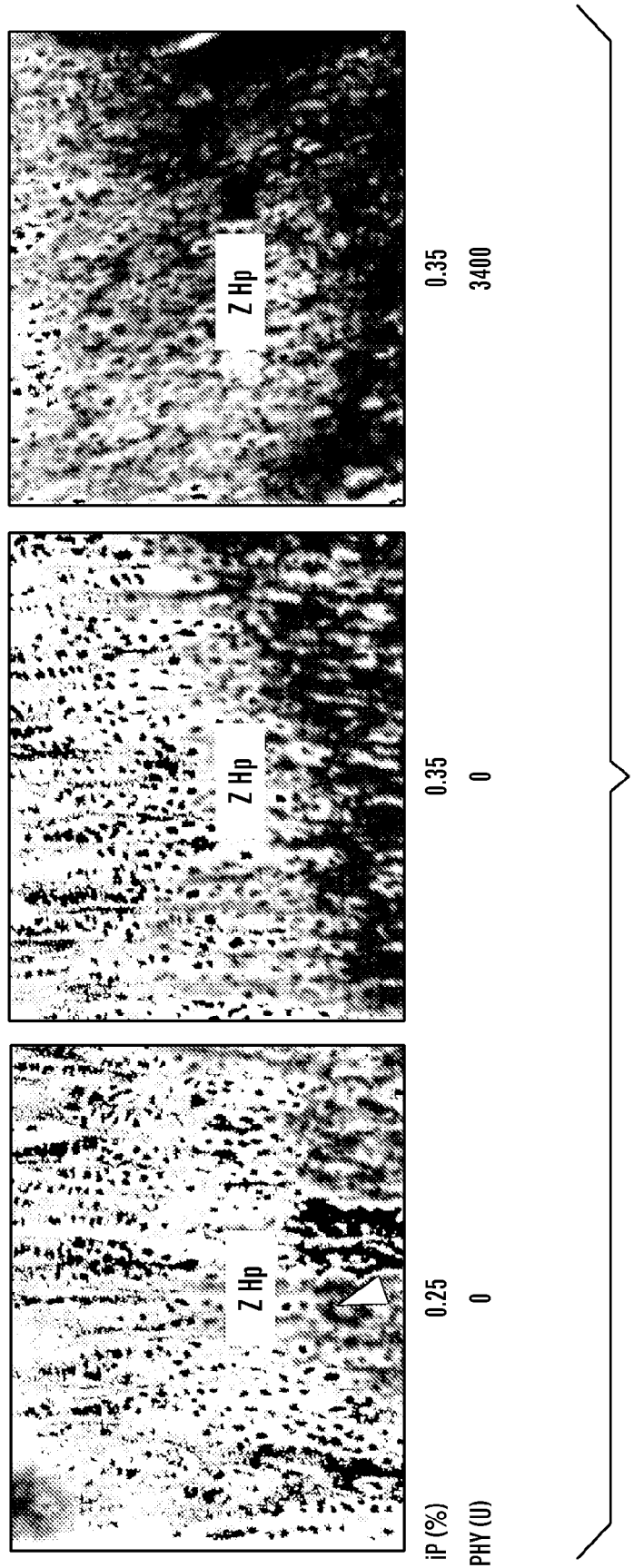
Figure 5C:
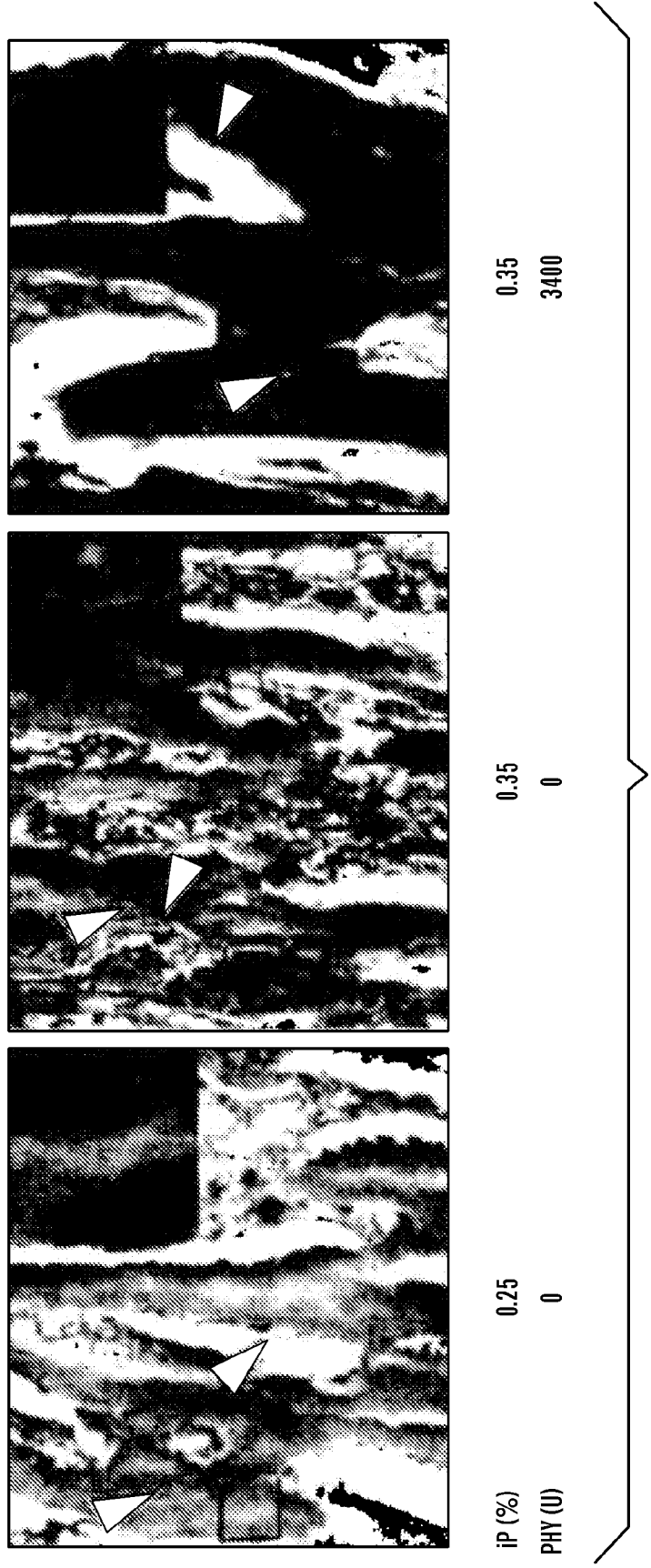

Effects of Phytase on Epiphyseal Mineralization, Bone Ash, and Bone Mineral Profile Total ash concentration of cortical bone was not altered in femurs, but increased by 3% in (P<0.01) in metacarpals by phytase (FIG. 5A). The cancellous bone ash of femur and metacarpus were enhanced (P<0.01) by 12 and 5%, respectively (FIG. 5B). On the contrary, increasing iP from 0.25 to 0.35% resulted in only increase in cortical bone ash of metacarpals. There was a tendency of higher mineralization at the epiphyseal growth plate (FIG. 5B). Phytase supplementation increased red color density in the cartilage hypertrophy zone, reflecting a high accumulation of mineral. Expanding from the growth plate toward the newly formed cancellous bone, more mineralized bone was observed by phytase supplementation (FIG. 5C). In cortical bones, dietary phytase resulted in only reductions (P<0.02) of S and Sr concentrations in both femur and metacarpus, compared with those of 0.35% iP diet (Table 11). In cancellous bones, Ca and P concentrations were decreased by 11 to 19% and 22 to 31% in femur and metacarpus by dietary phytase supplementation, respectively (Table 12). Concentrations of Na, Mg, and S were reduced by phytase supplementation in one or both of bones. While dietary phytase resulted in 33 and 22% increase (P<0.05) in Fe concentration of femur and metacarpus, respectively, the effect on Zn or Cr was not consistent or significant in the two bones. Most strikingly, Sr concentration in femur and metacarpus was elevated (P<0.002) 127- and 115-fold, respectively, by dietary phytase supplementation.

Example 8

Effects of Phytase on Bone Formation and Sulfated Proteoglycans

Supplementing phytase into the 0.35% iP diet resulted in (P<0.05) 51% increase in trabecular thickness, 37% decrease in trabecular separation, and thereby 42% increase in trabecular density (FIG. 6A). Similarly, phytase supplementation enhanced (P<0.001) the osteoid thickness (osteoid layer per unit of bone) in the periosteal area by 60% (FIG. 6B), indicating elevated bone matrix growth. Concentrations of sulfated proteoglycans in cancellous bone were increased by 18% (P<0.001) by dietary phytase (FIG. 6C). In addition, sulfated proteoglycans were more aggregated in pigs fed phytase than in pegs fed only 0.35% iP. On the contrary, all these parameters in the three panels were not affected by increasing iP from 0.25 to 0.35% in diets.

The results of the studies described in Examples 4-8 clearly demonstrate the effectiveness of supplementing E. coli AppA2 phytase in improving bone structure and function of pigs fed diets containing more than adequate P. Compared with pigs fed 0.35% iP, the phytase-fed pigs displayed consistent improvements in mechanical strength (maximal load, energy to break, stiffness, cortical bone thickness, and bone density and volume), material property (bone ash content and mineralization), and histological architecture (increased osteoid in cortical bone, increased enchnodral bone formation, and increased sulfated proteoglycans in cancellous bone). Three lines of evidence support that the observed benefits of phytase are a novel function of the enzyme in bone metabolism, independent of its well-documented role in liberating P from phytate as reported previously in animals fed low-P diets[77,34]. First of all, these benefits were not produced by increasing iP in the diets from 0.25 to 0.35%, and thus were not driven by dietary P availability per se. Second, supplementing 0.1% iP and(or) phytase into the 0.25% iP diet caused no increase in body weight, plasma inorganic P and Ca concentrations, or bone P and Ca concentrations of pigs, indicating that 0.25% iP was able to provide sufficient P for pigs to maintain P adequacy. Third, the weight and size of each tested bone in all groups remained nearly identical. It is unlikely that the increased bone strength resulted from increased bone size due to improved P nutrition.

Histological analyses of the metacarpal bone provide structural and chemical bases to explain how supplemental phytase improved bone function. Compared with pigs fed only 0.35% iP, pigs fed phytase had enhanced periosteal osteoid formation, trabecular bone density, bone volume, sulfated proteoglycans accumulation, and bone mineralization. Because bone strength is a function of bone geometry, composition and quality of bone matrix, minerals and their distribution, and intrinsic properties of bony tissue[78], the combined changes in bone histological and material properties mediated by phytase supplementation were translated into enhancement of bone mechanical strength. The histomorphometric data showed that phytase supplementation promoted perichondral bone formation by cartilage replacement and the intramembranous bone formation by the accumulation of matrix. Specifically, the increased cortical thickness in the phytase-fed pigs was related to a greater osteoid amount and the increased bone volume was related to a higher trabecular bone density. Because a high amount of osteoid is often associated with a low percentage of bone ash and low bone strength[79] the concurrent existence of high bone strength and high osteoid amount in the phytase-fed pigs might be due to a complementary change in the collagen fiber composition for bone mineralization that showed no blockage of collagen cross-linking[80,81]. The high sulfated proteoglycans accumulation in trabecular bone of pigs fed phytase, measured by alcian blue staining, is consistent with the intensity of red color staining in cartilage hypertrophy zone of epiphyseal growth plate, the greater amount of bone ash, and the thicker trabecular density. Again, while not wishing to be bound by theory, this array of changes suggests that phytase enhanced enchondral bone formation. A presumed faster transformation of cartilage into bone might subsequently cause denser sulfated proteoglycans in trabecular bone. A high rate of mineralization in the hypertrophic cartilage has been shown to enhance fabrication of a mineralized matrix, producing a stronger bone[82]. Aggregation of sulfated proteoglycans in trabecular bones of pigs fed phytase indicates that this enzyme may have a potential role in up-regulating glycosaminoglycan synthesis[94].

It is most remarkable that feeding pigs with supplemental phytase resulted in >100-fold increases in Sr concentration in cancellous bones of femur and metacarpus, compared with those fed only 0.35% iP. Again, while not wishing to be bound by theory, several lines of evidence indicate that the accumulation of Sr in cancellous bone is selective and represents a novel function of the enzyme in regulating bone mineral metabolism. First of all, the phytase-fed pigs did not have any extra Sr ingestion than the other groups of pigs because by analysis Sr concentration in the three experimental diets was 55 to 58 mg/kg and in the phytase preparation was only 1.4 mg/kg. Second, plasma Sr concentrations in pigs fed phytase were not different from those of other groups of pigs. Thus, enhanced absorbed Sr by phytase, if any, either was rapidly excreted[84] or diffused through the Haversian capillaries into bone extracellular fluid[85] and deposited into the cancellous bone[84]. Third, supplemental phytase actually decreased Sr concentration of cortical bones in both femur and metacarpus. While not wishing to be bound by theory, the opposite changes in Sr concentrations between the two types of bones suggest a plausible mobilization or re-distribution of the element from the cortical to the cancellous bone[86,87]. If so and there was a balance between these two pools of Sr, the relatively lower decreases in cortical Sr concentrations, compared with those increases in cancellous bone, might be attributed to the much greater total mass of cortical fraction in the whole bone. This also explains why such tremendous effect of phytase on Sr concentration in the whole bone of femur and metacarpus[63] was not observed. Fourth, the accumulation of Sr in cancellous bones in the phytase-fed pigs concurred with a substantial decrease in concentrations of Ca and P, along with Mg, Na, and S. In fact, the total absolute decrease of these five macro-elements was very close to that of the increase of Sr in femur. That replacement is consistent with the notion that Sr accumulates in the bone mainly by ionic substitution[88].

The selective accumulation of Sr in the cancellous bone in the present study was implicated with the structural and functional improvements of bones by phytase. As Sr exists in higher concentrations in newly formed bone[42], it stimulates pre-osteoblast replication by cation sensing[89], leading to an increased matrix synthesis[90] and cartilage matrix formation[46]. Indeed, the phytase-fed pigs had higher amount of osteoid in the periosteal bone surface and high trabecular bone. Furthermore, Sr has been shown to enhance bone mechanical resistance in rats[22] and bone density in chickens[91]. Consistent with this, phytase supplementation also rendered similar improvements in bone strength in the present study. Overall, there was a strong positive correlation between bone traits and Sr in cancellous bone in the phytase-fed pigs. Thus, while not wishing to be bound by theory, phytase might exert its impact on bone metabolism by modulating Sr distribution in cancellous bones. Although the mechanism by which phytase affects bone Sr remains unclear at the present time, the release of inositol phosphates (IP) from the hydrolysis of phytate (inositol hexaphosphate, IP6) may be a distinct candidate. The experimental diets contained relatively high levels of phytate concentration (1%)[92]. Despite the amount of inorganic P in the diets, the high level of supplemental phytase was still able to catalyze the stepwise dephosphorylation of phytate, producing a series of intermediate products (IP1, IP2, IP3, IP4, IP5, and IP6) that are readily absorbed from the gut and distributed into tissues[93]. These compounds have been shown to act as second messenger in intracellular signal transduction[94]. In particular, IP3 affects intracellular calcium ($Ca^{2+}$) mobilization. While not wishing to be bound by theory, if IP3 reached cancellous bone, it could induce the mobilization of Ca and other macroelements, and consequently render the accumulation of Sr through ionic replacement[88]. The present study unveils a function of phytase in altering bone Sr metabolism to improve bone integrity and function. The overall benefits of supplemental phytase to bone anabolism in the young pigs offers a new strategy to enhance peak bone mass at early life stage for reducing risk of osteoporosis in elderly humans. Similar benefits of phytase supplementation on bone health and strength, with or without concurrent strontium supplementation, are specifically contemplated in adult humans. In addition to the supplementation of phytase, with or without supplemental strontium, it can be advantageous to ensure a sufficient level of phytate or phytic acid and related metabolites (e.g., IP5, IP4, IP3, IP2 and IP1) as substrate(s) for the supplemental phytase. While not wishing to be bound by theory, providing phytate or phytic acid as substrate for the supplemental phytase can permit the generation of inositol phosphate intermediates, including, for example, IP3, which can have effects as discussed above. Thus, in one aspect, phytate or phytic acid supplementation is also provided, e.g., as a dietary supplement. Such supplementation can be achieved through administration of a composition or compositions comprising supplemental phytic acid, including, for example, a composition comprising supplemental phytic acid or phytate and supplemental strontium, or even, for example, a composition comprising supplemental phytic acid or phytate, supplemental strontium and phytase enzyme (in dry form, for example, the enzyme in such a composition would not be expected to catalyze hydrolysis of the phytate or phytic acid).

It is to be understood and expected that variations in the principles of invention herein disclosed may be made by one skilled in the art and it is intended that such modifications are to be included within the scope of the present invention.

TABLE 7

COMPOSITION OF BASAL DIET

| Ingredient | % |
|---|---|
| Corn | 65.2 |
| Soybean meal, 48% CP | 28.0 |
| Plasma protein | 2.0 |
| Limestone | 1.1 |
| Dicalcium Phosphate | 1.4 |
| Corn Oil | 1.0 |
| Lys HCl | 0.1 |
| Vitamin/mineral Premix[1] | 0.2 |
| $MgO_4$ | 0.06 |

TABLE 7-continued

COMPOSITION OF BASAL DIET

| | % |
|---|---|
| Tylan 10 | 0.5 |
| Salt | 0.5 |
| Composition[2] | |
| Energy (Kcal ME/Kg) | 3,262 |
| Crude protein[2] | 20.30 |
| Ca | 0.80 |
| P (total) | 0.66 |
| P (available) | 0.35 |
| Ca:P (total) | 1.24 |

[1]Vitamin and mineral premix provided/kg diet: retinyl palmitate, 1208 µg; ergocalciferol, 5.5 µg; dl-α-tocopheryl acetate, 10.72 mg; menadione, 0.5 mg; d-biotin, 0.05 mg; choline chloride, 0.5 g; folic acid, 0.3 mg; niacin, 15 mg; Ca-D-panthothenate, 10 mg; riboflavin, 3.5 mg; thiamin 1 mg; pyridoxine, 1.5 mg; Cyanocobalamin, 17.5 µg; $CuSO_4 \cdot 5H_2O$, 6 mg; $C_2H_8N_2HI$, ethylene diamine dihydroiodide, 0.14 mg; MnO, 4 mg; $Na_2SeO_3$, 0.3 mg; ZnO, 100 mg.
[2]Calculated based on NRC.
Strontium level in the diets was analyzed and ranged from 55-58 mg/Kg.

TABLE 8

EFFECTS OF SUPPLEMENTAL DIETARY PHYTASE ON GROWTH AND PLASMA MINERAL CONCENTRATIONS OF PIGS

| | iP (%) | | | | |
|---|---|---|---|---|---|
| | 0.25 | 0.35 | 0.35 | | |
| | | Phytase (U) | | | |
| | 0 | 0 | 3400 | SE | P < |
| Body weight (Kg) | | | | | |
| 0 Week | 8.7 | 8.6 | 8.7 | 0.5 | 1.0 |
| 8 Week | 47.6 | 49.7 | 50.4 | 2.3 | 0.7 |
| Plasma iP (mg/L) | | | | | |
| 0 Week | 69 | 72 | 77 | 2.3 | 0.6 |
| 8 Week | 82 | 84 | 89 | 1.8 | 0.7 |
| Plasma Ca (mg/L) | | | | | |
| 0 Week | 104 | 102 | 106 | 2.2 | 0.5 |
| 8 Week | 124 | 120 | 123 | 4.1 | 0.7 |
| Plasma Sr (µg/L) | | | | | |
| 0 Week | 189 | 177 | 172 | 11.9 | 0.4 |
| 8 Week | 246 | 261 | 280 | 13.2 | 0.4 |

The values are expressed as means of pigs (n = 10).

TABLE 9

EFFECTS OF SUPPLEMENTAL DIETARY PHYTASE ON FEMURAL MECHANICAL PROPERTIES

| | iP (%) | | | | |
|---|---|---|---|---|---|
| | 0.25 | 0.35 | 0.35 | | |
| | | Phytase (U) | | | |
| | 0 | 0 | 3400 | SE | P < |
| Cross-sectional area, mm[2] | 211.7 | 204.6 | 199.7 | 13.7 | 0.9 |
| Length (mm) | 142.7 | 142.4 | 143.7 | 5.6 | 1.0 |
| Weight (g) | 193.2 | 194.2 | 202.2 | 3.7 | 0.2 |
| Height (mm) | 20.6 | 20.2 | 21.8 | 1.5 | 0.7 |
| Width (mm) | 21.1 | 21.1 | 23.3 | 1.2 | 0.9 |
| Max. Displacement (mm) | 5.7 | 5.1 | 4.9 | 0.7 | 0.7 |

The values are expressed as mean (n = 5).

TABLE 10

EFFECTS OF SUPPLEMENTAL DIETARY PHYTASE ON METACARPAL MECHANICAL PROPERTIES

| | iP (%) | | | | |
|---|---|---|---|---|---|
| | 0.25 | 0.35 | 0.35 | | |
| | | Phytase (U) | | | |
| | 0 | 0 | 3400 | SE | P < |
| Length (mm) | 58.1 | 58.8 | 60.5 | 2.6 | 0.8 |
| Weight (g) | 17.7 | 17.8 | 19.2 | 1.7 | 0.8 |
| Height (mm) | 15.0 | 14.4 | 14.8 | 0.9 | 0.9 |
| Width (mm) | 14.1 | 14.8 | 15.0 | 1.5 | 0.9 |
| Max. Displacement (mm) | 9.6 | 9.0 | 8.9 | 1.8 | 1.0 |

The values are expressed as mean (n = 5).

TABLE 11

EFFECTS OF SUPPLEMENTAL DIETARY PHYTASE ON FEMORAL AND METACARPAL COMPACT BONE MINERAL PROFILE

| | iP (%) | | | | |
|---|---|---|---|---|---|
| | 0.25 | 0.35 | 0.35 | | |
| | | Phytase (U) | | | |
| | 0 | 0 | 3400 | SE | P ≤ |
| Femur | | | | | |
| Macro-mineral (g/Kg ash) | | | | | |
| Ca | 410.0 | 400.0 | 403.0 | 5.08 | 0.36 |
| P | 204.0 | 201.0 | 199.0 | 3.39 | 0.58 |
| Mg | 7.5 | 7.6 | 7.6 | 0.11 | 0.78 |
| Na | 9.8 | 9.8 | 9.4 | 0.15 | 0.18 |
| Micro-minerals (mg/kg ash) | | | | | |
| S* | 753.4[a] | 728.3[a] | 649.9[b] | 15.82 | 0.02 |
| Sr | 730.2[a] | 687.2[a] | 568.8[b] | 9.91 | 0.0001 |
| Fe | 20.9 | 23.9 | 25.1 | 3.63 | 0.13 |
| Cr | 12.2 | 12.8 | 12.6 | 0.73 | 0.82 |
| Zn | 258.4 | 259.9 | 278.8 | 13.95 | 0.17 |
| Metacarpus | | | | | |
| Macro-mineral (g/Kg ash) | | | | | |
| Ca | 419.0 | 400.0 | 398.0 | 5.97 | 0.07 |
| P | 207.0 | 228.0 | 195.0 | 17.60 | 0.43 |
| Mg | 7.4 | 8.5 | 7.2 | 0.60 | 0.31 |
| Na | 9.8 | 10.3 | 8.6 | 0.81 | 0.34 |
| Micro-minerals (mg/kg ash) | | | | | |
| S* | 1196.4[a] | 1035.2[a] | 763.8[b] | 55.31 | 0.002 |
| Sr | 739.5[a] | 835.5[a] | 541.4[b] | 51.73 | 0.01 |
| Fe | 26.4 | 27.1 | 24.7 | 5.79 | 0.18 |
| Cr | 12.1 | 15.1 | 13.3 | 1.23 | 0.29 |
| Zn | 294.1 | 319.2 | 307.7 | 19.84 | 0.68 |

The values are expressed as means of pigs (n = 5). Means with different letters in the same row differ (P < 0.05).
*Listed in the micro-mineral category due to its low concentration in bone.

TABLE 12

EFFECTS OF SUPPLEMENTAL DIETARY PHYTASE ON FEMORAL AND METACARPAL CANCELLOUS BONE MINERAL PROFILE

| | iP (%) | | | | |
|---|---|---|---|---|---|
| | 0.25 | 0.35 | 0.35 | | |
| | | | Phytase (U) | | |
| | 0.0 | 0.0 | 3400 | SE | P ≦ |
| Femur | | | | | |
| Macro-mineral (g/Kg ash) | | | | | |
| Ca | 396.0$^a$ | 350.0$^a$ | 311.0$^b$ | 16.33 | 0.003 |
| P | 198.0$^a$ | 198.0$^a$ | 155.0$^b$ | 5.54 | 0.0007 |
| Mg | 7.5$^a$ | 7.9$^a$ | 6.0$^b$ | 0.18 | 0.0001 |
| Na | 10.0$^a$ | 9.8$^a$ | 8.3$^b$ | 0.213 | 0.0007 |
| Micro-minerals (mg/kg ash) | | | | | |
| S* | 2211.4$^a$ | 1986.4$^b$ | 1833.2$^b$ | 41.99 | 0.007 |
| Sr | 900.2$^b$ | 736.8$^b$ | 93680.7$^a$ | 7848.47 | 0.0001 |
| Fe | 52.6$^b$ | 56.8$^b$ | 75.6$^a$ | 6.96 | 0.005 |
| Cr | 11.7 | 13.3 | 10.0 | 0.90 | 0.09 |
| Zn | 308.3$^b$ | 338.2$^b$ | 395.7$^a$ | 10.67 | 0.05 |
| Metacarpus | | | | | |
| Macro-mineral (g/kg ash) | | | | | |
| Ca | 411.0$^a$ | 408.0$^a$ | 329.0$^b$ | 12.55 | 0.002 |
| P | 209.0$^a$ | 232.0$^a$ | 161.0$^b$ | 10.41 | 0.002 |
| Mg | 7.2 | 8.4 | 6.0 | 0.65 | 0.10 |
| Na | 9.5$^a$ | 11.9$^a$ | 7.6$^b$ | 0.85 | 0.02 |
| Micro-minerals (mg/kg ash) | | | | | |
| S* | 1534.6$^a$ | 1668.0$^a$ | 1334.5$^b$ | 51.26 | 0.002 |
| Sr | 718.2$^b$ | 749.0$^b$ | 86221.0$^a$ | 6406.24 | 0.0001 |
| Fe | 58.0$^b$ | 54.4$^b$ | 66.4$^a$ | 20.05 | 0.003 |
| Cr | 11.6 | 13.6 | 10.7 | 0.95 | 0.13 |
| Zn | 339.1 | 359.7 | 334.3 | 22.65 | 0.71 |

The values are expressed as means of pigs (n = 5). Means with different letters in the same row differ (P < 0.05).
*Listed in the micro-mineral category due to its low concentration in bone.

LITERATURE CITED

1) Alffram, P. A. & Bauer, G. C. Epidemiology of fractures of the forearm. A biomechanical investigation of bone strength. J Bone Joint Surg Am. 1962; 44-A:105-14.
2) Cohen, A. J. & Roe, F. J. Review of risk factors for osteoporosis with particular reference to a possible aetiological role of dietary salt. Food Chem. Toxicol. 2000; 38:237-53.
3) Consensus development conference: diagnosis, prophylaxis, and treatment of osteoporosis. Am J. Med. 1993; 94:646-50.
4) Cooper, C., Campion, G. & Melton, L. J., 3rd Hip fractures in the elderly: a world-wide projection. Osteoporos Int. 1992; 2:285-9.
5) Wasnich, R. (1999) Epidemiology of osteoporosis, 4th ed. Lippincott Williams & Wilkins, New York, N.Y.
6) Matkovic, V., Jelic, T., Wardlaw, G. M., Ilich, J. Z., Goel, P. K., Wright, J. K., Andon, M. B., Smith, K. T. & Heaney, R. P. Timing of peak bone mass in Caucasian females and its implication for the prevention of osteoporosis. Inference from a cross-sectional model. J Clin Invest. 1994; 93:799-808.
7) Heaney, R. P., Abrams, S., Dawson-Hughes, B., Looker, A., Marcus, R., Matkovic, V. & Weaver, C. Peak bone mass. Osteoporos Int. 2000; 11:985-1009.
8) Thompson, D. D., Simmons, H. A., Pirie, C. M. & Ke, H. Z. FDA Guidelines and animal models for osteoporosis. Bone. 1995; 17:125 S-33S.
9) Aerssens, J., Boonen, S., Lowet, G. & Dequeker, J. Interspecies differences in bone composition, density, and quality: potential implications for in vivo bone research. Endocrinol. 1998; 139:663-70.
10) Masse, P. G., Dosy, J., Tranchant, C. C. & Dallaire, R. Dietary macro- and micronutrient intakes of nonsupplemented pre- and postmenopausal women with a perspective on menopause-associated diseases. J Hum Nutr Diet. 2004; 17:121-32.
11) Miller, S. C., Bowman, B. M. & Jee, W. S. Available animal models of osteopenia—small and large. Bone. 1995; 17:117 S-23S.
12) Lei, X. G. & Stahl, C. H. Nutritional benefits of phytase and dietary determinants of its efficacy. J Appl Anim Res. 2000; 17:97-112.
13) Murry, A. C., Lewis, R. D. & Amos, H. E. The effect of microbial phytase in a pearl millet-soybean meal diet on apparent digestibility and retention of nutrients, serum mineral concentration, and bone mineral density of nursery pigs. J Anim Sci. 1997; 75:1284-91.
14) Gentile, J. M., Roneker, K. R., Crowe, S. E., Pond, W. G. & Lei, X. G. Effectiveness of an experimental consensus phytase in improving dietary phytate-phosphorus utilization by weanling pigs. J Anim Sci. 2003; 81:2751-7.
15) Young, L. G., Leunissen, M. & Atkinson, J. L. Addition of microbial phytase to diets of young pigs. J Anim Sci. 1993; 71:2147-50.
16) Vohra, P., Gray, G. A. & Kratzer, F. H. Phytic acid-metal complexes. Proc Soc Exp Biol Med. 1965; 120:447-9.
17) Cromwell, J. Phytase appears to reduce phosphorus in feed, manure. Feedstuffs. 1991; 63:14-6.
18) Yi, Z., Komegay, E. T., Ravindran, V., Lindemann, M. D. & Wilson, J. H. Effectiveness of Natuphos phytase in improving the bioavailabilites of phosphorus and other nutrients in soybean meal-based semipurified diets for young pigs. J Anim Sci. 1996; 74:1601-11.
19) Pond, W. & Houpt, K. (1978) The biology of the pig, 1st ed. Comstock Pub. Associates, Ithaca, N.Y.
20) Canalis, E., Hott, M., Deloffre, P., Tsouderos, Y. & Marie, P. J. The divalent strontium salt S12911 enhances bone cell replication and bone formation in vitro. Bone. 1996; 18:517-23.
21) Meunier, P. J., Roux, C., Seeman, E., Ortolani, S., Badurski, J. E., Spector, T. D., Cannata, J., Balogh, A., Lemmel, E. M. et al. The effects of strontium ranelate on the risk of vertebral fracture in women with postmenopausal osteoporosis. N Engl J. Med. 2004; 350:459-68.
22) Marie, P. J., Ammann, P., Boivin, G. & Rey, C. Mechanisms of action and therapeutic potential of strontium in bone. Calcif Tissue Int. 2001; 69:121-9.
23) Reginster, J., Seeman, E., De Vernejoul, M., Adami, S., Compston, J., Phenekos, C., Devogelaer, J., Diaz Curiel, M., Sawicki, A. et al. Strontium ranelate reduces the risk of nonvertebral fractures in postmenopausal women with osteoporosis: Treatment of peripheral osteoporosis (TROPOS) study. J Clin Endocrinol Metab. 2005; 90:2816-22.
24) NRC. (1998) Nutrition Requirements of Swine, 10 ed. National Academy Press, Washington, D.C.
25) Kim, T. W. & Lei, X. G. An improved method for a rapid determination of phytase activity in animal feed. J Anim Sci. 2005; 83:1062-7.
26) Gomori, G. A modification of the colorometric phosphorus determination for use with the photoelectric calorimeter. J Lab Clin Med. 1942; 27:955-60.

27) Bowers, G., Jr & McComb, R. A continuous spectrophotometric method for measuring the activity of serum alkaline phosphatase. Clin Chem. 1966; 12:70-89.
28) Turner, C. H. & Burr, D. B. Basic biomechanical measurements of bone: a tutorial. Bone. 1993; 14:595-608.
29) Crenshaw, T. D., Peo, E. J., Lewis, A. J. & Moser, B. D. Bone strength as a parameter for assessing mineralization in swine: A critical review of techniques involved. J Anim Sci. 1981; 53:827-35.
30) Abramoff, M. D., Magelhaes, P. J. & Ram, S. J. Image Processing with Image. J Biophotonics Int. 2004; 11:36-42.
31) Eppard, P. J., Bauman, D. E., Bitman, J., Wood, D. L., Akers, R. M. & House, W. A. Effect of dose of bovine growth hormone on milk composition: alpha-lactalbumin, fatty acids, and mineral elements. J Dairy Sci. 1985; 68:3047-54.
32) House, W. A. & Bell, A. W. Mineral accretion in the fetus and adnexa during late gestation in Holstein cows. J Dairy Sci. 1993; 76:2999-3010.
33) Gill, J. L. Repeated measurement: sensitive tests for experiments with few animals. J Anim Sci. 1986; 63:943-54.
34) Augspurger, N. I., Webel, D. M., Lei, X. G. & Baker, D. H. Efficacy of an *E. coli* phytase expressed in yeast for releasing phytate-bound phosphorus in young chicks and pigs. Anim Sci. 2003; 81:474-83.
35) Han, Y. M., Yang, F., Zhou, A. G., Miller, E. R., Ku, P. K., Hogberg, M. G. & Lei, X. G. Supplemental phytases of microbial and cereal sources improve dietary phytate phosphorus utilization by pigs from weaning through finishing. J Anim Sci. 1997; 75:1017-25.
36) Cromwell, G. L., Coffey, R. D., Parker, G. R., Monegue, H. J. & Randolph, J. H. Efficacy of a recombinant-derived phytase in improving the bioavailability of phosphorus in corn-soybean meal diets for pigs. J Anim Sci. 1995; 73:2000-8.
37) Boyd, R. D., Hall, D. & Wu, J. F. Plasma alkaline phosphatase as a criterion for determining biological availability of phosphorus for swine. J Anim Sci. 1983; 57:396-401.
38) Lei, X. G., Ku, P. K., Miller, E. R., Yokoyama, M. T. & Ullrey, D. E. Supplementing corn-soybean meal diets with microbial phytase maximizes phytate phosphorus utilization by weanling pigs. J Anim Sci. 1993; 71:3368-75.
39) Mitchell, N. & Shepard, N. The sulphur content of chondrocyte nuclei. Histochem Cell Biol. 1983; 80:73-8.
40) Prince, C. W., Rahemtulla, F. & Butler, W. T. Metabolism of rat bone proteoglycans in vivo. Biochem J. 1983; 216:589-96.
41) Hunter, G. K. Role of proteoglycan in the provisional calcification of cartilage. A review and reinterpretation. Clin Orthop Relat Res. 1991:256-80.
42) Dahl, S. G., Allain, P., Marie, P. J., Mauras, Y., Boivin, G., Ammann, P., Tsouderos, Y., Delmas, P. D. & Christiansen, C. Incorporation and distribution of strontium in bone. Bone. 2001; 28:446-53.
43) Knuuttila, M., Lappalainen, R., Lammi, S., Alhava, E. & Olkkonen, H. Interaction between Li, Ni and Sr content in human cancellous bone. Chem Biol Interact. 1982; 40:77-83.
44) Spencer, H., I, L. & Samachson, J. Effect of stable strontium on radio-strontium excretion in man. Radiat Res. 1967; 31:876-88.
45) Pi, M. & Quarles, L. D. A novel cation-sensing mechanism in osteoblasts is a molecular target for strontium. J Bone Miner Res. 2004; 19:862-9.
46) Henrotin, Y., Labasse, A., Zheng, S. X., Galais, P., Tsouderos, Y., Crielaard, J. M. & Rejinster, J. Y. Strontium ranelate increases cartilage matrix formation. J Bone Miner Res. 2001; 16:299-308.
47) Marie, P. J. Strontium ranelate: a physiological approach for optimizing bone formation and resorption. Bone. 2006; 38:S10-4.
48) Shorr, E. & Carter, A. C. The usefulness of strontium as an adjuvant to calcium in the remineralization of the skeleton in man. Bull Hosp Joint Dis. 1952; 13:59-66.
49) National Osteoporosis Foundation 2003 America's Bone Health: The State of Osteoporosis and Low Bone Mass in Our Nation. National Osteoporosis Foundation, Washington, D.C., USA.
50) NIH Consensus Development Panel on Osteoporosis Prevention, Diagnosis and Therapy 2001 JAMA 285:785-795.
51) Rodan G A, Martin, T J 2000 Therapeutic approaches to bone diseases. Science 289:1508-1514.
52) Cheung A M, Feig D S, Kapral M, Diaz-Granados N, Dodin S 2004 Prevention of osteoporosis and osteoporotic fractures in postmenopausal women: Recommendation statement from the Canadian Task Force on Preventive Health Care. Can Med Assoc J 170:1665-1667.
53) Kiberstis P A 2005 BIOMEDICINE: Weeding Out Osteoclasts Science 308: 1379.
54) Manolagas S C 2000 Birth and death of bone cells: basic regulatory mechanisms and implications for the pathogenesis and treatment of osteoporosis. Endocr. Rev. 21:115-137.
55) Delmas P D, Li Z, Cooper C 2004 Relationship Between Changes in Bone Mineral Density and Fracture Risk Reduction With Antiresorptive Drugs: Some Issues With Meta-Analyses J Bone Min Res 19:330-337
56) Udell J A, Fischer M A, Brookhart M A, Solomon D H, Choudhry N K 2006 Effect of the Women's Health Initiative on Osteoporosis Therapy and Expenditure in Medicaid. J Bone Miner Res 21:765-771.
57) Henry Y M, Fatayerji D, Eastell R 2004 Attainment of peak bone mass at the lumbar spine, femoral neck and radius in men and women: relative contributions of bone size and volumetric bone mineral density. Osteoporosis Int 15:263-273.
58) Tan L-J, Lei S-F, Chen X-D, Liu M-Y, Guo Y-F, Xu H, Sun X, Jiang C, Xiao S-M, Guo J-J, Yang Y-J, Deng F-Y, Wang Y-B, Li Y-N, Zhu X-Z, Deng H-W 2007 Establishment of peak bone mineral density in Southern Chinese males and its comparisons with other males from different regions of China J Bone Min Res 25: 114-121.
59) Matkovic V, Jelic T, Wardlaw G M, Ilich J Z, Goel P K, Wright K K, Andon M B, Smith K T, Heaney R P 1994 Timing of Peak Bone Mass in Caucasian Females and. Its Implication for the Prevention of Osteoporosis Inference from a Cross-sectional Model. J. Clin. Invest. 93:799-808
60) Fujita Y, Katsumata K, Unno A, Tawa T, Tokita A 1999 Factors affecting peak bone density in Japanese women Calcif Tissue Int. 64:107-11
61) Bouletreau P H, Bost M, Fontanges E, Lauverjat M, Gutknecht C, Ecochard R, Delmas P D, and Chambrier C 2006 Fluoride exposure and bone status in patients with chronic intestinal failure who are receiving home parenteral nutrition Am. J. Clinical Nutrition, 83: 1429-1437.
62) Miller S C, Bowman B M, Jee W S 1995 Available animal models of osteopenia—small and large. Bone 17:117 S-23S.
63) Pagano P R, Yasuda K, Roneker K R, Crenshaw T D, Lei X G 2007 Supplemental *Escherichia coli* Phytase and Strontium Enhanced Bone Strength of Young Pigs Fed a Phosphorus-adequate Diet J Nutr 137:1795-1801.
64) Mullaney E J, Ullah A H 2003 The term phytase comprises several different classes of enzymes. Biochem Biophys Res Commun. 312:179-184.
65) Rodriguez E, Han Y, Lei X G 1999 Cloning, sequencing, and expression of an *Escherichia coli* acid phosphatase/phytase gene (appA2) isolated from pig colon. Biochem Biophys Res Commun. 257:117-23.
66) Lee S, Kim T, Stahl C H, Lei X G 2005 Expression of *Escherichia coli* AppA2 phytase in four yeast systems. Biotechnol Lett 27:327-34.
67) Kim T, Mullaney E J, Porres J M, Roneker K R, Crowe S, Rice S, Ko T, Ullah A H, Daly C B, Welch R M, Lei X G 2006. Shifting the pH profile of *aspergillus niger* phya phytase to match the stomach environment enhances its effectiveness in animal feeding. Appl Environ Microbiol 72:4397-403.
68) Erlebacher A, Filvaroff E H, Gitelman E, Derynck R 1995 Toward a molecular understanding of skeletal development. Cell 80:371-378.
69) Weitzhandler M, Carrino D A, Caplan A I 1988 Proteoglycans synthesized during the cartilage to bone transition in developing chick embryos. Bone 9:225-233.
70) Hunter G K 1992 In vitro studies on matrix mineralization. In: Bone Hall B K (ed.) Bone metabolism and mineralization, vol. 4. CRC Press, Inc. pp. 225-247.
71) Boivin G, Meunier 2003 The mineralization of bone tissue: a forgotten dimension in osteoporosis research. Osteoporosis Int 14:S19-S24.
72) Roux C, Reginster J-Y, Fechtenbaum J, Kolta S, Sawicki A, Tulassay Z, Luisetto G, Padrino J-M, Doyle D, Prince R, Fardellone P, Sorensen O H, Meunier P J 2006 Vertebral Fracture Risk Reduction With Strontium Ranelate in Women With Postmenopausal Osteoporosis Is Independent of Baseline Risk Factors. J Bone Miner Res 21:536-542.
73) Gomori G 1942 A modification of the colorometric phosphorus determination for use with the photoelectric colorimeter. J. Lab Clin Med. 27:955-60.
74) Roy P K, Witten P E, Hall B K, Lall S P 2002 Effect of dietary phosphorus on bone formation and mineralization of vertebrae in haddock (*Melanogrammus aeglefinus* L.). Fish Physiol. and Biochem. 27:35-48
75) Ralis Z A, Watkins G 1992 Modified Tetrachrome method for osteoid and defectively mineralized bone in paraffin sections. Biotech. Histochem. 67:339-345.
76) Sayers D C, Volpin G, Bentley G 1987 The demonstration of bone and cartilage remodeling using alcian blue and hematoxilin. Stain Tech. 63:59-63.
77) Komegay E T, Qian H 1996 Replacement of inorganic phosphorus by microbial phytase for young pigs fed on a maize-soyabean-meal diet. Br J Nutr 76:563-78.
78) Turner C H, Burr D B 1993 Basic biomechanical measurements of bone: a tutorial. Bone 14:595-608.
79) O'Brien C A, Jia D, Plotkin L I, Bellido T, Powers C C, Stewart S A, Manolagas S C, Weinstein R S. 2004 Glucocorticoids act directly on osteoblasts and osteocytes to induce their apoptosis and reduce bone formation and strength. Endocrinology. 145:1835-1841.
80) Fox J, Miller M A, Newman M K, Metcalfe A F, Turner C H, Recker R R, Smith S Y. 2006 Daily treatment of aged ovariectomized rats with human parathyroid hormone (1-84) for 12 months reverses bone loss and enhances trabecular and cortical bone strength. Calcif Tissue Int 79:262-72.
81) Holstein J H, Menger M D, Scheuer C, Meier C, Culemann U, Wirbel R J, Garcia P, Pohlemann T. 2007 Erythropoietin (EPO): EPO-receptor signaling improves early endochondral ossification and mechanical strength in fracture healing. Life Sci. 80:893-900.
82) Hoshi K, Ejiri S, Ozawa H 2001 Localization alternations of calcium, phosphorus, and calcium-relate organics such as proteoglycans and alkaline phosphatase during bone calcification. J Bone Min Res 16:289-298.
83) French M M, ronald r. Gomes jr R R, Timpl R, Hook M, Czymmek K, Farach-carson M C, Carson D D 2002 Chondrogenic Activity of the Heparan Sulfate Proteoglycan Perlecan Maps to the N-terminal Domain I. J Bone Min Res 17:48-55
84) Nielson S P 2004 The biological role of strontium. Bone 35: 583-588.
85) Davies D R, Bassingthwaighte J B, Kelly P J 1976 Transcapillary exchange of strontium and sucrose in canine tibia. J Appl Physiol. 40:17-22.
86) Boivin G, Deloffre P, Perrat B, Panczer G, Boudeulle M, Mauras Y 1996 Strontium distribution and interactions with bone mineral in monkey iliac bone after strontium salt administration. J Bone Min Res 11:1302-1311.
87) Baud C A, Bang S, Very J M 1977 Minor elements in bone mineral and their effects on its solubility. J. Biol. Buccale 5:195-202.
88) Palmer R F, Thompson R C 1964 Strontium-calcium interrelationships in the growing rat Am J. Physiol 207: 561-566.
89) Pi M, Quarles L D 2004 A Novel Cation-Sensing Mechanism in Osteoblasts Is a Molecular Target for Strontium. J Bone Min Res 19:862-869.
90) Delannoy P, Bazot D, Marie P J 2002 Long-term treatment with strontium renelate increases vertebral bone mass without deleterious effect in mice. Metabolism. 51:906-909.
91) Shahnazari M, Lang D H, Fosmire G J, Sharkey N A, Mitchell A D, Leach R M 2007 Strontium administration in young chickens improves bone volume and architecture but not enhance bone structural and material strength. Calcif. Tissue Int 80:160-166.
92) Reddy N R, Sathe S K, Salunkhe D K 1982 Phytase in legumes and cereals. Adv Food Res 28:1-92.
93) Sakamoto K, Vucenik I, Shamsuddin A M 1993 [$^3$H] Phytic Acid (Inositol Hexaphosphate) Is Absorbed and Distributed to Various Tissue in Rats. J Nutr 123:713-720.
94) Berridge M J, Irvine R F 1989 Inositol phosphates and cell signaling. Nature (Lond.) 341:197-205.
95) Atkinson Sa, Chappell J E, Clandinin M T. Calcium supplementation of mother's milk for low birth weight infants: problems related to absorption and excretion. Nutr Res 1995; 7:813-23.
96) Dewey K G, Finley D A, Lonnerdal B. Brat milk volume and composition during late lactation (7-20 months). J Pediatr Gastroenterol Nutr 1984; 3:713-20.
97) Heinig M J, Nommsen LALinoleic acid, Peerson J M, Lonnerdal, Dewey K G. Energy and protein intakes of breast-fed and formula-fed infants during the first year of life and their association with growth velocity: the DARLING study. Am J Clin Nutr 1993; 58:152-61.
98) Specker B L, Beck A, Kalkwarf H, Ho M. Randomized trial of varying mineral intake on total body bone mineral accretion during the first year of life Pediatrics 1997; 99:E12.

99) Fomon S J, Nelson S E. Calcium, phosphorus, magnesium and sulphur. In: Fomon S J, ed. Nutrition of normal infants. St. Louis: Mosby-Year Book Inc, 1993. Pp 192-216.
100) Slemenda C W, Reister T K, Hui S L, Miller J Z, Christian J C, Johnston C C Jr. Influences on skeletal mineralization in children and adolescents: evidence for varying effects of sexual maturation and physical activity. J Pediatr 1994; 125:201-7.
101) Nordin BECEuropean Commission Phosphorus. In: Truswell A S, Dreosti I E, English R M, Rutishauser I H E, Palmer N. eds. Recommended Nutrient Intakes. Australian papers. Sydney: Australian Professional Publications, 1990.
102) Nordin BECEuropean Commission. Calcium, phosphate and magnesium metabolism. Edinburgh: Churchill Livingstone, 1976.
103) Nordin BECEuropean Commission. Phosphorus. J Food Nutr 1989; 45:62-75.
104) Heaney R P, Recker R R. Effects of nitrogen, phosphorus and caffeine on calcium balance in women. J Lab Clin Med 1982; 99:46-55.
105) Stanbury S W. The phosphate ion in chronic renal failure. In: Hioco D J, ed. Phosphate et Metabolisme Phosphocalcique. Paris: Sandoz Laboratories, 1971.
106) Wilkinson R. Absorption of calcium, phosphorus and magnesium. In: Nordin BECEuropean Commission, ed. Calcium, phosphate and magnesium metabolism. Edinburgh: Churchill Livingstone, 1976. Pp 36-112.

The invention claimed is:

1. A method of improving bone structure, function and/or strength in a mammal, the method comprising:
   administering to said mammal a composition comprising a therapeutically effective amount of strontium and a therapeutically effective amount of phytase enzyme.

2. The method of claim 1, wherein said phytase enzyme comprises a microbial phytase or a plant phytase.

3. The method of claim 2 wherein said phytase enzyme is a microbial phytase enzyme comprising a fungal phytase.

4. The method of claim 2 wherein said phytase enzyme is a microbial phytase enzyme comprising a bacterial phytase.

5. The method of claim 2 wherein said phytase enzyme is a microbial phytase enzyme comprising an *E. coli* phytase or an *Aspergillus phytase*.

6. The method of claim 5, wherein said phytase enzyme comprises an *E. coli* AppA phytase or an *Aspergillus niger* PhyA or PhyB phytase.

7. The method of claim 6 wherein said AppA phytase is an AppA2 phytase.

8. The method of claim 1 wherein said administering is carried out by feeding said mammal the composition.

9. The method of claim 1 wherein the composition further comprises:
   a therapeutically effective amount of phytic acid and/or phytate.

10. The method of claim 9, wherein said phytic acid and/or phytate is at least 0.1% of the composition.

11. The method of claim 8 wherein said phytase is present in said feed composition at least 1000 U/kg.

12. The method of claim 8 wherein said phytase is present in said feed composition at least 2000 U/kg.

13. The method of claim 1 wherein said composition comprises at least 2.5 mg/kg strontium.

14. The method of claim 1 wherein said composition comprises 25-50 mg/kg strontium.

15. The method of claim 1 wherein said mammal is selected from the group consisting of dogs, cats, horses, cattle, sheep, goats, swine, and humans.

16. A method of improving bone structure, function and/or strength in an animal, the method comprising;
   administering to said animal a composition comprising a therapeutically effective amount of strontium and a therapeutically effective amount of phytase enzyme.

17. A method of treating osteoporosis in a subject, the method comprising:
   administering to the subject a composition comprising a therapeutically effective amount of phytase enzyme and a therapeutically effective amount of strontium.

18. The method of claim 17 wherein said composition further comprises:
   a therapeutically effective amount of phytic acid and/or phytate.

19. The method of claim 17 wherein said phytase enzyme comprises a microbial phytase or a plant phytase.

20. The method of claim 19 wherein said phytase enzyme is a microbial phytase enzyme comprising a fungal phytase.

21. The method of claim 19 wherein said phytase enzyme is a microbial phytase enzyme comprising a bacterial phytase.

22. The method of claim 19 wherein said phytase enzyme is a microbial phytase enzyme comprising an *E. coli* phytase or an *Aspergillus* phytase.

23. The method of claim 22 wherein said *E. coli* phytase comprises an AppA phytase.

24. The method of claim 23 wherein said AppA phytase is an AppA2 phytase.

25. The method of claim 22 wherein said phytase is an *Aspergillus niger* PhyA or PhyB phytase.

26. The method of claim 17 wherein said composition is administered orally as a dietary supplement.

27. The method of claim 18 wherein said phytic acid and/or phytate is administered orally as a dietary supplement.

28. The method of claim 18 wherein said phytase, strontium and phytic acid and/or phytate are administered in a single dietary supplement composition.

29. A method of improving bone structure, function and/or strength in a fish or bird, the method comprising:
 administering to said fish or bird a composition comprising a therapeutically effective amount of strontium and a therapeutically effective amount of phytase enzyme.

* * * * *